(12) United States Patent
Holmstrom

(10) Patent No.: US 12,011,181 B2
(45) Date of Patent: Jun. 18, 2024

(54) ENDOSCOPIC SYSTEM WITH PUMP CONTROL

(71) Applicant: Kunnskap Medical, LLC, South Jordan, UT (US)

(72) Inventor: Michael C. Holmstrom, Cottonwood Heights, UT (US)

(73) Assignee: Kunnskap Medical, LLC, South Jordan, UT (US)

( * ) Notice: Subject to any disclaimer, the term of this patent is extended or adjusted under 35 U.S.C. 154(b) by 0 days.

(21) Appl. No.: 17/395,458

(22) Filed: Aug. 6, 2021

(65) Prior Publication Data

US 2022/0046165 A1 Feb. 10, 2022

Related U.S. Application Data

(60) Provisional application No. 63/063,827, filed on Aug. 10, 2020.

(51) Int. Cl.
*A61B 17/16* (2006.01)
*A61B 1/00* (2006.01)
(Continued)

(52) U.S. Cl.
CPC ...... *A61B 17/1604* (2013.01); *A61B 1/00006* (2013.01); *A61B 1/00013* (2013.01);
(Continued)

(58) Field of Classification Search
CPC ............ A61B 17/1604; A61B 1/00006; A61B 1/00013; A61B 1/0005; A61B 1/015; A61B 1/04; A61B 1/317; A61B 17/00234; A61B 18/148; A61B 18/22; A61B 2017/00367; A61B 2018/00589; A61B 2018/00595; A61B 2018/00982; A61B 2217/005; A61B 2217/007; A61B 2218/002; A61B 1/00009; A61B 34/25; A61B 18/1482; A61B 18/1492; A61B 90/30; A61B 90/36; A61B 2017/1602; A61B 2018/00577; A61B 2018/00601; A61B 2018/00607; A61B 2018/00642; A61B 2018/00702; A61B 2018/00744; A61B 2018/167; A61B 2090/309; A61B 2218/007; A61B 2218/008; A61B 1/045; A61M 13/003; A61M 13/006; A61M 2202/0225; A61M 2205/3334; A61M 2205/3344; A61M 2205/502; A61M 2205/587; A61M 2205/6072; G06T 7/0012;
(Continued)

(56) References Cited

U.S. PATENT DOCUMENTS 8,801,654 B2 8/2014 Mollstam et al.
9,901,670 B2 2/2018 Moolstam
(Continued)

FOREIGN PATENT DOCUMENTS

CN 111295127 6/2020

*Primary Examiner* — Michael E Teitelbaum
(74) *Attorney, Agent, or Firm* — Foley & Lardner LLP

(57) ABSTRACT

Endoscopic image analysis, endoscopic procedure analysis, and/or component control systems, methods and techniques are disclosed that can analyze images of an endoscopic system and/or affect an endoscopic system to enhance operation, user and patient experience, and usability of image data and other case data.

19 Claims, 15 Drawing Sheets

(51) Int. Cl.

| | |
|---|---|
| A61B 1/015 | (2006.01) |
| A61B 1/04 | (2006.01) |
| A61B 1/045 | (2006.01) |
| A61B 1/317 | (2006.01) |
| A61B 17/00 | (2006.01) |
| A61B 18/00 | (2006.01) |
| A61B 18/14 | (2006.01) |
| A61B 18/22 | (2006.01) |
| A61M 13/00 | (2006.01) |
| G05D 7/06 | (2006.01) |
| G05D 16/20 | (2006.01) |
| G06T 7/00 | (2017.01) |
| G16H 30/20 | (2018.01) |
| H04N 7/18 | (2006.01) |
| H04N 23/52 | (2023.01) |
| H04N 23/56 | (2023.01) |
| H04N 23/61 | (2023.01) |
| H04N 23/74 | (2023.01) |
| H04N 23/50 | (2023.01) |

(52) U.S. Cl.
CPC ............ *A61B 1/0005* (2013.01); *A61B 1/015* (2013.01); *A61B 1/04* (2013.01); *A61B 1/045* (2013.01); *A61B 1/317* (2013.01); *A61B 17/00234* (2013.01); *A61B 18/148* (2013.01); *A61B 18/22* (2013.01); *A61M 13/003* (2013.01); *G06T 7/0012* (2013.01); *G16H 30/20* (2018.01); *H04N 7/183* (2013.01); *H04N 23/52* (2023.01); *H04N 23/56* (2023.01); *H04N 23/61* (2023.01); *H04N 23/74* (2023.01); *A61B 2017/00367* (2013.01); *A61B 2018/00589* (2013.01); *A61B 2018/00595* (2013.01); *A61B 2018/00982* (2013.01); *A61B 2217/005* (2013.01); *A61B 2217/007* (2013.01); *A61B 2218/002* (2013.01); *G05D 7/0676* (2013.01); *G05D 16/2066* (2013.01); *G06T 2207/10016* (2013.01); *G06T 2207/10068* (2013.01); *G06T 2207/10152* (2013.01); *G06T 2207/20081* (2013.01); *G06T 2207/20084* (2013.01); *G06T 2207/30004* (2013.01); *G06T 2207/30168* (2013.01); *H04N 23/555* (2023.01)

(58) Field of Classification Search
CPC . G06T 2207/10016; G06T 2207/10068; G06T 2207/10152; G06T 2207/20081; G06T 2207/20084; G06T 2207/30004; G06T 2207/30168; G06T 7/0002; G06T 2207/10024; G06T 2207/30008; G06T 2207/30028; G06T 2207/30061; G06T 2207/30092; G16H 30/20; G16H 15/00; G16H 30/40; G16H 50/20; H04N 5/22521; H04N 5/2256; H04N 5/23218; H04N 5/2354; H04N 7/183; H04N 2005/2255; H04N 7/185; H04N 23/52; H04N 23/56; H04N 23/61; H04N 23/74; H04N 23/555; G05D 7/0676; G05D 16/2066

See application file for complete search history.

(56) References Cited

U.S. PATENT DOCUMENTS

| | | | |
|---|---|---|---|
| 10,269,454 | B2 | 4/2019 | Hanning et al. |
| 10,582,971 | B2* | 3/2020 | Amiot ................ A61B 34/10 |
| 10,600,015 | B2 | 3/2020 | Baumberger et al. |
| 10,671,896 | B2 | 6/2020 | Reicher et al. |
| 10,729,502 | B1 | 8/2020 | Wolf et al. |
| 10,740,552 | B2 | 8/2020 | Hanning |
| 10,776,920 | B2 | 9/2020 | Linard et al. |
| 10,866,015 | B2 | 12/2020 | Clements |
| 10,878,966 | B2 | 12/2020 | Wolf et al. |
| 10,943,682 | B2 | 3/2021 | Wolf et al. |
| 11,013,398 | B2 | 5/2021 | Shen et al. |
| 11,026,561 | B2 | 6/2021 | Venkataraman et al. |
| 11,065,079 | B2 | 7/2021 | Wolf et al. |
| 11,100,373 | B1 | 8/2021 | Crosby et al. |
| 11,116,587 | B2 | 9/2021 | Wolf et al. |
| 11,730,491 | B2 | 8/2023 | Holmstrom |
| 2001/0027272 | A1 | 10/2001 | Saito et al. |
| 2002/0013512 | A1 | 1/2002 | Sendai et al. |
| 2010/0249507 | A1 | 9/2010 | Prisco et al. |
| 2011/0237880 | A1* | 9/2011 | Hamel ............ A61B 1/000094 |
| | | | 600/104 |
| 2013/0267892 | A1 | 10/2013 | Woolford |
| 2015/0119645 | A1* | 4/2015 | Baldwin ................ A61B 17/22 |
| | | | 600/114 |
| 2018/0286047 | A1 | 10/2018 | Linard et al. |
| 2018/0344131 | A1 | 12/2018 | Takahira et al. |
| 2018/0366231 | A1 | 12/2018 | Wolf et al. |
| 2020/0085286 | A1* | 3/2020 | Shener-Irmakoglu ............ |
| | | | A61M 5/16877 |
| 2020/0184640 | A1 | 6/2020 | Mahadik et al. |
| 2020/0211181 | A1 | 7/2020 | Govari et al. |
| 2020/0237452 | A1 | 7/2020 | Wolf et al. |
| 2020/0268457 | A1 | 8/2020 | Wolf et al. |
| 2020/0268469 | A1 | 8/2020 | Wolf et al. |
| 2020/0268472 | A1 | 8/2020 | Wolf et al. |
| 2020/0272660 | A1 | 8/2020 | Wolf et al. |
| 2020/0273548 | A1 | 8/2020 | Wolf et al. |
| 2020/0273552 | A1 | 8/2020 | Wolf et al. |
| 2020/0273557 | A1 | 8/2020 | Wolf et al. |
| 2020/0273560 | A1 | 8/2020 | Wolf et al. |
| 2020/0273561 | A1 | 8/2020 | Wolf et al. |
| 2020/0273563 | A1 | 8/2020 | Wolf et al. |
| 2020/0273564 | A1 | 8/2020 | Dettinger et al. |
| 2020/0273575 | A1 | 8/2020 | Wolf et al. |
| 2020/0273577 | A1 | 8/2020 | Wolf et al. |
| 2020/0273581 | A1 | 8/2020 | Wolf et al. |
| 2020/0304753 | A1 | 9/2020 | Venkataraman et al. |
| 2020/0305698 | A1 | 10/2020 | Oosake |
| 2020/0337537 | A1 | 10/2020 | Hirasawa et al. |
| 2020/0372998 | A1 | 11/2020 | Venkataraman et al. |
| 2021/0012032 | A1 | 1/2021 | Bishop et al. |
| 2021/0012868 | A1 | 1/2021 | Wolf et al. |
| 2021/0045811 | A1* | 2/2021 | Shelton ............ A61B 1/00087 |
| 2022/0000338 | A1* | 1/2022 | Saikou ................ G06T 7/50 |
| 2022/0046165 | A1 | 2/2022 | Holmstrom |
| 2022/0167837 | A1* | 6/2022 | Onikubo ............ A61B 1/00149 |
| 2022/0218427 | A1 | 7/2022 | Tomatsu |

* cited by examiner

Procedure Report by Facility / Surgeon — 1604

System: BETELGEUSE HEALTHCARE — 1602
Procedure(s): ACL RECONSTRUCTION, +/- MENISCECTOMY, +/- CHONDROPLASTY — 1606
Dates: 01/01/2020 - 12/31/2020 — 1608

| Surgeon | # Cases | Avg Time | Avg Pressure | Extravasation Score | Fluid Used |
|---|---|---|---|---|---|
| OVERALL | 595 | 56.4 | 30 | 1934 | 2259 |
| HOSPITAL A | | | | | |
| Z Beeblebrox | 12 | 86.2 | 42 | 3201 | 4305 |
| A Dent | 98 | 64.3 | 31 | 2233 | 2309 |
| F Prefect | 132 | 54.7 | 29 | 1734 | 1805 |
| HOSPITAL B | | | | | |
| S Bartfast | 6 | 132.3 | 51 | 5867 | 5309 |
| T McMillan | 43 | 74.3 | 37 | 3001 | 3332 |
| SURG CENTER C | | | | | |
| H Desiato | 98 | 48.1 | 25 | 1402 | 2103 |
| E Kapelsen | 45 | 61.8 | 37 | 2754 | 1887 |
| C Mown | 152 | 42.8 | 27 | 1325 | 2008 |
| B Versenwald | 9 | 114.2 | 43 | 5251 | 6305 |

FIG. 16

ENDOSCOPIC SYSTEM WITH PUMP CONTROL

RELATED APPLICATIONS

This application claims the benefit of priority under 35 U.S.C. § 119 (e) to U.S. Provisional Patent Application 63/063,827 titled "SYSTEMS AND METHODS FOR REAL-TIME IMAGE ANALYSIS TO AFFECT THE DISPLAY AND ENVIRONMENT IN ENDOSCOPIC PROCEDURES," filed Aug. 10, 2020, which is hereby incorporated herein by reference in its entirety.

TECHNICAL FIELD

The present disclosure relates generally to the field of endoscopic procedures and more particularly to endoscopic image analysis, procedure analysis, and/or component control systems, methods and techniques to analyze images in and/or affect an endoscopic system.

BACKGROUND

Endoscopy is a field and technology for viewing internal features of the body of a patient using minimally-invasive techniques. An endoscope provides a procedure team (e.g., one or more medical practitioners, such as a physician or surgeon, nurses, technicians) access to visualize an area to be addressed within the body of a patient. The actual form of the endoscope can vary, and may include, for example, a flexible scope often used in gastroenterology, anesthesiology, or pulmonology. Other types of endoscopes may be rigid, such as those often used in arthroscopy, laparoscopy, thoracoscopy or otolaryngology.

A high-intensity light source is generally coupled to the endoscope to provide illumination to the area being addressed. The reflected light is captured by a camera, either inside the body itself, or by being transmitted through the scope to a camera outside the body. The raw data captured by the camera is then processed into a suitable format, which is then shown on a display device, which the operator observes to complete the procedure.

A goal of endoscopy is to diagnose and/or treat a problem. To do that, adequate visualization is important for patient safety and for the procedure team to efficiently perform the procedure. Multiple aspects of the endoscopic system may be manipulated by the procedure team to maximize visualization. For example, in many procedures, a liquid or gaseous medium is introduced. In arthroscopy, an aqueous fluid is circulated through the area being addressed. In laparoscopy, carbon dioxide gas is most frequently used. This medium is often manipulated by the procedure team to increase visualization. Examples of this manipulation of the medium include: In arthroscopy, where there is bleeding, the pressure of the fluid can be increased while the bleeding is stopped. In laparoscopy, when there is decreased visualization because of electrocautery smoke, the flow of gas can be increased to clear the abdomen. Other similar mechanisms are frequently utilized to help with visualization in other types of endoscopy, whether it is manipulating a medium or adjusting any other part of the endoscopic system.

Despite many advances over the years, there are still fundamental limitations to current techniques. As an example, in manual arthroscopic systems that do not use pumps, adjustment of pressure involves having someone raise or lower bag(s) of fluid. Most procedure teams using this method simply raise the bag(s) to a standard height and leave them there the whole case without regard to actual pressure in the system. This can lead to poor image quality if the pressure is too low, or potential extravasation if the pressure is too high. In order to adjust flow manually, a member of the procedure team generally manipulates a stopcock or pinches tubing.

In endoscopic systems with pumps, there is somewhat improved control of flow and/or pressure. Differences between various pumps include: whether pressure is measured using the same tubing that delivers a medium or whether there is dedicated pressure tubing, how quickly a pump responds to changes in pressure, how accurate reported pressures and/or flows match actual values, and what pre-defined modes are available to try to clear the area being visualized with generally fixed changes to pressure and/or flow.

There are limitations, however, with existing systems. While pumps can control flow and/or pressure better than systems without a pump, adjustments to these parameters still require manual input from the procedure team. To make changes to the endoscopic system, a member of the procedure team must manually adjust pressure, flow, or another aspect of the system until the image improves. This interrupts the rhythm of the procedure and diverts attention from the procedure itself to the tools used to affect the procedure. Alternatively, an additional person may be required to assist in the procedure to adjust pressure, flow, or another aspect of the system manually, requiring extra costs and/or creating additional potential to contaminate the sterile field. Additionally, if someone besides the surgeon or other primary user is making adjustments to the endoscopic system, this requires that person to be experienced in knowing what the surgeon or other primary user specifically needs in their image, as well as knowledge of what specific adjustments need to be made to achieve an optimal image. In many facilities, because of various staffing concerns, there may be staff who are not as familiar with the particular primary user and/or equipment, which can make relying on the staff to adjust things to the primary user's preferences less than ideal.

Other disadvantages to manual control include, for example, forgetting to restore the system back to a nominal state once adequate visualization is restored. If the pressure in an arthroscopic shoulder case is left elevated, for example, it can lead to increased extravasation of fluid into the surrounding tissues. If flow is left elevated, increased fluid or gas will be used, increasing costs and materials. In an ideal situation, pressures and flows of a medium will be continually reduced to the lowest levels possible to allow adequate visualization, and increased as needed in the lowest increments and for the shortest times possible to achieve a good image.

There are some feedback functions in existing endoscopic systems, but these feedback functions are generally on a component basis. Pumps, for example, generally allow a user to set a target pressure. These pumps then use various means to measure the pressure in an area being addressed and have the ability to adjust delivery of a medium to match that given target pressure. Some pumps can adjust flows from an outflow cannula to a separate device like a shaver when that device is activated in order to try to balance inflow and outflow. These methods of using feedback to adjust a pump are proxies for what helps provide a good image in many cases, but these methods of using feedback lack actual evaluation or consideration of the image itself in their feedback loops.

There have been some rudimentary attempts at adjusting flows and/or pressures of a system based on characteristics of the outflow medium measuring, for example, its color and/or turbidity. This measurement of fluid characteristics is generally done at the pump component level and does not take into account an actual image of the present view. Again, characteristics of the outflow medium are being used as a proxy for an endoscopic image, but an endoscopic image is not being evaluated.

Most systems also allow for some rudimentary adjustments to balance the light source and camera using basic photographic functions used in and adopted from non-medical environments. At the beginning of a case, for example, an endoscopic system might be "white-balanced" to adjust the color temperature. Many systems also have an "auto-shutter" function, which effectively changes the shutter speed to account for differences in the lighting to keep the overall image in the best dynamic range for the camera system. These adjustments are fairly generic and generally have little to do with the specifics of a procedure and do not consider view quality during a procedure.

While the examples above involve pressure and/or flow of a viewing medium, other components of an endoscopic system have additional parameters that can be adjusted to enhance operation and/or utility of the endoscopic system. Examples include, but are not limited to, speed of motorized instruments, electrocautery levels and modes, suction levels for shavers and burrs, and focus of a camera. Presently, these require manual adjustment by either the primary user or another member of the procedure team and, in some instances, require a non-sterile member of the procedure team to physically move over to the component to make adjustments on that component directly.

SUMMARY

The present disclosure is directed to systems and methods that can analyze one or more images of a view provided by an endoscope of an endoscopic system and/or that can affect one or more components of the endoscopic system and/or enhance the utility of information of the endoscopic system.

Additional aspects and advantages will be apparent from the following detailed description of preferred embodiments, which proceeds with reference to the accompanying drawings.

BRIEF DESCRIPTION OF THE DRAWINGS

FIG. 16 shows a sample report that can be generated by an endoscopic procedure analysis system using aggregated endoscopic case data of a central datastore.

DETAILED DESCRIPTION

Figure 1:
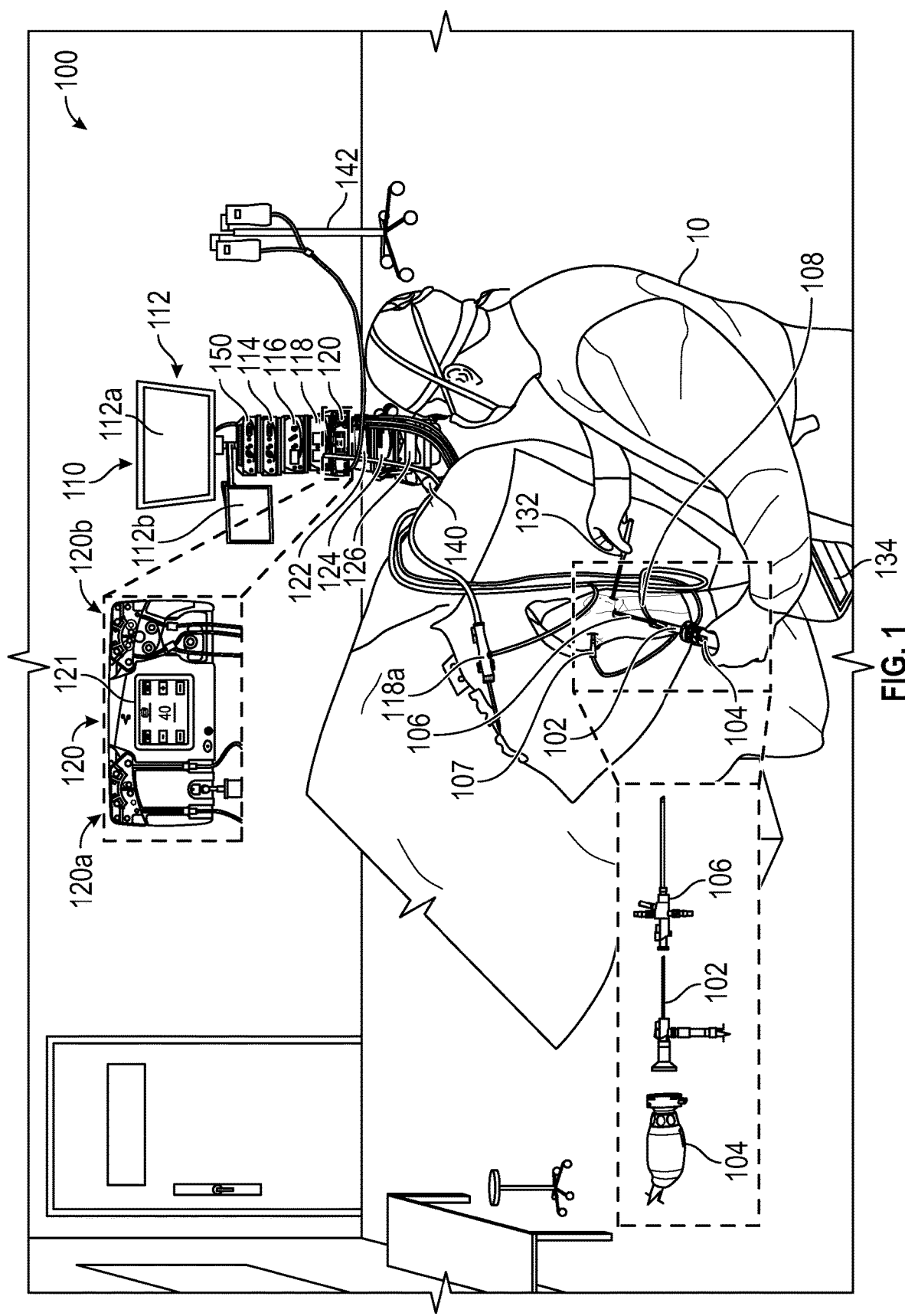
FIG. 1 is a view of an endoscopic system, according to one embodiment of the present disclosure, as viewed in an operating room or a procedure room.

The present disclosure is directed to endoscopic systems, and more particularly to systems and methods of image and/or environmental analysis to automate control of an endoscopic system and/or to optimize utility of an endoscopic image. Endoscopy is a field and technology for viewing internal features of the body of a patient using minimally-invasive techniques. Endoscopy broadly includes any procedure performed to access an area within the body of a patient using an endoscope. The endoscope provides a procedure team (e.g., one or more medical practitioners, such as a physician or surgeon, nurses, technicians) access to visualize the area to be addressed within the body of a patient. There are various forms of endoscopes, and may include, for example, a flexible scope often used in gastroenterology, anesthesiology, or pulmonology. Other types of endoscopes may be rigid, such as those often used in arthroscopy, laparoscopy, thoracoscopy or otolaryngology. While the term endoscopy is sometimes used specifically when referring to examining a person's digestive tract, as used herein the term "endoscopy" refers to the broader definition of accessing any area of the body, including but not limited to the digestive tract.

A light source provides illumination to the area being addressed and the endoscope provides views or visualization of that area. The reflected light is captured by a camera, either inside the body itself (e.g., a chip-on-tip imager at a distal tip of the endoscope or otherwise within the endoscope), or by being transmitted through optics of the scope to a camera outside the body. The raw image data captured by the camera is then processed into a suitable format, which is then shown on a display device, which the operator observes to complete the procedure.

A goal of endoscopy is to diagnose and/or treat a problem. To do that, adequate visualization is important for patient safety and for the procedure team to efficiently and effectively perform the procedure. Multiple aspects of the environment may be manipulated by the procedure team to maximize visualization. For example, in many procedures, a liquid or gaseous medium is introduced to facilitate visualization. In arthroscopy, an aqueous fluid is circulated through the area being addressed. In laparoscopy, carbon dioxide gas is most frequently used. This medium is often manipulated by the procedure team to increase or otherwise enhance visualization. Examples of this manipulation include: In arthroscopy, where there is bleeding, the pressure of the fluid can be increased to halt or otherwise slow the bleeding while the procedure team stops the bleeding (e.g., cauterization). In laparoscopy, when there is decreased visualization because of electrocautery smoke, the flow of gas can be increased to clear the abdomen. Other similar mechanisms are frequently utilized to help with visualization in other types of endoscopy, whether it is manipulating a medium or adjusting any other part of the endoscopic system.

The present disclosure is directed to systems and methods that can analyze an image and/or the environment during an endoscopic procedure and that can utilize that analysis to do one or more of the following: automate control of one or more components of the system, increase the utility of the image during the procedure, and increase the utility of the image after the procedure. In some embodiments, analysis of the image and/or the environment can be performed by an endoscopic system itself (e.g., within a component of an endoscopic system), such as with specialized onboard hardware and/or software algorithms. In other embodiments, the analysis of the image and/or the environment can be done in a separate analysis device. The separate analysis device may be positioned between the output of an image processing component and the display of the endoscopic system. The separate analysis device alternatively could be in a position that is not directly between the image processing component and the display. For example, a splitter could be used to separate image data to be sent to two devices (e.g., the display and the analysis device) in parallel. A more specific example of this use of a splitter would include sending a video signal from a video component to both a display and an analysis device in parallel. In another example, image data could be sent to the image processing component from a display. Additionally, in still other embodiments, the analysis of the image and/or the environment can take place in a different (e.g., remote) location from the endoscopic system.

Endoscopic image analysis systems, methods, and techniques according to the present disclosure can receive image data, endoscopic system state data, and/or environmental data, and process the image data, endoscopic system state data, and/or environmental data to ascertain characteristics of an image of a view provided by a scope during an endoscopic procedure. Various algorithms can be used to determine these characteristics. The characteristics can be used to control the endoscopic system, for example to optimize or otherwise enhance a view provided by an endoscope. The characteristics can also be used to provide increased utility of the endoscopic system during and/or at a conclusion of the procedure. The characteristics can also be used to generate actionable events to optimize or otherwise enhance the safety and efficiency of the procedure. The characteristics can be stored and used after the procedure to provide increased utility of the image data obtained by the endoscopic system, such as for later analysis and/or future improvements to the disclosed embodiments (e.g., as training data, feedback, or the like).

A system for performing an endoscopic procedure, according to one embodiment, may include an endoscope, a camera (or other imager), a medium management system, an image analysis engine and a control engine. The system may include additional components that are known to persons of ordinary skill, including, but not limited to: a light source, a display monitor, a tower, and the like. The system enables a procedure team to perform an endoscopic procedure and the various components can play a role in such a procedure.

The endoscope is to provide a user (e.g., a surgeon) access to (e.g., a view of) an area (e.g., one or more structures) to be visualized that is inside the body of a patient. The endoscope can include optics that direct reflected light for viewing by the user. The endoscope can include an imager and/or a camera that captures image data of the area to be visualized. Stated otherwise, the endoscope can provide a view of an area within the body of the patient that is within a field of vision of the endoscope. The user can direct the field of vision within the body of the patient toward the area to be visualized. Stated otherwise, the area to be visualized can be any area within the body of the patient that is accessed by the endoscope and toward which the field of vision of the endoscope is directed.

The camera is to capture image data of the area to be visualized (e.g., the area within the field of vision of the endoscope). As mentioned, the camera (or similar imager) may be part of the endoscope (e.g. a chip-on-tip endoscope) and capture light directly reflected from the area to be visualized, or the camera can be a separate component that captures image data based on light reflected from the area to be visualized which passes through optics of the endoscope (e.g., a camera external to the patient body). The image data of the area to be visualized can be provided, for example, to a display on which the area within the body can be visualized, which means the area is displayed, portrayed, or otherwise presented on a screen of the display.

The medium management system (e.g., pump, insufflator, outflow control) can manage a viewing medium in the area to be visualized. The viewing medium may be a suitable fluid, which may be liquid or gas. The medium management system can provide the viewing medium through an inflow cannula to the area to be visualized. In some embodiments, the inflow cannula may be incorporated into a sheath accompanying the endoscope while in other embodiments a separate cannula may be used. In some embodiments, a medium delivery device (e.g., pump, insufflator) of the medium management system may only provide or otherwise regulate inflow of viewing medium to the area to be visualized. In some embodiments, a medium delivery device of the medium management system can provide or otherwise regulate inflow of viewing medium and the medium management system can also include an outflow control component to regulate outflow of viewing medium from the area to be visualized. Stated differently, the medium management system may be configured to both deliver and regulate inflow and regulate outflow of viewing medium at the area to be visualized. In still other embodiments, the medium management system may not include a medium delivery device and instead may include an outflow control device to regulate outflow of viewing medium from the area to be visualized. For example, in an embodiment using liquid as a medium, gravity may be used to deliver or otherwise provide viewing medium and the system may lack control of delivery or inflow of viewing medium to the area to be visualized, and instead may control or otherwise influence the medium at the area to be visualized by controlling or otherwise regulating only the outflow. The outflow control component of a medium management system may be a dedicated device (e.g., valve, suction) or may be integrated with another component, such as a tool, instrument, or other implement (e.g., suction of a shaver).

The image analysis engine receives an image of the view of the area within the body of the patient that is within a field of vision of the endoscope, which is the view provided by the endoscope of the area to be visualized. The image received is from the image data captured by the camera. The image data captured by the camera may be video, in which case the image received by the image analysis engine may be one or more individual frames from the video. In some embodiments, the image analysis engine simultaneously or concurrently receives multiple images, including a combination of current and/or previous frames from video, and uses the multiple images for an analysis. The image data captured by the camera may be raw image data from which an image can be extracted or otherwise generated.

The image analysis engine can determine a characteristic of the image received. In some embodiments, the image analysis engine can determine a characteristic in each image of a plurality of images received. In some embodiments, the image analysis engine can determine a characteristic in multiple images received. An image characteristic can be any feature, quality, attribute, or the like of the image that the image analysis engine may be able to identify (or otherwise be configured to ascertain). A few examples of characteristics of an image may include, but are not limited to: air (or bubble or presence of air), out of focus, cloudy, bloody, out of body, and good. Other examples of characteristics of an image may include, but are not limited to: patellofemoral compartment, medial compartment, notch, and lateral compartment, if the area being examined were, for example, a knee. Still other examples of characteristics of an image, from laparoscopy, may include, but are not limited to: smoky, out of focus, bloody, and good. As can be appreciated, as the image analysis engine can determine a characteristic of an image, by corollary the image analysis engine can in some instances be determining a characteristic of a view provided by the endoscope.

As can be appreciated, an image may have a variety of characteristics, and the image analysis engine may classify the image based on the variety of characteristics, such as according to a dominant, primary, and/or most relevant characteristic.

The image analysis engine may determine one or more characteristics of an image according to an algorithm. In some embodiments, the image analysis engine may determine one or more characteristics of an image according to one or more algorithms of a neural network. Stated otherwise, the image analysis engine may determine one or more characteristics of an image using machine learning and/or artificial intelligence. The image analysis engine may include a neural network that can be trained or otherwise can learn to ascertain characteristics of an image. In some embodiments, the image analysis engine may determine the one or more characteristics based on pixel analysis of pixels of a digital image. In some embodiments, the image analysis engine may determine the one or more characteristics based on analysis of a red, green, blue (RGB) value and/or a cyan, magenta, yellow, black (CMYK) value of one or more pixels of the image data. In some embodiments, the image analysis engine may determine the one or more characteristics based on image processing including but not limited to color detection and edge detection. In some embodiments, the image analysis engine determines a plurality of characteristics of the image.

In some embodiments, the image analysis engine may include one or more categories (i.e., categories of characteristics) each including or otherwise organizing multiple characteristics. The image analysis engine may determine a dominant characteristic within each of the one or more categories. The image analysis engine may determine the dominant characteristic within each of the one or more categories by determining and/or evaluating one or more characteristics of the image. The one or more categories of characteristics may be predefined, such that the image analysis engine can be configured in advance to determine the one or more characteristics in each of the one or more categories. The dominant characteristic within each category may be used as a classification of the image.

In some embodiments, the image analysis engine may include one or more categories (i.e., categories of characteristics and/or classifications) each including or otherwise organizing multiple characteristics to make possible multiple potential classifications. The image analysis engine may classify an image (or otherwise assign an image to a classification) within each of the one or more categories by determining and/or evaluating one or more characteristics of the image. The one or more categories may be predefined, such that the image analysis engine can be configured in advance to determine the one or more characteristics in order to assign the image to a classification in each of the one or more categories. The image analysis engine may classify the image in each category of the one or more categories based on the one or more characteristics, such as according to a dominant, primary, and/or most relevant characteristic in each category. The image analysis engine may determine each classification of one or more classifications of the image from a different predefined category.

In another embodiment, the image analysis engine may determine each characteristic of a plurality of characteristics of the image from a different predefined category. Each characteristic of the plurality of characteristics of the image may be determined for a different predefined category and the image analysis engine can then classify the image in each category based on the determined characteristic for that category.

In still another embodiment, the image analysis engine may include one or more categories (i.e. categories of classifications) each including or otherwise organizing multiple classifications, and may assign an image to a classification within a category by evaluating characteristics of the image. The categories of classifications may be predefined, such that the image analysis engine can be configured in advance to assign the image to a classification in each category. The image analysis engine may assign the image a classification in each category of the one or more categories based on a plurality of characteristics, such as according to a dominant, primary, and/or most relevant characteristic, according to the category. Stated otherwise, the image analysis engine may determine each classification of a plurality of classifications of the image from a different predefined category. Each classification of the plurality of classifications of the image may be determined for a different predefined category. The image analysis engine may classify the image in each category based on the plurality of characteristics, such as according to a dominant, primary, and/or most relevant characteristic in the category.

For example, the image analysis engine may include categories such as an general image category (e.g., an overall image character category), an anatomic sublocation category, a tissue category, and a procedure category. The image analysis engine may determine one or more characteristics in each of these categories and classify the image in each category according to the one or more characteristics within that category. As a part of the example, with respect to the general image category, the image analysis engine may determine an extent to which the image includes one or more of the following characteristics: air (e.g., a bubble, or presence of air, such as within a liquid viewing medium); out of focus; cloudy; bloody; out of body; and good. The image analysis engine may further classify the image within the general image category according to the one or more characteristics. In some instances the image analysis engine may determine a plurality of characteristics in the general image category and classify the image in the general image category based on the plurality characteristics, such as according to a dominant, primary, and/or most relevant characteristic in the category. The image analysis engine may be able to determine if, for example, the image has a characteristic of appearing bloody and if the bloody characteristic is a dominant, primary, and/or most relevant characteristic in the general image category.

The potential characteristics of an image sought for by an image analysis engine for a given category (and the potential classifications of an image within the given category) may be constrained based on a classification of the image in another category. For example, the image analysis engine may include multiple categories of characteristics, including an anatomic sublocation category. The image analysis engine may determine an image has a characteristic of being a view in a medial compartment of a knee and thereby classify the image as "medial compartment of knee" within the anatomic sublocation category. Based on this classification of the image as being a medial compartment of a knee according to the anatomic sublocation category, the characteristics sought for (and thereby the classifications available) within the tissue category may be constrained. Because the image analysis engine classified the image as a view within a medial compartment of a knee, the characteristics within the tissue category may be limited to medial femoral condyle, medial meniscus, and medial tibia, and thereby be constrained to exclude other tissue characteristics sought for by the image analysis engine with respect to the tissue category that might be in other anatomic sublocations.

In some embodiments, the image analysis engine receives image data, such as raw image data or video data, and then converts the image data to a digital image format. For example, each frame of video data may be converted to an image that the image analysis engine can analyze to determine one or more characteristics of the image (or the view in the image).

The control engine is to control the medium management system based on the characteristics of the image. As described above, the medium management system may include one or more components controlling one or more of: delivery of a medium to an area being visualized, outflow of a medium from an area being visualized, outflow of a medium through a mechanical device, outflow of a medium through an energy device, and any combination of one or more of the foregoing. In some embodiments, the control engine may provide control to the medium management system by directing instructions or commands to one or more components of the medium management system. In some embodiments, the control engine controls or otherwise adjusts the medium management system based on one or more characteristics of the image to one of: increase one or more of pressure in the area to be visualized and flow of viewing medium into (and possibly out of) the area to be visualized; decrease one or more of pressure in the area to be visualized and flow of viewing medium into (and possibly out of) the area to be visualized; and make no change to existing settings.

In some embodiments, the control engine may adjust or otherwise provide parameters to the medium management system. For example, the control engine may provide one or more of a target pressure parameter and target flow to one or more components of the medium management system, which may be a pressure to which the medium management system will strive to achieve, by adjusting a combination of inflow and/or outflow at the area to be visualized such that the actual pressure trends toward the target pressure with a target flow rate and/or range of flows. In some embodiments, the control engine may control or otherwise adjust the medium management system based on one or more characteristics of the image to one of: increase one or more of a target pressure in the area to be visualized and target flow of viewing medium into (and possibly out of) the area to be visualized; decrease one or more of pressure in the area to be visualized and flow of viewing medium into (and possibly out of) the area to be visualized; and make no change to one or more of a target pressure parameter and a target flow parameter.

In some embodiments, the control engine may control or otherwise adjust the medium management system based on a characteristic of the image until the characteristic changes.

In some embodiments, the functionality of the image analysis engine and the control engine may be combined into a single functional unit (e.g., an endoscopic image analysis system or an image analysis component). For example, one or more of endoscopic images, environmental data, and system state data can be inputs into the single functional unit. Outputs of the single functional unit can be adjustments to one or more medium delivery device(s) in the above sample embodiments, or to any other component of an endoscopic system.

As can be appreciated, the control engine may be able to adjust one or more components of the endoscopic surgical system in addition to the medium management system, based on the characteristics of the image, as will be described more fully herein.

A system for performing an endoscopic procedure, according to another embodiment may include an endoscope, a camera (or other imager), an image analysis component (including an image analysis engine and any control engine), and one or more other components (e.g., implements, tools, instruments) of an endoscopic system. The system enables a procedure team to perform an endoscopic procedure and the various components can play a role in such a procedure. As can be appreciated, the system may include additional components that are known to persons of ordinary skill, such as a display monitor, a content management system, a tower, and the like.

The endoscope, camera, may be identical, similar, or otherwise analogous to the endoscope and camera described above. The image analysis component may include an image analysis engine and control engine that may be identical, similar, or otherwise analogous to the image analysis engine and control engine described above.

The one or more other components of the endoscopic system may include, but are not limited to, one or more of: a light source, the camera, a motorized instrument (e.g., shaver, suction, saw, drill), an energy device (e.g., electrocautery tool, laser device), a delivery device (e.g., syringe infusion pump), and any other device that may be appropriate and/or useful during an endoscopic procedure.

The control engine is to control the one or more other components of the endoscopic system based on one or more characteristics of the image. In some embodiments, the control engine may provide control to one or more of the other components of the endoscopic system by providing instructions or commands. In some embodiments, the control engine automatically controls each of the other components of the endoscopic system individually and/or separately (e.g., from other components of the endoscopic system).

In some embodiments, the control engine controls or otherwise adjusts the one or more other components of the endoscopic system by adjusting or otherwise providing parameters. In some embodiments, the control engine may control or otherwise adjust a medium management system based on a characteristic of the image until the characteristic changes. In some embodiments, the control engine controls or otherwise adjusts the one or more other components of the endoscopic system based on a plurality of characteristics. In some embodiments, the control engine controls or otherwise adjusts the one or more other components of the endoscopic system based on a classification of an image.

Examples of embodiments of the present disclosure are described below with reference to the drawings and in a context of arthroscopy, and it can be appreciated that the systems, methods, and techniques of these embodiments can extend to endoscopy generally and any form or field of endoscopy specifically. An endoscopic application (e.g., surgery, procedure) that includes use of a scope can be enhanced by embodiments of the present disclosure to include analysis of images and/or the environment during an endoscopic procedure to automatically adjust one or more aspects of an endoscopic system in order to optimize the utility of the image, both during and after the procedure.

FIG. 1 is a view of an endoscopic system 100, according to one embodiment of the present disclosure, in an operating room or a procedure room. The endoscopic system 100 can include an endoscope 102, a camera 104 (or other imager), a scope cannula 106, an outflow cannula 107, a light cord 108 (from a light source 116), and a tower 110 that includes one or more other components, including a display 112 (in this illustrated embodiment a primary display screen 112a and a secondary display screen 112b), an image processing component 114, an image analysis component 150 (including an image analysis engine and a control engine), a light source 116, a motorized instrument component 118 (coupled to a shaver 118a, in FIG. 1), a medium management system 120 (including one or both of a medium delivery device 120a and an outflow control device 120b), an energy instrument component 122 (e.g., an electrocautery instrument, laser), a content management system (CMS) 124, and a printer 126. The endoscopic system 100 can include one or more other components (e.g., implements, tools, instruments), as known in art. For example, an irrigation tower 142 can hold bags of fluid used in arthroscopy. As an additional example, a user 10 (e.g., surgeon, member of a procedure team) is shown utilizing an instrument 132 (e.g., a probe) in the right hand. The endoscopic system 100 enables the user 10 and/or a procedure team to perform an endoscopic procedure and the various components can play a role in such a procedure. A user and/or procedure team may utilize the endoscopic system 100 to perform one or more procedures during a case. A case may be the activities and process (or everything) relating to performing one or more medical tasks utilizing an endoscopic system related to a single episode for a single patient. A procedure is something done during a case and can be diagnostic (e.g., looking at things to make a diagnosis, whether normal structures or abnormal) or therapeutic/procedural (e.g., performing an action). Though sometimes herein the term case and procedure may be used interchangeably, a case can actually comprise one or more procedures.

The endoscope 102 of FIG. 1 provides the user 10 and/or the procedure team a view of an area (e.g., one or more structures) to be visualized that is inside the knee of the patient and that is within a field of vision of the endoscope. The camera 104 captures image data of the area to be visualized (inside the patient's knee). The endoscope 102, the camera 104, and the scope cannula 106 are portrayed in a detailed and partially exploded view, as well as in the left hand of the user 10 of the endoscopic system 100. The detailed, partially exploded view illustrates one example of positioning of the camera 104 relative to the endoscope 102, which passes through the scope cannula 106. The scope cannula 106 is also connected to the medium management system 120 and provides for inflow of fluid. The user 10 is shown manually manipulating the endoscope 102 (inserted within the scope cannula 106) and the camera 104 to access (e.g., view) an area within the body (e.g., knee) of the patient that is being addressed. The pictured endoscope 102 is an example of a type of endoscope that may be used in arthroscopy, and other embodiments of endoscopes are within the scope of the present disclosure.

The tower 110 provides a support structure for several components of the endoscopic system 100, including the display 112, the image analysis component 150, the image processing component 114, the light source 116, the motorized instrument component 118, the medium management system 120, the energy instrument component 122, the content management system (CMS) 124, and the printer 126. The tower 110 may be portable or otherwise moveable, being mounted or otherwise disposed on a wheeled cart 140. In other embodiments the tower can be attached to a boom or otherwise generally fixed to a structure in an operating or procedure room. The tower 110 is generally nonsterile, such that anything that is plugged into a component of the tower 110, or any buttons that need to be pressed on the components of the tower 110 has to be done by a member of the procedure team who is not scrubbed into the procedure (e.g., a circulating nurse in the room). Some of the components drive or otherwise power instruments used by the procedure team (e.g., the light source 116 provides light through the light cord 108 to the endoscope 102, the motorized instrument component 118 drives or otherwise powers the shaver 118a, the energy instrument component 122 drives or otherwise powers an electrocautery instrument). The components disposed on the tower 110 can be varied, according to the needs and objectives of various forms of endoscopic procedures and the preferences of the procedure teams performing such.

The image processing component 114 processes the image data from the camera 104 for presentation on the display 112 (e.g., the primary display 112a). The presentation on the display 112 of the area being visualized allows the user 10 to see the area to be addressed (e.g., within the knee of the patient) as well as any tool or instrument that the user 10 may be manipulating (e.g., the instrument 132) in order to diagnose and/or treat a condition at the area to be addressed.

The light source 116 provides a source of light through the light cord 108 to the endoscope. In times past, the light source 116 included halogen bulbs, like in a theater projection. Presently, the light source 116 generally includes light emitting diode (LED) sources. The light cord 108 is generally a fiber optic cord. A user interface (e.g., with a menu, buttons, switches, and the like) enables activation and/or adjustment to the light source 116. There may be a "standby" button that turns off the light source 116 so the drapes don't get burned if the endoscope 102 is left directed on them for too long. The light source 116 can be controlled remotely, in some embodiments, such as by a button on the camera 104 to toggle the light source 116 off/on. There may be communication between the light source 116 and the camera 104 to enable interoperability.

The motorized instrument component 118 supplies power to various instruments, such as the shaver 118a and other motorized instruments. The motorized instrument component 118 may sense which attachment is in a hand tool (e.g., shaver, burr, etc.) and may display a default rotations per minute (RPM) measurement (e.g., on a display above a corresponding connection port). If the user 10 changes modes, the mode or change may be displayed. A foot control 134 may be connected to allow the user 10 to operate a connected motorized instrument, thus freeing the user 10 from using a hand to control the instrument. The foot control 134 may allow for control of a motorized instrument (e.g., forward, oscillate, reverse, etc.) and may allow for variable speeds. The motorized instrument component 118 may supply power to or otherwise drive multiple instruments at a time.

The medium management system 120 is generally to manage a viewing medium (e.g., generally a fluid that is a liquid or gas) in the area to be addressed (and/or the area to be visualized). The viewing medium can be used to provide, enable and/or enhance a view through the endoscope 102 at the area to be addressed. Clear viewing medium (e.g., clean, debris-free) provides preferable viewing at the area to be addressed. If the viewing medium becomes cloudy or bloody, the medium management system 120 can increase pressure and/or flow of the viewing medium to clear the debris or blood. The pressure and/or flow of the viewing medium can be adjusted to slow bleeding. Depending on a quality (e.g., one or more characteristics indicating lower quality) of the view through the endoscope 102 and image data thereof, the medium management system 120 may be used to increase one or more of pressure of viewing medium in the area to be visualized and flow of viewing medium into and/or out of the area to be visualized to enhance the quality of the view. Similarly, depending on a quality (e.g., one or more characteristics indicating high quality) of the view through the endoscope 102 and image data thereof, the medium management system 120 may be used to decrease one or more of pressure of viewing medium in the area to be visualized (e.g., to reduce extravasation and potentially improve a patient's outcome) and flow of viewing medium into and/or out of the area to be visualized (e.g. to reduce a quantity of viewing medium) while maintaining the high quality view.

In the illustrated endoscopic system 100 of FIG. 1, the medium management system 120 includes both a medium delivery device 120a (e.g. inflow pump) to provide inflow of viewing medium and an outflow control device 120b (e.g. outflow pump) to control outflow of viewing medium at the area being addressed. FIG. 1 provides an enlarged detailed view of the medium management system 120, including the medium delivery device 120a and the outflow control device 120b. In the illustrated embodiment of FIG. 1, the medium delivery device 120a comprises an inflow pump to deliver a liquid viewing medium and adjust flow of the liquid as needed to affect pressure and the outflow control device 120b comprises an outflow pump to suction or otherwise control the outflow of the liquid viewing medium. A medium management display 121 on the medium management system 120 can present parameters, measurements (or readings), and/or settings of the medium management system 120 and/or viewing medium. In some embodiments, the medium management display 121 is touch sensitive and can be used by a non-sterile user to adjust various parameters of the medium management system 120. Different embodiments of medium management systems generally enable adjustment of parameters through one or more of, but not limited to, the following: a touch screen, one or more buttons on a non-sterile component, a foot control, a hand control in the sterile field, and a control on a shaver or other attached device. For example, a target pressure and target flow are parameters that may be used by the medium management system 120 as targets to which to strive, such as by pumping fluid in and/or out of the area to be addressed to direct the actual pressure and/or actual flow toward the respective targets. As another example, actual pressure and actual flow may be measurements or readings that are provided for the user 10. As another example, settings, such as viewing medium temperature, delivery or outflow protocols, and the like can also be presented to the user 10. As described above, flow and pressure of the liquid viewing medium can be adjusted to enhance the view of the endoscope 102 (and thereby the image data collected by the camera 104) and presented on the medium management display 121 for the user 10 and procedure team. As can be appreciated, the medium management system 120 can be used to increase pressure of viewing medium in the area to be visualized and/or flow of viewing medium into and/or out of the area to be visualized to clear a cloudy view or a bloody view. The medium management system 120 can be used to increase pressure of the viewing medium in the area to be visualized to slow bleeding. When the view quality is high, utilizing the medium management system 120 to gradually decrease pressure in the area to be visualized and flow of viewing medium into and out of the area to be visualized can reduce a quantity of viewing medium used during a procedure and potentially extravasation, which can improve the outcome of the procedure. The parameters, measurements, and/or settings of the medium management system 120 can achieve desired pressure and/or flow of viewing medium and the medium management display 121 can indicate to the user 10 this information.

If both pressure and flow are changed (ie. to clear a bloody field), they are generally changed in the same direction (e.g. both increased to control the bleeding and both decreased when the image improves). As a more specific example of usage of the medium management system 120, the same result could be accomplished by making changes to pressure and flow in opposite directions. If an image is bloody, for example, the user 10 could increase the pressure 11 mm Hg and decrease the flow by 5 ml/min. Two seconds later, the user 10 could then decrease the pressure 1 mm Hg and increase the flow by 105 ml/min. Overall, this would effectively increase pressure 10 mm Hg and increase the flow 100 ml/min.

In some embodiments 120, the medium management system 120 may be integrated with one or more other components of the endoscopic system (e.g., suction integrated with a motorized implement). In some embodiments, a medium management system 120 may comprise only one of a medium delivery device or an outflow control device. In an embodiment having only a medium delivery device, the medium management system 120 may control or otherwise manage delivery of viewing medium through an inflow cannula (e.g., generally the scope cannula 106) and outflow may occur through another instrument, such as a shaver 118a with integrated suction, or relatively passively (or without direct control) through an outflow cannula 107. In an embodiment having only an outflow control device, viewing medium may be provided passively, such as by gravity (e.g., a hanging fluid bag) and the medium management system 120 may simply control or otherwise manage the outflow of viewing medium.

As will be described more fully, the control engine of the image analysis component 150 can provide commands or other signals to the medium management system 120 in which both the medium delivery device 120a and the outflow control device 120b are combined to direct or otherwise influence flow and/or pressure at the area to be addressed. As can also be appreciated, in other embodiments the medium management system 120 may include only one of a medium delivery device (e.g. an inflow pump) or an outflow control device (e.g., an outflow pump, a tool or instrument integrating suction, such as a shaver component or an electrocautery component). The control engine can provide commands or other signals to the medium management system 120 to direct or otherwise influence flow and/or pressure at the area to be addressed.

The energy instrument component 122 can drive or otherwise power an energy delivery instrument such as an electrocautery instrument, a laser, an argon beam coagulator, or the like. An energy delivery instrument is used to deliver energy to tissue, for example, to coagulate bleeding, to cauterize, to ablate tissue, etc. Ultimately, these energy delivery instruments basically create heat, which performs the function. In some embodiments, an energy delivery instrument also integrates suction, in which case control of the medium passing through the device follows the same discussion as above.

An electrocautery instrument is an energy delivery instrument that uses a probe that touches or comes close to the tissue to transfer heat to the tissue and through which electricity in different forms is passed. An electrocautery instrument can be monopolar, in which case a grounding pad is applied to the patient to complete the circuit. An electrocautery instrument can be bipolar, in which two electrodes are placed in proximity on the instrument itself to complete the circuit.

An argon beam coagulation instrument is an energy delivery instrument that is in some respects a "non-contact" form of electrocautery. The argon beam coagulation instrument passes a thin stream of argon out the end of the instrument, ionizes the argon with a high-voltage circuit, and the argon carries the electrical charge to the tissue. The patient has a grounding pad to complete the circuit.

A laser instrument is an energy delivery instrument that, instead of electricity, uses a laser to deliver energy to tissue. The differences are in frequency of the light, power, pulsation, etc. Ultimately, a laser instrument also heats up the tissue to accomplish a goal.

The energy instrument component 122 can comprise a box on the tower 110 into which an energy delivery instrument connects and that drives or otherwise powers the energy delivery instrument. The energy instrument component 122 can provide settings and can otherwise configure operation of the energy delivery instrument.

The content management system (CMS) 124 can provide an operating platform and/or otherwise interconnect the components of the tower 110. The CMS 124 can be considered, in essence, what makes the tower 110 operable. While many other components of the tower 110 are interchangeable with other forms and types of components, the CMS 124 is an operator or "brains" of the tower 110. For example, the CMS 124 may be powered by, operate on, or otherwise comprise an operating system, such as Windows®, Linux®, iOS®. In some embodiments, the CMS 124 may be effectively a Windows PC, booting into Windows and autorunning a program for bringing the tower online (or operational). The monitor for the CMS 124 (or computer) may be the secondary screen 112b on a boom. A keyboard and/or other input device(s) may be disposed on the tower 110 to receive user input. In some embodiments, the CMS 124 may provide functionality to record segments of video or capture images from the camera 104. In some embodiments, the CMS 124 may provide functionality to print images on the printer 126 and/or export data (e.g., to a USB port). In some embodiments, the CMS 124 may facilitate pushing images and/or video to an electronic medical record (EMR).

The image analysis component 150 can analyze one or more images of a view provided by the endoscope 102 and can, based on that analysis, affect one or more components of the endoscopic system 100 and/or enhance the utility of information of the endoscopic system 100. The image analysis component 150 receives image data (or one or more images from the image data) from the camera 104 or from the image processing component 114 and analyzes or otherwise evaluates one or more images to determine a characteristic and/or classification of the one or more images. The characteristic and/or classification of the one or more images may be provided to a control engine of the image analysis component 150, which can generate a command or otherwise control the medium management system 120 and/or one or more other components of the endoscopic system 100 based on the determined characteristic and/or classification. For example, the image analysis engine of the image analysis component 150 may analyze one or more images and determine that the one or more images are bloody. A bloody view is a view that can be improved or otherwise enhanced to allow the user 10 and/or procedure team better ability to see and/or understand the area to be addressed, where the instruments are within the area to be addressed, and/or to see and understand what the instruments are doing within the body of the patient at the area being addressed. A bloody view can be improved or otherwise enhanced by increasing fluid flow to flush out blood and/or fluid pressure to slow additional bleeding at the area being addressed. The control engine of the image analysis component 150 can provide commands or parameters to the medium management system 120 to increase a target flow and/or target pressure, which can result in the medium management system increasing the flow of viewing medium and/or pressure at the area being addressed. In this manner, the image analysis component 150 (and/or control engine thereof) automatically control components of the endoscopic system 100, thereby relieving the user 10 or one or more other persons of a procedure team from diverting attention or resources (e.g., a hand, a foot) to manually adjust such components.

The image analysis component 150 can also enhance operation of the endoscopic system 100 by enhancing the utility of the image data obtained via the camera 104. Additional information relating to a procedure can be provided by the image analysis component 150 to a display 112 for presentation to the user 10. The additional information obtained by the image analysis component 150 can be included with image data for presentation on the primary display 112a utilizing unused space (e.g. on the sides of a circular endoscopic image displayed on a rectangular screen) and/or on the secondary display 112b. This additional information can include, but is not limited to, one or more of: results of analysis of image characteristics, state data from other components of the endoscopic system, data received from sources generally considered external to the endoscopic system (e.g. blood pressure, heart rate, room temperature), adjustments made (e.g. by a member of the procedure team) to the medium management system and/or any other component of the endoscopic system, comparisons of any type of current procedure information with one or more other procedures (e.g. elapsed times compared to other similar cases, pressure comparisons), and any other data used by or generated by the image analysis component 150.

Figure 2:
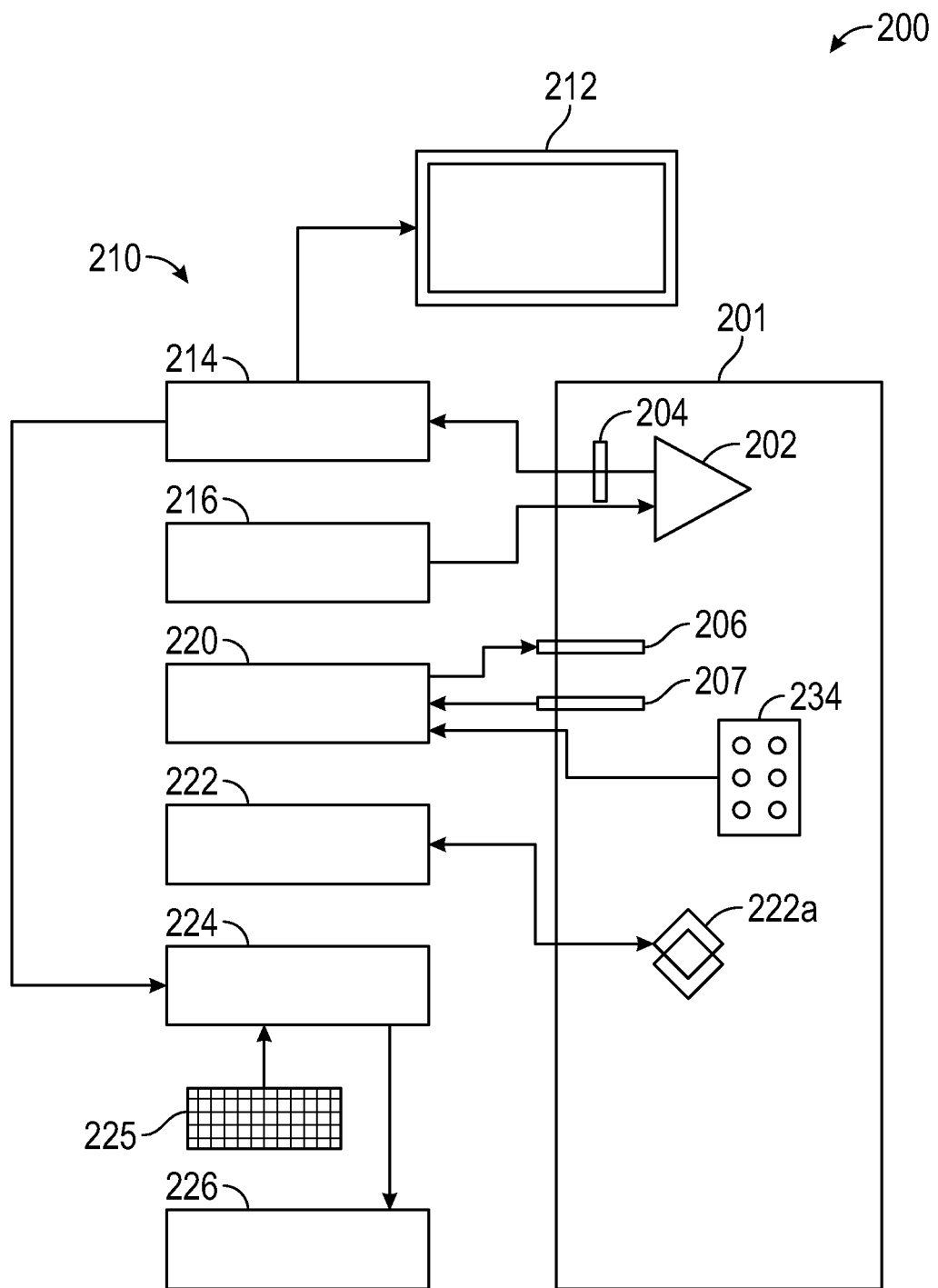
FIG. 2 is a schematic block diagram of an endoscopic system.

FIG. 2 is a schematic block diagram of a traditional endoscopic system 200, such as may be used in arthroscopy, a particular form of endoscopy. A sterile field 201 is indicated for reference to illustrate components or portions of the traditional endoscopic system 200 typically in the sterile field 201. (The components outside the sterile field 201 are typically, although not necessarily, contained in a tower 210, similar to the tower 110 of FIG. 1). The traditional endoscopic system 200 depicted in FIG. 2 includes an endoscope 202, a camera 204 (or other imager), an inflow cannula 206 (may also be a scope cannula), an outflow cannula 207, and one or more other components including components typically contained in a tower 210, which can include a display 212, an image processing unit 214, a light source 216, a medium management system 220 (including one or both of a medium delivery device and an outflow control device), one or more additional instrument components 222 (e.g., a motorized instrument component, an energy delivery component) to drive or otherwise power one or more instruments 222a, a content management system 224 and associated input device(s) 225 (e.g., a keyboard) and output devices 226 (e.g., printer, USB port, optical disc drive/burner, secondary display).

The endoscope 202 either transmits an image to the camera 204 or else captures image data via an imager of a chip-on-tip format. The raw image data captured is sent to an image processing unit 214 where it is processed into a format suitable for viewing on the display 212 (e.g. high-definition multimedia interface (HDMI), digital visual interface (DVI)) to which it is connected.

The light source 216 is generally attached to the endoscope 202 to illuminate the area being viewed and to be visualized on the display. Typically, light is transmitted from the light source 216 to the endoscope 202 (e.g., via a light cord), but in some endoscopic systems the light source 216 itself is attached directly to the endoscope 202. In some traditional endoscopic systems 200, some limited manual control of the light source 216 is possible through a button on the camera (e.g. to toggle the light source on or off).

Most traditional endoscopic systems 200 used for arthroscopy include a medium management system 220 in the form of one or more pumps that can provide a liquid medium to an area being addressed through an inflow cannula 206 and/or can control outflow of the medium, such as at an outflow cannula 207. In some systems, the inflow cannula 206 and/or outflow may be separate cannulas or access points, while in other systems the inflow and/or outflow may be integrated into other instruments (e.g. in arthroscopy in which the inflow attaches to the same scope cannula in which an endoscope is placed). In some systems, the medium management system 220 may only control one of the inflow or the outflow, and the other may be managed manually (e.g. adjusting a stop cock, pinching an outflow tube).

A goal of most medium management systems 220 is to adjust flow to maintain a set target pressure as set by a user. There is often a manual control 234 with one or more buttons on it on the sterile field 201 accessible by the user and/or a member of the procedure team. This manual control 234 may be a hand control (i.e., operated by hand) or a foot control (i.e., operated by foot) that allows for manual adjustments to be made to target pressures and/or target flows. Manual controls 234 also often have buttons which a user can press to manually enable preset and temporary changes to parameters on a medium management system. For example, a "wash" function might increase the flow and/or pressure a set amount for 60 seconds, after which the settings return to previous values, regardless of whether or not it affected any change to the image. Stated otherwise, one or more members of the team can use the manual control 234 to attempt to manually adjust the medium management system 220 to enhance the viewing medium to optimize the image on the display 212.

Most traditional endoscopic systems also include one or more additional instrument components 222 which are connected to various instruments 222a in the sterile field 201. Some examples of these include, but are not limited to: a mechanical device component, which controls one or more mechanical instruments (e.g. shaver, burr, saw); and an energy device component, which controls one or more energy delivery instruments (e.g. electrocautery, laser, argon beam coagulator). While only one instrument component 222 is shown in FIG. 2, this represents one or more components with their associated instruments 222a. In some traditional endoscopic systems 200, there is limited communication between one or more of these other instrument components 222 and the medium management system 220. For example, in some endoscopic systems 220, when a motorized instrument such as a shaver is used, the medium management system 220 assumes that outflow will be through the shaver and stops outflow through another outflow path, whether or not outflow is actually going through the shaver.

The content management system 224 is in electrical communication with the image processing component 214. At the beginning of a case (e.g., a procedure or surgery), a member of the procedure team typically enters patient information into the content management system 224 using an attached keyboard 225 or other input device. During a procedure, typically when the user presses a button on the camera 202, the content management system 224 effectively performs a screen capture function of whatever image is being shown by the image processing component 214 on the display 212. With typical content management systems, a user can record video for future review with a toggle to start recording and stop recording. One or more images and/or videos can therefore be saved throughout the procedure and attached to the patient chart or EMR or otherwise associated with the patient name previously entered at the beginning of the case. At the conclusion of the case, most traditional endoscopic systems 200 are configured to print any images saved by the content management system 224 on an attached printer 226.

As is evident and briefly mentioned, the traditional endoscopic system 220 has minimal to no communication between components (maybe with the exception of the content management system 224). The traditional endoscopic system 200 does little to no processing of image data acquired by the camera 204 other than to format for presentation on the display 212 or to perform a crude autoshutter function based on brightness of the overall image. While some systems allow for selection of user preferences at the beginning of a case, there is little to no automation of any configuration, settings, or parameters of any components of the traditional endoscopic system 200 based on an evaluation or analysis of image data and/or the quality of an image viewable by the user or procedure team. The traditional endoscopic system 200 also provides limited utility of the image data gathered by the camera 204 beyond simply displaying it for the user(s) and allowing for capture or individual images and/or video, and does little or nothing to enhance or leverage the image data. The present inventor recognized the desirability to automate aspects of an endoscopic system and otherwise affect operation and/or components of an endoscopic system to enhance the procedure and experience of the user and procedure team, thereby increasing probability of a favorable patient outcome.

Figure 3:
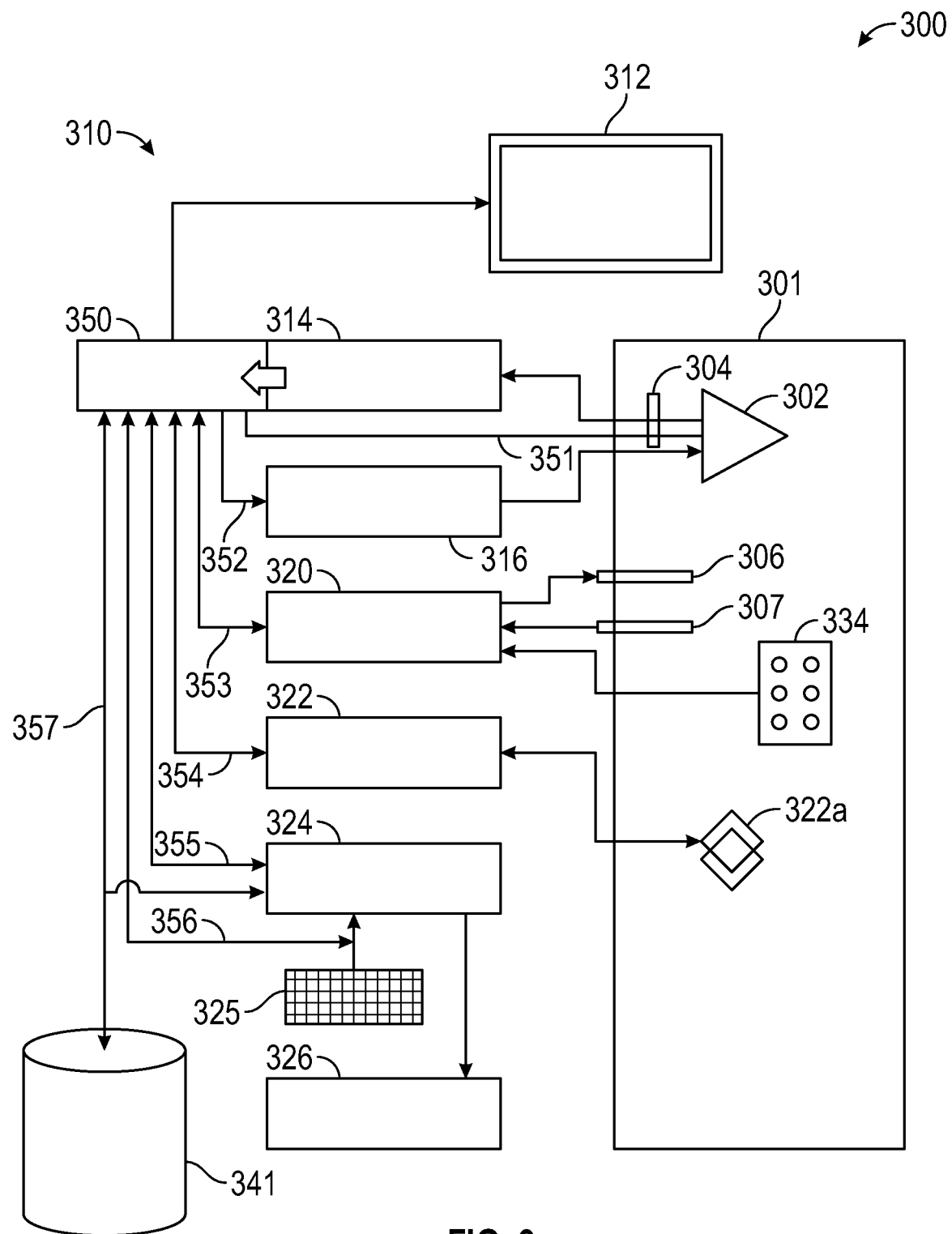
FIG. 3 is a schematic block diagram of an endoscopic system, according to one embodiment of the present disclosure.

FIG. 3 is a schematic block diagram of an endoscopic system 300, according to one embodiment of the present disclosure. The endoscopic system 300 comprises an endoscopic image analysis system, according to one embodiment of the present disclosure, in the form of an image analysis component 350. The depicted endoscopic system 300 may be of a type used in arthroscopy, a particular form of endoscopy, and additionally shows one example of how the image analysis component 350 can be integrated into the endoscopic system 300.

The endoscopic system 300 depicted in FIG. 3 is similar or analogous to the traditional endoscopic system 200 depicted in FIG. 2 and similarly includes an endoscope 302, a camera 304 (or other imager), an inflow cannula 306 (which may also be a scope cannula), an outflow cannula 307, and one or more other components including components typically contained in a tower 310, which can include a display 312, an image processing unit 314, a light source 316, a medium management system 320 (including one or both of a medium delivery device and an outflow control device), one or more additional instrument components 322 (e.g., a motorized instrument component, an energy delivery component) to drive or otherwise power one or more instruments 322a, and a content management system 324 and associated input device(s) 325 (e.g., a keyboard) and output devices 326 (e.g., printer, USB port, optical disc drive/burner). A manual control 334 can enable a user to manually (e.g., by hand or by foot) control one or more of the components of the endoscopic system 300. These components and the features thereof may be identical, similar, or analogous to those components of FIG. 2, and discussion of the same will not be repeated for sake of brevity. A sterile field 301 is indicated in FIG. 3, similar to FIG. 2, for reference to illustrate components or portions of the endoscopic system 300 that may typically be in the sterile field 301. (The components outside the sterile field 301 may be typically, although not necessarily, contained in a tower 310, similar to the tower 110 of FIG. 1). In the embodiment of FIG. 3, the endoscopic system 300 is different from and improved over traditional endoscopic systems by inclusion of the image analysis component 350.

The image analysis component 350 can receive endoscopic image data from the image processing component 314. The image analysis component 350 can analyze one or more images of a view provided by the endoscope 302 and can, based on that analysis, affect one or more components of the endoscopic system 300. The image analysis component 350 alternatively or in addition can enhance the utility of information of the endoscopic system 300. The image analysis component 350 can receive image data, or one or more images from the image data, from the camera 304 or from the image processing component 314. An image analysis engine of the image analysis component 350 can analyze or otherwise evaluate one or more images to determine a characteristic and/or classification of the one or more images. The characteristic and/or classification of the one or more images may be provided to a control engine of the image analysis component 350, which can generate a command or otherwise control the medium management system 320 and/or one or more other components of the endoscopic system 300 based on the determined characteristic and/or classification.

In some embodiments, the image analysis component 350 may also receive state data 352-355 from one or more of the other components (e.g., image processing component 314, light source 316, medium management system 320, instrument component(s) 322, content management system 324). In some embodiments, the image analysis component 350 may also receive input data 356 such as from an input device 325 and/or via another component (e.g., display 312, image processing component 314, light source 316, medium management system 320, instrument component(s), content management system 324). In some embodiments, the image analysis component 350 can additionally receive external data from outside sources. The image analysis component 350 can control or otherwise make adjustments to one or more other components of the endoscopic system based on this state data 352-355, input data 356, and any external data received.

The image analysis component 350 might affect the camera 304, if the image analysis component 350 determines that an image is primarily out-of-focus, by sending an appropriate signal 351 to the camera 304 to adjust the focus. The image analysis component 350 might affect the light source 316, if the image analysis component 350 determines that the endoscope 302 has been removed from a patient, by sending a signal to the light source 316 to put it on standby to thereby reduce risk of burns and/or fires. (A light source 316 focused through the end of the endoscope 302 can have enough energy to cause damage and burns.) If the image analysis component 350 determines that an adjustment to the light source 316 may optimize the utility of an image, the image analysis component 350 can communicate an appropriate signal to the light source 316 (e.g. automatically adjusting brightness, changing frequency and/or temperature).

The image analysis component 350 can also affect the medium management system 320. For example, if the image analysis component 350 determines that an image is bloody, the control engine of the image analysis component 350 can send a command to the medium management system 320 to increase a target pressure and a target flow of the viewing medium. If the image analysis component 350 determines that an image is cloudy, the control engine can send a command 354 to the medium management system 320 to increase a target flow of the viewing medium (and not the target pressure). If the image analysis component 350 determines that an image is good, the control engine can send commands to the medium management system 320 to decrease the target pressure and/or the target flow of the viewing medium to reduce them to a lower level, as long as the image remains good, to thereby help reduce extravasation of the viewing medium into surrounding tissues and to reduce viewing medium consumption. As another example, if the image analysis component 350 determines that the endoscope 302 has been removed from the patient, the control engine of the image analysis component 350 can send a command to the medium management system 320 to stop all flow of the viewing medium.

While the image analysis component 350 can automatically adjust target parameters of a medium management system 320, the user can remain in complete control of the viewing medium. Minimum and maximum allowable parameters for the automatic adjustments can be set by the user and can be shown on the display 312. The current settings can be displayed, as well as any adjustments made by the image analysis component 350. Additionally, the user may still have the same control of the endoscopic system 300 as in a traditional endoscopic system, by using a manual control 334 attached to the medium management system 320. In order to improve the function of the image analysis component 350, any adjustments made by the user using the manual control 334 can be captured as training data.

In some embodiments, the image analysis component 350 can also control the one or more instrument components 322 of the endoscopic system 300. One example of this is adjusting power settings on an energy delivery instrument component 322 depending on determination of an anatomic location. Another example is automatically adjusting modes and/or RPM settings on a mechanical instrument component 322 based on various characteristics of an image. As another example, some instruments have suction integrated and the image analysis component 350 can coordinate the outflow through the instrument suction with any outflow device of the medium management system 320 to maintain a good image. Another example is control of a delivery component based on an image (e.g. adjusting contrast delivered through a syringe to just enough to provide an adequate image).

In some embodiments, the image analysis component 350 can communicate 355 with a content management system 324. For example, the image analysis component 350 may communicate one or more determined characteristics of an image to the content management system 324. The content management system 324 can use the one or more characteristics to annotate images associated with a procedure that may be saved by a user of the endoscopic system 300 or other member of the procedure team. As a demonstrative example, the image analysis component 350 may determine a given image includes one or more of the following characteristics: "Medial Compartment of a Knee" as an anatomical sublocation, "Medial Meniscus Tear" as a diagnosis, and "Partial Medial Meniscectomy" as a procedure. The image can be saved and annotated with the annotations as follows: "Medial Compartment of a Knee" as an anatomical sublocation, "Medial Meniscus Tear" as a diagnosis, and "Partial Medial Meniscectomy" as a procedure. As with the medium management system 320, the user can review, revise, and otherwise control any annotations before saving them. Additionally, any changes made by the user to any annotations could be used as training data to improve algorithms for determining characteristics of an image.

Another example of how an image analysis component 350 can communicate 355 with a content management system 324 is where information (e.g., text information, bar codes, QR codes) pertaining to an endoscopic procedure is captured by the camera 304 (e.g., the same camera 304 from which image data is sent to the image analysis component 350). In this case, the image analysis component 350 can use optical character recognition (OCR) algorithms to extract pertinent information from the image data for use in or by the endoscopic system 300. Additionally, the image analysis component 350 can use decoding algorithms for bar codes, OR codes, and/or any other type of graphical representation of information to extract pertinent information for use in or by the endoscopic system 300.

Because there are alternate ways to get patient demographic information using an image analysis component 350, in legacy systems in which an appropriate interface is not possible, a jumper can be used between a keyboard 325 and a content management system 324 to auto-populate information and save users time. The jumper may allow mimicking keystrokes to enter information into such legacy systems.

While an important function of the image analysis component 350 is to control one or more components of the endoscopic system 300 during a single procedure, in some embodiments the image analysis component 350 can interact with other endoscopic systems beyond or outside of a single procedure for which it is used. A central datastore 341 may receive and store procedure data for the current procedure from the endoscopic system 300 and from other endoscopic systems. The central datastore 341 may make accessible to the image analysis component 350 procedure data for other procedures, including, but not limited to, one or more of the following: one or more other procedures using the same endoscopic system 300, one or more other endoscopic systems in a same facility, one or more facilities within a health system or geographical location, one or more electronic medical record systems, and a central repository containing information from a plurality of cases. There are several examples of functionality beyond controlling one or more endoscopic components in a single case, which are facilitated by the central datastore 341.

One example of functionality that is facilitated by the central datastore 341 is use of information associated with an image analysis system (e.g., image analysis component 350) as training data for iterative improvement. This can include, but is not limited to, one or more of the following: image data, state data, external data, procedure specific data, internal parameters relating to the function of the image analysis system, and manual adjustments and/or overrides made to the endoscopic system.

Another example of functionality that is facilitated by the central datastore 341 is where information that is captured is used for improvement, including but not limited to one or more of the following: input for algorithms to iteratively improve existing functionality of an image analysis system, input for algorithms to develop additional functions for an image analysis system, training data for machine learning and/or artificial intelligence algorithms in an image analysis system, input utilized to improve functionality and/or the experience for a single user of an endoscopic system, input utilized to improve functionality and/or the experience for multiple users of an endoscopic system and, input utilized to improve utility of an image analysis system, on a single device basis or in a larger aggregate system comprising two or more systems.

Another example of functionality facilitated by the central datastore 341 is where classification performed by an image analysis system is used to assist a user and/or a facility with documentation, including but not limited to one or more of the following: considering documentation to include, but not be limited to: images and/or videos for patients, users, facilities, EMRs, healthcare systems or any other entity, whether in printed or electronic form; textual documentation including, but not limited to, operative or procedural reports, procedure records, nursing records, or tracking records; or any printed or electronic format which can be accessed after a procedure; incorporation of diagnoses into said documentation; incorporation of procedures into said documentation; incorporation of tissue classification said categories into documentation; and, incorporation of implant information into said documentation.

Another example of functionality facilitated by the central datastore 341 is where data involved with use of an image analysis system for one or more procedures is used for aggregate reporting purposes, including but not limited to one or more of the following: using timing, diagnosis, procedure, tissue classification, implant, or any other classifiable information for purposes including, but not limited to: reporting, outcome studies, resource optimization, or utilization review; using parameters monitored and/or adjusted by the system including, but not limited to: pressure, flow, fluid used, time in different states, equipment used, vital signs, or procedures performed for purposes including, but not limited to: reporting, outcomes studies, resource optimization, or utilization review; making all such reporting capabilities available on any type of grouping including, but not limited to: a specific patient, location in the body, procedure, diagnosis, equipment used, user, facility, system, geographical region, or global level; and, comparing two or more types of grouping, whether such a comparison is performed and/or displayed during a procedure or whether performed following procedures.

Figure 4:
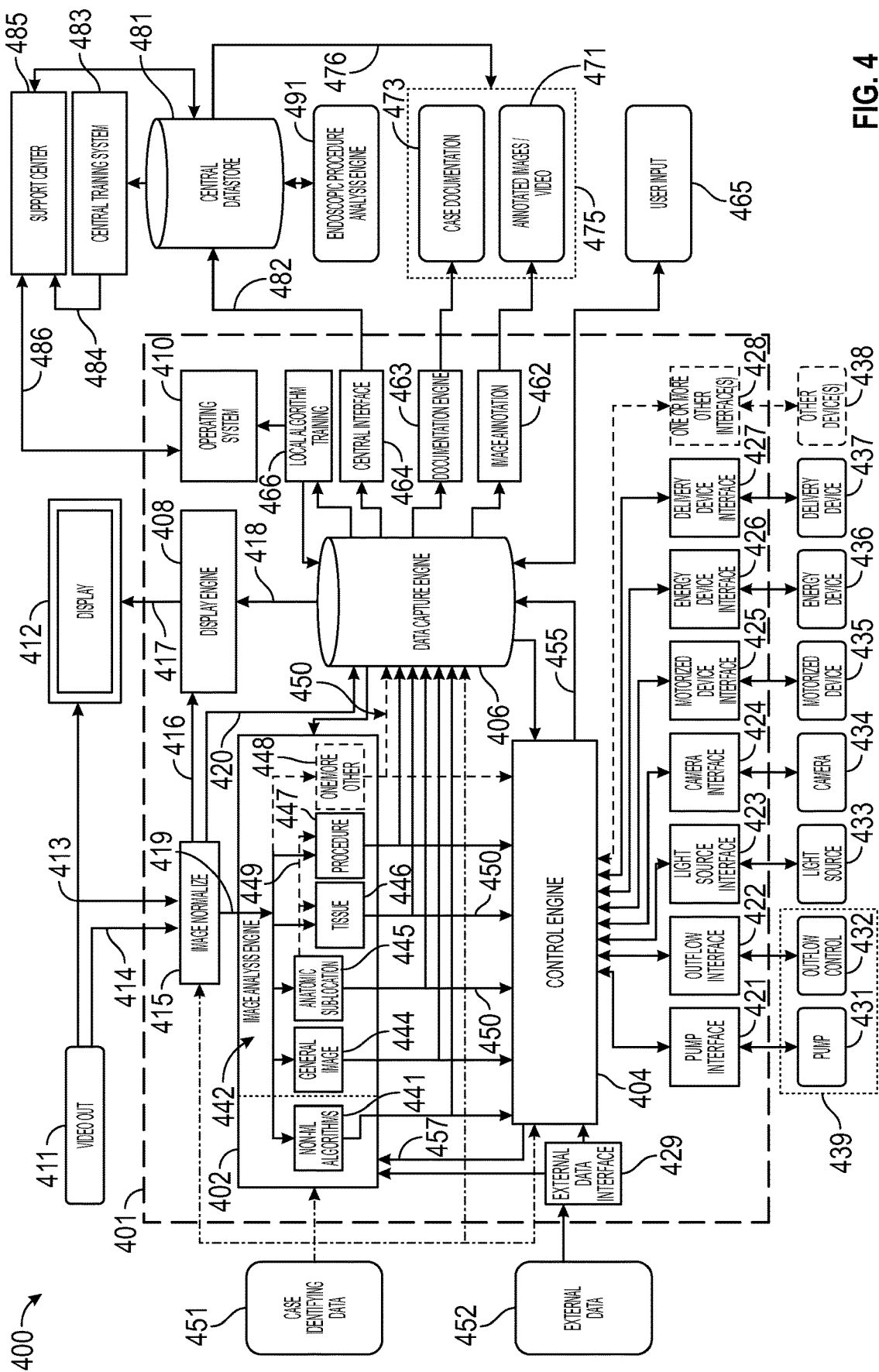
FIG. 4 is a schematic block diagram of an endoscopic image analysis system, according to one embodiment of the present disclosure.

FIG. 4 is a schematic block diagram of an endoscopic system 400, according to one embodiment of the present disclosure. FIG. 4 provides a detailed view of an image analysis system 401, according to one embodiment. The image analysis system 401 may be an image analysis component (e.g., similar or analogous to image analysis component 350 of FIG. 3) to be mounted on a tower with other components of the endoscopic system 400. FIG. 4 illustrates that the image analysis system 401 can include a plurality of methods or modes of communication with one or more of: other components of the endoscopic system 400, external data 452, electronic medical records (EMRs) in an EMR system 475, and central datastores 481. While the diagram of FIG. 4 depicts multiple different operations, processes, and/or functions as being performed by or otherwise present in a single component 401, these operations, processes, and/or functions can be distributed in one or more physical locations and devices, including one or more of the following: local to a single endoscopic system, involving a network of endoscopic systems, connected to a central server, connected to a "cloud" architecture, and any combination of these. Additionally, in some embodiments of the image analysis system 401, a subset of elements, features, processes, devices, and functionality may be included.

The endoscopic system 400 of FIG. 4 includes an image processing component 411, a display 412, a pump 431, an outflow control 432, a light source 433, a camera 434, a motorized device 435, an energy device 436, a delivery device 437, and one or more other devices 438. The pump 431 and/or outflow control 432 may be included in a medium management system 439. The endoscopic system 400 of FIG. 4 may be identical, similar, or analogous to the endoscopic systems 100, 300 of FIGS. 1 and 3, and description of components and functionality from above can be applicable to FIG. 4, though not repeated here for sake of brevity. (As an example, the content management system 324 of FIG. 3) with which an image analysis system 401 can communicate is not included in FIG. 4 for the sake of brevity.) The endoscopic system 400 of FIG. 4 can capture video data. The video data (or image data therefrom) is analyzed by the image analysis system 401, which can determine characteristics of an image the procedure team may be viewing, control one or more components of the endoscopic system 400 to enhance operation of the endoscopic system and thereby enhance the experience of the procedure team performing the procedure and/or the experience of the patient being treated, capture endoscopic case data, and present an enhanced image to the procedure team.

The image analysis system 401 includes an image analysis engine 402, a control engine 404, a data capture engine 406, a display engine 408, and an operating system 410. The image analysis engine 402 receives the video data (or other image data) to determine characteristics of an image that the procedure team may be viewing. Based on the determined characteristics, the control engine 404 can control one or more components of the endoscopic system to enhance the image quality, increase utility of the image data, and otherwise improve operation of the endoscopic system to enhance the experience of the procedure team performing the procedure and/or enhance the experience of the patient being treated. The data capture engine 406 can capture endoscopic case data for documentation, training, and use during the procedure. The endoscopic case data includes any data associated with a case (or procedure). The endoscopic case data can include, but is not limited to, case identifying data 451 (e.g., patient name, birthday, surgeon, anatomic location), image characteristics from the image analysis engine 402, control data from the control engine 404, state data of the endoscopic system 400, external data 452, images and/or video from an imaging processing component 411, and references to image and/or video from an imaging processing component 411 that are stored in a different system. The display engine 408 can present image data (e.g., video data) and/or endoscopic case data for the procedure team. The display engine 408 can present the image data and/or endoscopic case data for the procedure to the display 412 and/or one or more other display devices or output devices. The one or more other display devices or output devices can include one or more secondary displays on which an endoscopic image and/or any endoscopic case data is displayed, which can include any alternative method of displaying visual information related to the image analysis system 401, including but not limited to any wearable technology (e.g., glasses, goggles).

The image analysis system 401 can also receive case specific data 451 and external data 452, and can receive user input 465 (e.g., user confirmation data), as will be explained in further detail below. The image analysis engine 401 can also include and/or interact with a central datastore 481, which can be accessed to store and/or to receive endoscopic case data and/or training data, as will be explained in further detail below.

The image analysis system 401 receives video data 413, 414, such as from an output 411 of an image processing component. In FIG. 4, the output 411 is a video output to provide video data, and, as can be appreciated, in other embodiments the output 411 of the image processing component can provide any type of image data from an endoscopic system 400, including analog and/or digital. The video data 413, 414 can include raw data from a camera, partially processed data, or fully processed and formatted data (e.g. HDMI, DVI, S-Video, RGB, etc). The source of the video data 413, 414 could be from a camera physically inside the body (ie. chip-on-tip) or the source of the data could be a camera physically located outside the body that is capturing a view transmitted or otherwise provided through a scope. In other embodiments, the video data 411 can be saved data from a file or other storage format containing one or more images from an endoscopic case in non-real time.

Figure 11:
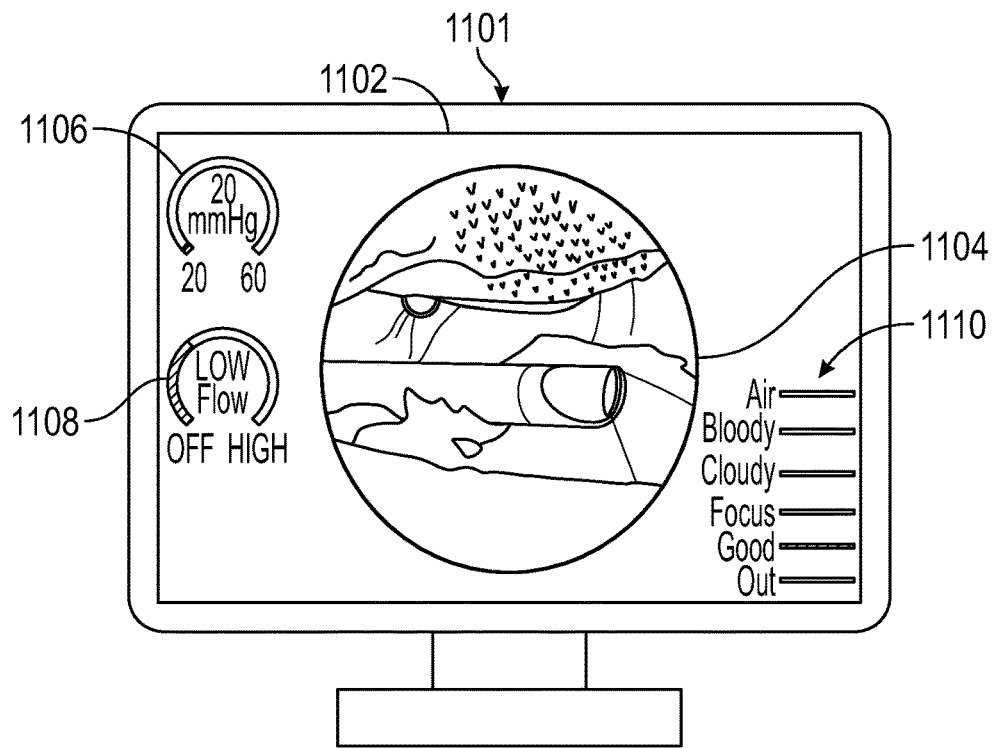
FIG. 11 is a display of an endoscopic system, according to one embodiment of the present disclosure, and illustrates a presentation of data used and/or generated by an image analysis system, the data being presented on a display within areas typically unused in rendering an endoscopic image.

In one embodiment, the image analysis system 401 receives video data 413 from a "split" signal, as shown branching from a connection to the display 412 of the endoscopic system 400. This configuration includes the output 411 of the image processing component providing video data 413 directly to the display 412 that the user and/or procedure team can view. A "split" signal then provides video data 413 to the image analysis system 401, whether through a splitter before it reaches the display 412, or as output from the display 412. In a routing where a split signal 413 is fed to both the image analysis system 401 and to a display 412, a video mixer can be used to combine the signal to the display 412 with the signal 417 from the display engine 408 to create a combined image on a single display 412. An example of this combined image is shown in FIG. 11. In a routing where a split signal 413 is sent to the image analysis system 401 from the display 412, no information from the image analysis system 401 can be included for presentation on the display 412. Any information related to the image analysis system 401 will therefore necessarily be shown on a separate display.

In another embodiment, the image analysis system 401 is positioned "inline" to receive video data 414 from the image processing component. This configuration includes an output of the image processing component providing video data 414 directly to the image analysis system 401. The video data 414 is processed, and additional information (e.g., from the endoscopic case data) can be optionally added to the original endoscopic image data, which is then displayed on one or more displays, including the primary display 412 that the user observes during the procedure. In this embodiment, the functionality of the image analysis system 401 can be physically located in a separate component from the image processing component. Alternatively, in another embodiment, functionality of the image analysis system 401 can be physically located in the image processing component.

The video data 413, 414 that is sent to the image analysis system 401 may be first processed by an image normalization engine 415. For example, this image normalization engine 415 can process any format of incoming signal (e.g. HDMI, DVI, VGA, analog, etc). This incoming signal can also be raw data from a camera and/or a partially processed format internal to an endoscopic image processing component. Ultimately, the video data 413, 414 may be converted to a series of individual time-stamped images in a standard format. The standard format may be an industry standard format, or an internal format to the endoscopic system 400 and/or image analysis engine 401.

In addition to converting video data 413, 414 into one or more images (e.g., in the standard internal format), the image normalization engine 415 can also receive case identifying data 451 to make further adjustments to the one or more images as needed. For example, for endoscopy cases where laterality is involved, all images can be converted to right (or left) prior to passing them along to the image analysis engine 402. An example of this is in knee arthroscopy where anatomic sublocation classification is performed to distinguish between a medial meniscus and a lateral meniscus.

The image normalization engine 415 may also provide the video data 416 (e.g., the same video data 413, 414 received or a derivation thereof) directly to the display engine 408. This video data 416 can be used by the display engine 408 to provide video data 417 to the display 412 to present video in real time. The video data 416 provided to the display engine 408 may be useful in an inline configuration. The image normalization engine 415 and/or display engine 408 may preserve resolution, color, and all other video characteristics so that video can be displayed as expected by the user if no image analysis were being done. Providing the video data 416 to the display engine 408, the endoscopy system 400 will function exactly as in a traditional configuration.

The display engine 408 can perform multiple functions, which may depend on the configuration. In a "split" configuration where the video data 413 is being sent directly from the image processing component output 411 to a primary display 412, the display engine 408 can prepare information applicable to the image analysis system 401 and format that information for one or more displays, whether the primary display 412 or one or more secondary displays. In an "inline" configuration, the display engine 408 primarily provides real-time endoscopic video data 417 to the primary display 412. The display engine 408 can additionally receive endoscopic case data 418 from the data capture engine 406. This endoscopic case data 418 can include, but is not limited to: results of image classification and/or analysis from the image analysis engine 402, case identifying data 451, external data 452, state data from and/or any changes made (e.g., by the control engine 404) to the state of one or more components of the endoscopic system 400, and any user input 465. Because the operating system 410 can be used to define and/or modify the function and/or algorithms in any part of the image analysis system 401, including the display engine 408, the functionality of the display engine can be modified by updated algorithm data 484 and/or system update data 486 as received from the central training system 483 and/or support center 485 respectively. Any additional information from the data capture engine 406 can be additionally formatted and displayed according to user and/or facility preferences.

The display engine 408 may design or otherwise prepare an internal representation of a screen of the display 412 and/or one or more secondary displays. That internal representation of the screen as designed in the display engine 408 may be translated into an output format (e.g., video data 417) and displayed on the display 412 and/or one or more secondary displays. Most displays have standardized on HDMI, but any suitable format of video data 417 may be provided.

In both an inline routing providing video data 414 and a split routing providing video data 413 where a video mixer is used to combine the signal directly from the image processing component 411 and the output from the display engine 417, a combined image showing both the endoscopic image(s) and any additional information added by the image analysis system 401 can be shown on a primary display 412. In a split routing video data 413 where there is not an opportunity to combine video signals before the output 411 of the image processing component is displayed on a primary display 412, the video data 417 from the display engine 408 can drive a secondary display. In any configuration, video data 417 from a display engine 408 can alternatively be used to drive glasses or other forms of technology to display visual information.

As the image normalization engine 415 creates a series of individual images 419 (e.g., a series of time-stamped images) in a standard internal format, copies of these images 420 may be sent to the data capture engine 406. Alternatively or in addition, in embodiments where individual images are not saved but an entire video or series of images is saved, a time stamp referring to an individual image as sent to the image analysis engine 402 can be provided to the data capture engine 406. Alternatively or in addition, in embodiments where an endoscopic system 400 is already set up to save images and/or video in systems external to the image analysis system 401, timestamps referencing individual images in the externally saved image(s) and/or video can be provided to the data capture engine 406.

The image analysis engine 402 receives image data from the image normalization engine 415. The image data may be one or more images 419 (e.g., time-stamped images) from the video data 413, 414. Each image of the one or more images 419 are analyzed to determine various characteristics of each of the one or more images 419. Various algorithms are used to extract information from the image characteristics. One example of determining image characteristics includes using machine learning (sometimes herein "ML") algorithms or other artificial intelligence (sometimes herein "AI") algorithms to determine the image characteristics. In the embodiment of FIG. 4, the image analysis engine 402 includes one or more machine learning algorithms 442 which can identify multiple characteristics for each of the one or more images 419. The machine learning algorithms 442 may further classify each image 419 in one or more categories according to one or more characteristics of the image 419. Non-machine learning algorithms 441 can also be used to identify characteristics of each of the one or more images 419.

In some embodiments, the image analysis engine 402 may receive some contextual information from sources other than a given image 419 itself. Examples of these contextual information include, but are not limited to, one or more of the following: case identifying data 451 (e.g. knowing that a case is a knee arthroscopy can select appropriate parameters for the categorization algorithms); information external to the endoscopic system from external data 452 (e.g. information from an anesthesia machine like a blood pressure; temperature in the room from a sensor); and state information from state data 457 provided by or otherwise available from the control engine 404.

In the image analysis engine 402 of FIG. 4, there are two general categories of image analysis algorithms: ML image analysis algorithms 442 and non-ML image analysis algorithms 441. As can be appreciated, some embodiments of an image analysis engine 402 may utilize or otherwise include one or both of these general categories of image analysis algorithms.

ML image analysis algorithms (or simply ML algorithms) 442 are sometimes referred to as neural networks and/or "artificial intelligence." In the image analysis engine 402 of FIG. 4, ML algorithms 442 can identify or otherwise determine one or more characteristics of each of one or more images 419. These ML algorithms 442, possibly along with any appropriate contextual information, can further determine a classification of an image based on the characteristics. For example, the ML algorithms may determine a classification according to a dominant characteristic of a group of characteristics. The ML algorithms 442, possibly along with any appropriate contextual information, can further determine a classification of an image in one or more categories of characteristics.

Utilizing machine learning image analysis algorithms 442 in an image analysis system 402 used in a setting of endoscopy may involve training and validation of the ML algorithms 442. Training of the ML algorithms 442 does not take place during endoscopic procedures, but is an "off-line" process. A central training system 483 may provide a repository and/or development engine for training image analysis algorithms. This central training system 483 may access, receive, or otherwise train ML algorithms utilizing data from the central datastore 481. The ML algorithms 442 of the image analysis engine 402 have parameters based on previous training. There may not be any actual "learning" (or training) done in the course of operation of the image analysis engine 402. These operational algorithms are fast but are essentially unchanging. To train ML algorithms, the central training system 483 may process large quantities of data through a different set of training algorithms. Since one or more endoscopic system(s) 400 can eventually generate millions of images with information about the characteristics of those images, the ongoing training can continue to refine and/or enhance training algorithms, for example to become more accurate, to identify new characteristics, classify in new classifications, and organize characteristics and/or classifications in new categories, etc. The training of training algorithms may be done centrally by the central training system 483 so that data from multiple endoscopic systems (which could number tens of thousands or millions of cases) and/or a subset could be used to train very accurate algorithms in a central location. These modified training algorithms can be tested, which can be done by using a percentage of training data (where an image's characteristics are "known") to train, and a smaller percentage as test data to make sure the updated algorithms are accurate. Any modifications to the training algorithms and/or parameters to improve functionality are validated before algorithm data 484 is sent to an individual endoscopic image analysis system 401 for use in any endoscopic procedure. The algorithm data 484 can be modified algorithms to replace existing algorithms, updated or revised parameters for existing algorithms, new algorithms, or anything pertaining to algorithms. An operating system 410 of the image analysis system 401 can appropriately apply the algorithm data 484 to or within the image analysis system 401. On a more limited data set, similar training and/or development of ML algorithms can also be performed locally by a local algorithm training engine 466 within an individual image analysis system 401. An example of this includes learning preferences for a specific user for a specific case type. Instead of using data from a central datastore 481, local algorithm training by a local algorithm training engine 466 would utilize data contained in the data capture engine 406.

Non-machine learning image analysis algorithms 441 can also be used to extract information from one or more images 441 to determine or otherwise identify one or more characteristics. These algorithms can be implemented in or according to one or more domains, including RGB or CMYK. Examples of these types of algorithms include, but are not limited to: color detection, edge detection, color content, and contrast.

As previously introduced, the image analysis engine 402 includes algorithms 441, 442 to determine or otherwise identify one or more characteristics of an image 419. The image analysis engine 402 can include algorithms 441, 442 that not only identify characteristics, they also classify or determine a classification of the image based on the characteristics. In some embodiments, the algorithms can classify the image according to a dominant, primary, and/or most relevant characteristic.

In some embodiments, the image analysis engine 402 may include one or more categories (e.g., categories of characteristics and/or classifications) each including or otherwise organizing multiple characteristics to make possible multiple potential classifications. The algorithms 441, 442 of the image analysis engine 402 may classify an image (or otherwise assign an image to a classification) within each of the one or more categories by determining and/or evaluating one or more characteristics of the image. The one or more categories may be predefined, such that the algorithms 441, 442 of the image analysis engine 402 can be configured in advance to determine the one or more characteristics in order to assign the image to a classification in each of the one or more categories. The algorithms 441, 442 may classify the image in each category of the one or more categories based on the one or more characteristics, such as according to a dominant, primary, and/or most relevant characteristic in each category. The image analysis engine may determine each classification of one or more classifications of the image from a different predefined category.

In some embodiments, the algorithms 441, 442 of the image analysis engine 402 may determine each characteristic of a plurality of characteristics of the image from a different predefined category. Each characteristic of the plurality of characteristics of the image may be determined for a different predefined category and the image analysis engine can then classify the image in each category based on the determined characteristic for that category.

In still other embodiments, the algorithms 441, 442 of the image analysis engine 402 may assign an image to a classification within a category from one or more categories (of classifications) each including or otherwise organizing multiple classifications, according to the characteristics of the image. The categories of classifications may be predefined, such that the image analysis engine 402 and algorithms 441, 442 thereof can be configured in advance to assign the image to a classification in each category. The algorithms 441, 442 and/or the image analysis engine 402 may assign the image a classification in each category of the one or more categories based on a plurality of characteristics, such as according to a dominant, primary, and/or most relevant characteristic, according to the category. Stated otherwise, the algorithms 441, 442 and/or the image analysis engine 402 may determine each classification of a plurality of classifications of the image from a different predefined category. Each classification of the plurality of classifications of the image may be determined for a different predefined category. The algorithms 441, 442 and/or the image analysis engine 402 may classify the image in each category based on the plurality of characteristics, such as according to a dominant, primary, and/or most relevant characteristic in the category.

One example of using machine learning to classify an image according to image characteristics is within a "general image" category. Classifications in this category can pertain to general information applicable to a particular type of endoscopy and anatomical location. While an image might have characteristics of one or more of the classifications, it can be classified within the category according to a dominant characteristic. For example, in knee arthroscopy, potential classifications of an image within a "general image" category can include: Air, Bloody, Cloudy, Focus, Good, and Out-of-Patient. The image may be classified in one of these classifications in this "general image" category according to a dominant characteristic. This classification of the image in this general image category might be used, for example, to modify the endoscopic system 400 (e.g., parameters on a medium management system 439). To classify an image in the general image category, the ML algorithms 442 may include a general image ML algorithm 444, which analyzes the image to determine or otherwise identify one or more characteristics pertaining to the general image category and to classify the image based on one or more of the identified characteristic(s). The general image ML algorithm 444 may be trained or otherwise configured to identify or otherwise determine if an image has the characteristic of being bloody. If the image is bloody, the general image ML algorithm 444 can classify the image as Bloody, which is a classification in the general image category. In this example, the characteristic and the classification closely correlate (and seem to be the same), but in other embodiments a classification can be different from a characteristic, or even determined based on a combination of multiple characteristics.

Another example of using machine learning to classify an image according to image characteristics is within an "anatomic sublocation" category. Classifications in this anatomic sublocation category can include a specific sublocation applicable to a particular type of endoscopy and anatomical location. For example, in knee arthroscopy, potential classifications of an image within the anatomic sublocation category can include: Suprapatellar Pouch, Patellofemoral Joint, Medial Compartment, Notch, Lateral Compartment. An anatomic sublocation ML algorithm 445 can determine characteristics of the image and/or a classification of the image (based on characteristics) in this anatomic sublocation category. In some embodiments, while an image might have characteristics of one or more of the classifications within this category, the classification within the anatomic sublocation category may be determined based on a dominant characteristic. The determined classification might be used, for example, for setting the settings of an energy device 436. The classification in the anatomic sublocation category may also be used for selecting other ML algorithms, categories, and/or classifications. The classification may be provided, utilized, or otherwise included for case documentation, image annotation, and the like, such as in an EMR system 475.

Another example of using machine learning to classify an image according to image characteristics is within a "tissue" category. Classifications in this tissue category can pertain to tissue applicable to a particular type of endoscopy and anatomical location. Stated otherwise, classification in the tissue category can be assisted by using the results of another prior classification 449 (e.g. using an identified classification from the "anatomic sublocation" category to narrow the potential tissue classifications). For example, in knee arthroscopy in the medial compartment, potential classifications of an image within the tissue category can include, but not be limited to: Medial Femoral Condyle, Medial Meniscus and Medial Tibia. For example, a Patella classification and an ACL classification would not be available as potential classifications where the classification in the anatomic sublocation ML algorithm 445 determined a classification of medial compartment in the anatomic sublocation category. In addition, there can potentially be classifications or sub-classifications for tissue grading (e.g. Medial Femoral Condyle (Normal), Medial Femoral Condyle (Grade 1), Medial Meniscus (Normal), Medial Meniscus (Tear)). A tissue ML algorithm 446 can determine characteristics of the image and/or a classification of the image (based on characteristics) in this tissue category. In some embodiments, while an image might have characteristics of one or more of the classifications within this category, the classification within the tissue category may be determined based on a dominant characteristic. The classification in this tissue category might be used, for example, for setting energy device settings 436. The classification in this tissue category might be used, for example, for selecting other ML algorithms, categories, and/or classifications. The classification in this tissue category might be used, for example, for documentation, image annotation, and the like, such as in an EMR system 475.

Another example of using machine learning to classify an image according to image characteristics is within a "procedure" category. Classifications in this procedure category can include an action of a user applicable to a particular type of endoscopy and anatomical location. Classification can be assisted by using the results of another classification 449 (e.g. using "anatomic sublocation" and/or "tissue classification" to narrow the potential procedures). For example, in knee arthroscopy in the medial compartment, a "procedure" classification of an image within the category can include: Meniscal Repair, Partial Medial Meniscectomy, Medial Femoral Chondroplasty, Loose Body Removal, and Microfracture. Patellar Chondroplasty and ACL Reconstruction wouldn't be options in this sublocation. A procedure ML algorithm 447 can determine characteristics of the image and/or a classification of the image (based on characteristics) in this procedure category. In some embodiments, while an image might have characteristics of one or more of the classifications within this category, the classification within the procedure category may be determined based on a dominant characteristic. The classification in this procedure category might be used, for example, for setting motorized instrument settings 435. The classification in this procedure category might be used, for example, for documentation, image annotation, and the like, such as in an EMR system 475. Another example of using a procedure classification for an image may be for control of a medium management system when an ACL tunnel is drilled and fluid is free-flowing out of the knee. Instead of increasing target flow to make up for the decreasing pressure, the image analysis system 401 could actually decrease flow and/or stop the flow to "dry scope", with pulses to clear the scope when bloody (based on the bloody classification in the general image category).

While these are some examples of ML algorithms 442 and characteristics, classifications, and categories pertaining thereto, the image analysis engine 402 can include one or more other ML algorithms 448 to identify characteristics and/or classify an image, including in one or more other categories. Some of these categories can include contextual information besides the image. Some of these categories can include the results of other categorizations.

As described above, the results of classifying an image in a category according to the image characteristics can be used for multiple things. One or more classifications can have one or more uses including, but not limited to: being used as input to a control engine 404, being collected in a data capture engine 406 for additional functionality, and as an input to one or more other algorithms for image classification and/or analysis.

After the image analysis engine 402 uses one or more algorithms 441, 442 to determine one or more characteristics of an image, the results 450 of the analysis are passed along to a control engine 404. These results 450 are also passed along to the data capture engine 406. The results 450 can be characteristics, classifications, and/or classifications within categories, as previously explained. In some embodiments, the results 450 can include control parameters, instructions, commands, or the like, for use by the control engine 404. From here, the results 450 are used for one or both of display purposes during the procedure (or case) and various functions after the procedure (or case). In some embodiments, the results 450 may be used solely for documentation after a case and may not be used by a control engine 404.

Case identifying data 451 can be used in an image analysis system 401 to set many parameters of the system 401 for that case. Examples of case identifying data include but are not limited to: patient ID, sex, age; surgeon/user; facility; system; room number; endoscopic system identifier; anatomic area (e.g. abdomen, knee, hip, etc); side (if laterality present); and planned procedure. In some embodiments, the entering of case identifying data can be facilitated by using the camera 434 of the endoscopic system 400.

Case identifying data 451 can be used by the image normalization engine 415. Examples of how this can be used include, but are not limited to: reflecting images left to right when laterality is present to normalize images, setting parameters for a particular tower configuration, and adjusting to user and/or facility preferences.

Case identifying data 451 can be used by the image analysis engine 402, for example, to select appropriate algorithms 441, 442, characteristics, classifications, and categories, and the like for analyzing images.

Case identifying data 451 can be stored by the data capture engine 406. This can be used to organize all of the intra-procedure data so it is all attached to a specific case. It can also be used for functions including, but not limited to: data display during a case using the display engine 408, documentation and/or image annotation such as in an EMR system 475, and transmission to a central datastore 481 for additional functions as described below.

Case identifying data 451 can be used by the control engine 404. Depending on the particulars of the case, different control logic can be used to respond to the image categorization. For example, a knee case might have one set of control logic whereas a shoulder case might have a different set. Additionally, depending on the specific endoscopic system (e.g., arthroscopy tower), there may be different components that can be controlled.

External data 452, or information that is generally considered external to the typical components of an endoscopic system 400, can be considered. Examples of this include, but are not limited to: vital signs such as blood pressure and/or heart rate, room temperature, and positioning of a patient. External data 452 can be used for an input to control logic, such as proactively raising fluid pressure in an arthroscopic case when the blood pressure is going up as opposed to reacting to bleeding after the image quality is degraded. External data 452 can be captured using an external data interface 429. This interface 429 can be varied, and includes any way that information external to an endoscopic system 400 can be obtained. It can include, for example, connecting to an existing port on a device, whether through a wired or a wireless configuration. In cases where ports are not available, or where regulatory issues prevent a direct connection, a sample alternative way to get information is to attach a camera in such a way that it is pointed at a screen with the desired information and OCR technology is used to extract pertinent data. After being obtained through an appropriate interface, external data 452 can be provided to the image analysis engine 402. As described above, examples of this could include information from an anesthesia machine like a blood pressure or a sensor for temperature in the room.

All of the information or endoscopic case data captured by or created by the control engine 404 can be sent to, collected, captured, or otherwise received by a data capture engine 406. This endoscopic case data can include all of the state data corresponding to an individual time-stamped image. The endoscopic case data can also include any changes made to any component by user input 465. The endoscopic case data can also include any parameter limits that the control engine 404 is using at that state. In configurations in which no image analysis engine 402 is used, time-stamped information from the control engine 404 can still be captured by the data capture engine and used for various functions.

The control engine 404 interfaces with components of the endoscopic system 400. In some embodiments, the components that the control engine 404 interfaces with include all controllable components of the endoscopic system. The control engine 404 receives input (results 450) from the image analysis engine 402. Additionally, the control engine 404 may receive input from external sources of data 452. Based on control logic particular to a specific case type, which may be received from case identifying data 451, the control engine 404 can be used to control one or more components of the endoscopic system 400. The control engine 404 tracks current state data of each component in order to make any changes. Any changes made by the control engine 404 to any component of the endoscopic system 400 may be limited by safety operating parameters, which may be defined by the user, the endoscopic system 400, a regulatory body (e.g., the FDA) or the like. Additionally, the user can retain ultimate control of the endoscopic system 400, and any interaction the user has with a component is captured.

In some embodiments where bidirectional communication with a component is available, the component can be queried by the control engine 404 to maintain state data regarding the component. In other embodiments where only one-way communication to a component is possible, a dead reckoning method can be used to maintain state data regarding the component, tracking any changes to the state made by a user.

Information about the state of the endoscopic system 400, or state data 457, gathered by the control engine 404 can be fed to the image analysis engine 402. This could enable varied functionality in the image analysis engine 402. An example of this could include differentially classifying an image in a category based on current pump pressure.

The control engine 404 connects to various interfaces 421-428 that can facilitate communication with and/or control of one or more components of an endoscopic system 400. The interfaces with one or more components of an endoscopic system 400 can include a pump interface 421 to a pump 431 or medium management system 439, an outflow interface 422 to a outflow control 432 or medium management system 439, a light source interface 423 to a light source 433, a camera interface 424 to a camera 434, a motorized device interface 425 to a motorized device 435, an energy device interface 426 to an energy device 436, a delivery device interface 427 to a delivery device 437, and one or more other interface 428 to other controllable devices 438 of the endoscopic system 400. The interfaces 421-428 can be unidirectional or bidirectional. They can be wired or wireless. They can follow any protocol necessary and/or appropriate to interface with a component. Some examples of possible ways to interface with a component include, but are not limited to, the following examples:

In one example, a port, generally on the front, where a hand and/or foot control is connected (e.g., plugged in) can be used with an interface inserted into the path between the control and the component. This allows control of the component and/or capture of any user inputs, though it may not allow for querying the component.

In another example, a port, generally on the back, can be used where an API allows communication with the component, which may allow control of the component and can often provide query capability.

In another example, a camera can be used that is dedicated to a screen on a component and which uses character recognition or some other method to capture data from the screen. This is essentially a "query function" when that is not possible through a port, and can be combined with the "front port/control only" interface to effectively create a bidirectional interface.

FIG. 4 depicts certain components 431-438 of the endoscopic system 400, and some of the various components 431-438 are shown as being physically separate for the sake of demonstration, explanation, and/or clarity. In other embodiments, one or more of these components 431-438 can be combined physically in any manner even though they are depicted as distinct in FIG. 4. In the case of multiple functions that are combined into a single physical component, the interface(s) 421-428 can also be combined, though the interface(s) are not necessarily combined. Some demonstrative examples of combinations of components in arthroscopy just related to a medium management component 439 include, but are not limited to: inflow only pump; inflow and outflow pump; inflow/outflow/motorized shaver suction; inflow/shaver suction/electrocautery suction; and inflow/outflow suction/electrocautery suction.

A medium delivery system 439 (eg. pump, insufflator) can include any device that controls delivery of a liquid or gaseous medium to an area being visualized. Some medium delivery systems 439 are inflow only devices (e.g., a pump 431), while others include an outflow control 432 capability. There are also a number of other potential combinations as described above. For the majority of medium delivery systems 439, a target pressure is set by the user. A target flow range can sometimes be set on the medium delivery systems 439. The medium delivery system 439 senses the actual pressure in various ways and adjusts the actual flow to try to match the target pressure to the actual pressure.

The functions that can be controlled on a medium delivery device 439 may depend on the particular endoscopic application. For arthroscopy, for example, one or more of the following functions can be possible depending on the component: Pump Run/Stop, Set Target Pressure, Increment Target Pressure (up or down), Query Target Pressure, Query Actual Pressure, Set Target Flow Range, Increment Target Flow Range (up or down), Query Target Flow Range, Query Actual Flow, Set Actual Flow, Increment Actual Flow (up or down), and Query Fluid Used.

Medium (e.g. fluid or gas) leaving an area being visualized can often be controlled with an outflow control 432. This functionality is often combined with a medium delivery device (e.g. inflow pump) 431 in a combined medium management system (e.g. arthroscopic pump) 439. There are embodiments when this can be a standalone component. For example, in laparoscopy, there are manual smoke evacuators that can be used to remove gas from the abdomen if it gets smoky and/or cloudy. When coupled to an image analysis system 402, the control engine can control an outflow control 432 such as an automated smoke evacuator to automatically clear the image when needed. As another example, in arthroscopy, there are some medium delivery devices 439 that do not have the capability to control outflow without, for example, a motorized instrument being in the field. In this instance, an automated outflow device can be controlled to allow for fluid management when a motorized instrument is not in the joint. As another example, in some embodiments, a user may use gravity as an inflow to a system, and an outflow only control could be used to help clear the image as needed.

In some embodiments, particularly common in arthroscopy, both a medium delivery device 431 and an outflow control device 432 are combined in a medium management system 439. In an embodiment where control of both the inflow and the outflow is possible, an image analysis system 401 provides a possibility of enhanced control. For example, traditional systems generally stop or significantly reduce the flow when a target pressure is met, and increase it only when the pressure drops. If the image is cloudy, the user manually increases the outflow which drops the pressure, and flow is increased to maintain the pressure. By being able to analyze the image, an image analysis system 401 can maintain a constant pressure and only adjust flow as needed to clear a cloudy image.

Another example of how an image analysis system can improve functionality of a medium management system 439 includes situations where the control systems in traditional endoscopic systems do not work well. For example, in performing an anterior cruciate ligament reconstruction, fluid can free flow out a tunnel created in a bone. In this case, the pressure in the joint drops and the programmed response of the pump is to increase flow to restore pressure. Often, however, more fluid can flow out the tunnel than the pump can provide. The turbulent flow makes it difficult to see. In this case, a user can manually stop the pump and let the fluid drain out of the joint, essentially performing that part of the procedure with air instead of fluid. If the end of the scope gets bloody, turning on the flow briefly can clear it. In an endoscopic system 400 incorporating an image analysis system 401, because sublocation and procedure can be determined from image data, an appropriate response of the medium management system 439 can be performed by the control engine 404.

Without a light source 433, endoscopic images would generally be black, as there is no illumination within the body of a patient. A safety issue can occur when an endoscope is removed from the patient as the endoscope is often set on drapes which can be made of paper. A light source 433 for an endoscope is generally high intensity and can be highly focused through the endoscope. There are reports of patient burns and even fires from light sources 433. A control engine can put the light source 433 on standby when the image analysis engine 402 determines that the endoscope is removed from a patient.

A camera 434 captures an image of an area being viewed—i.e., an area within a field of view of an endoscope positioned at an area to be addressed. In many endoscopic systems, the camera 434 captures an image transmitted through an endoscope. In other endoscopic systems, with chip-on-tip configurations, the image is captured within the patient. In any configuration, the camera 434 connects, either wired or wirelessly, with an image processing component that can perform one or more functions including, but not limited to: converting raw data into a suitable output, performing an auto-shutter function based on general image brightness, and allowing basic user input from a button on the camera 434 to capture images and/or videos. In some embodiments, the functionality of an image processing component can be physically located within the camera. With incorporation of information from an image analysis engine 402, a control engine 404 can enable additional functionality with regards to a camera 434 and associated image processing component.

An example of this additional functionality afforded by inclusion of an image analysis engine 402 includes user input from one or more buttons on the camera 434 for one or more of the following: storing classifications from an image analysis engine 402 associated with a captured image for later use, controlling other components of an endoscopic system that are also controlled by the control engine 404 (e.g. allowing a user to change pressure settings on a medium delivery device using a button on a camera, toggling a smoke evacuation device using a button on a camera).

Another example of functionality is an auto-focus function on the camera 434. In traditional endoscopic systems, standard auto-focus algorithms are difficult, as they generally rely on contrast and/or transition detection. In endoscopy, these algorithms generally can not distinguish between images that are blurry, cloudy, smoky, or out-of-focus. Because the image analysis engine 402 can make this determination, auto-focus can be enabled. For example, if a transition or edge is indistinct in an endoscopy image because the image analysis engine 402 determines that it is bloody and/or cloudy, the control engine 404 can make appropriate changes to the medium management system. If a transition or edge is indistinct because of smoke in a laparoscopic image, the control engine 404 can control a smoke evacuator unit to help clear the image. Importantly, if the image analysis engine 402 determines that image quality is primarily one of focus, the control engine 404 can send commands to enable auto-focus capability on the camera 434.

While most embodiments of endoscopic systems have an image processing component which is used to process and/or convert a raw image as captured by a camera into a format suitable for display, the possibility exists that the appropriate circuitry is built into a camera, which may enable a display to be plugged directly into a camera without a separate image processing component. This possible embodiment should be considered functionally equivalent and any embodiment incorporating one or both of a camera and an image processing component are within the scope of the present disclosure.

The motorized device 435 may be a shaver, burr, saw, rotary tool, or the like. As previously mentioned, many endoscopic systems include a component which drives a motorized device 435. The image analysis system 401 of FIG. 4 includes the ability for the control engine 404 to control the motorized device 435, based on analysis of one or more images by the image analysis engine. Motorized devices 435 additionally often include a suction port that is attached to one or both of an unregulated wall suction (in which case the amount of suction is often manually controlled by the user) and to an outflow device that can provide more regulated amounts of suction. For more modern medium management systems 439, control of the suction on a motorized device is often correlated with the outflow through an outflow cannula (e.g. when a shaver is being used, the pump turns off the standard outflow path and reroutes suction to the shaver.)

Based on analysis, evaluation, and/or classification of an endoscopic image by the image analysis engine 401, the control engine 404 can make various adjustments to the motorized device 435. For example, when performing a knee arthroscopy, a lower RPM rate and lower suction might be automatically set when performing a chondroplasty in the lateral compartment of the knee, while a higher RPM rate and a higher suction might be set when more aggressively performing removal of a tougher bucket-handle medial meniscus tear. Similar to the medium management system 439, the user can retain ultimate control of any motorized device 435 through a hand and/or foot control as in current endoscopic systems. In endoscopic systems where actual values of motorized device settings are available, these can be saved in the data capture engine 406 and/or central datastore 481 for use in further refinement of control algorithms by the central training system 483.

In endoscopy, various energy devices 436 can be used to apply energy to tissues in an area being addressed. Examples of energy devices 436 that are used in arthroscopy to apply energy to tissues include, but are not limited to, electrocautery (including monopolar and/or bipolar) and laser devices. Examples of energy devices 436 in laparoscopy include, but are not limited to, electrocautery (including monopolar and/or bipolar) and an argon beam coagulator. The energy devices 436 generally have different settings for different functions. For example, in monopolar electrocautery, there are generally cut and coagulation modes, where characteristics of the energy applied (e.g., voltage, waveform, current, etc) are adjusted to achieve different goals. In some energy devices 436 used to apply energy to tissue, there is often associated suction which can be used for functions to increase visualization including, but not limited to, one or more of removing tissue and removing gas.

In the present invention, outputs from the image analysis engine 402 can be used by the control engine 404 to adjust settings on a component that drives the energy device 436 to deliver energy to tissue. One example of this includes adjusting the suction on the energy device 436 when a general image classification algorithm 444 classifies an image as air or cloudy. Another example, which uses classifications determined by an anatomic sublocation algorithm 445 and/or a tissue type algorithm 446 includes adjusting the mode and power settings of an electrosurgery component to ablate tissue when performing a subacromial decompression in a shoulder surgery, and changing the settings to enable coagulation when in the glenohumeral joint portion of the surgery.

In some endoscopic procedures, a substance can be delivered to an area being visualized. Some substances are more diagnostic in purpose, while others are more therapeutic and delivered as part of a treatment. One example of a substance that can be used to help with diagnosis is a dye, whether using a visual, ultraviolet, or infrared wavelength, which is differentially expressed in different tissues. One example of a substance that is part of a treatment is a bone filler which is delivered in a liquid form and which hardens into a solid.

A substance that can be seen in an area being visualized can be delivered locally (directly to the area) or remotely (e.g., through an IV). Sometimes this substance is delivered under manual control and/or in an unmeasured amount. In many cases, a delivery device 437 is used to control the volume and/or the rate of the substance being delivered. Examples of these devices include, but are not limited to, infusion pumps and devices in which syringes are inserted.

In the present invention, an image can be analysed by an image analysis engine 402. Depending on the application, one or more ML algorithms 442 and non-ML algorithms 441 can be used to determine changes made to a view (provided by an endoscope, as depicted in an image) by a substance delivered, and the control engine 404 can adjust parameters of the delivery device 437 to optimize the utility of the image and/or safety of the procedure.

An example of how this control can be beneficial relates to administration of a contrast agent or dye. Because many contrast agents can have dose-dependent side effects, giving as low of an amount as possible is beneficial. Instead of giving a fixed amount, a delivery device 437 can be controlled to deliver the lowest amount of a contrast agent to affect a change in the image as determined by the image analysis engine 402. Another example of how this control can be beneficial relates to delivery of a bone-filler. In a tibia fracture, for example, a surgeon might administer a bone filler into a defect in the bone while watching a fracture line in the knee with an arthroscope. As soon as some of the filler is seen in the arthroscopic image as determined by the image analysis engine 402, the delivery device 437 can be controlled to stop delivery.

While the foregoing examples describe components of an endoscopic system 400, according to one embodiment of the present disclosure, it can be appreciated that one or more additional components 438 can also be included and/or controlled by the control engine 404 of an image analysis system 401. When the effect of these components 438 changes an endoscopic image to a degree it can be analyzed by an image analysis engine 402, and when the control engine 404 can make adjustments to the one or more additional components 438, they are included in the scope of this disclosure.

Information related to one or more procedures can be stored in a data capture engine 406. This can physically be located in an image analysis system 401 (e.g., integrated in an image analysis component) or can be in an alternative physical location in a distributed configuration. Associated with each procedure, there is a variety of information captured that can be stored as endoscopic case data. The data capture engine 406 can store the endoscopic case data. This endoscopic case data can include case identifying data 451. Examples of case identifying data 451 include, but are not limited to, one or more of the following: area being examined, laterality if applicable, planned procedure, pre-procedure diagnoses, patient demographics, user and/or other personnel, endoscopic system information, physical location, and time-stamp information.

In addition to case identifying data 451, which is generally unchanging throughout a specific procedure, the data capture engine 406 can also be used to capture and/or store a series of endoscopic case data throughout the procedure at one or more time-based intervals. The data capture engine 406 can capture endoscopic case data throughout the procedure substantially in real-time (e.g., actual time, substantially instantaneously) and/or live time (which may be with some nominal or minimal delay), or otherwise concurrent with the occurrence of the procedure. In some embodiments, the data capture engine 406 can capture data after a procedure, such as via processing a recording of video to conduct image analysis ex post facto for case documentation, algorithm training and/or analysis, or the like. The endoscopic case data can be captured automatically, including through or in conjunction with image analysis by the image analysis engine 402, control actions by the control engine 404 including any data from any component connected to the control engine, and receipt of case identifying data 451, external data 452, and/or user input 465. Capturing the endoscopic case data can include appropriate flagging, tagging, organizing, and structuring to correlate endoscopic case data for a point (or period) in time, such as a snapshot of the system at that point in time and/or in a given state. Capturing the endoscopic case data can include appropriate flagging, tagging, organizing, and structuring to enable access and/or querying (e.g., such as by an endoscopic procedure analysis engine 491) to retrieve relevant data and/or sets of correlated endoscopic case data.

Each set of endoscopic case data in this series can include, but is not limited to, one or more of the following: specific images from the endoscopic procedure 420, whether an image itself or a pointer to a specific image in a video file consisting of a plurality of images; results 450 of analysis (e.g., characteristics, classifications) performed by an image analysis engine 402 (including results of non-ML algorithms 441 and/or ML algorithms 442 performed by an image analysis engine 402); state data 455 including any settings and/or parameters from one or more components monitored and/or controlled by the image analysis system 401; changes made by the control engine 404 to one or more components of the endoscopic system 400; any external data 452 captured by and/or used by the image analysis engine 402 and/or the control engine 404; any user input 465, including changes made by a user to one or more components of an endoscopic system during a procedure and/or any feedback from the user (e.g., selecting menu choices, providing auditory information, and providing tactile information).

Endoscopic case data, and information therein, captured in the data capture engine 406 can be used during an endoscopic procedure and/or after the endoscopic procedure is concluded.

According to one embodiment, during an endoscopic procedure, endoscopic case data 418 from the data capture engine 406 can be provided to the display engine 408. In an inline video data 414 configuration, the display engine 408 can combine this endoscopic case data 418 with an endoscopic image and/or video 416 and send the combined video data 417 to a primary display 412, which the user observes to perform the procedure. In an alternative embodiment of an inline configuration, endoscopic case data such as information related to the data analysis engine 401 can additionally be displayed on one or more secondary displays 412. In a split configuration where the primary display 412 receives video data 413 directly from an output 411 of an image processing component, any information from the endoscopic case data stored at the data capture engine 406 related to the procedure will be formatted by the display engine 408 and displayed on one or more secondary displays 412. In an alternative embodiment of a split configuration, a video mixer can be used to combine video data 413 directly from the output 411 of an imaging process component with video data 417 from the display engine 408 to create a combined image which can be displayed on one or more of: a primary display and a secondary display.

During an endoscopic procedure, endoscopic case data stored in the data capture engine 406 can be used by the image analysis engine 402, for example, as inputs for time-series algorithms within the image analysis engine 402. Some algorithms used by the various routines are time-independent and perform image analysis on individual images as received from the image normalize engine 415. Other algorithms can use a plurality of images from a plurality of times in recurrent-type configurations which necessarily include information from one or more previous times, where such information can be obtained from a data capture engine 406.

During an endoscopic procedure, endoscopic case data stored in the data capture engine 406 can be used by the control engine 404 to modify how various components of an endoscopic system are controlled. For one example, if an endoscopic image is classified as cloudy by the image analysis engine 402, the action sent from a control engine 404 to a medium management system 439 might be to increase the flow to help clear the image. A time delay for incrementing the target flow can be implemented in control logic in the control engine 404 to give the increased flow rate a chance to effect a change in the image as determined by the image analysis engine 402. Since the data capture engine 406 contains time-stamped information about the endoscopic system, including any changes made to the system, this information can be used by the control engine 404 as inputs into the algorithms used to adjust one or more components of the endoscopic system 400.

During an endoscopic procedure, endoscopic case data stored in the data capture engine 406 regarding analysis by and/or function of the image analysis system 401 can be conveyed to the user(s) using methods including one or more of visual, auditory and tactile representations. One or more users can respond to this information with user input 465 to confirm, delete, edit, add to, or otherwise interact with the information provided in the endoscopic case data using one or more of visual, auditory and tactile methods. As an example, if an image analysis system controls an outflow control 432 (e.g., a smoke evacuation device) in a laparoscopy and turns it on when a surgeon does not want it enabled, the surgeon or another member of the procedure team can indicate this and signal for the outflow control 432 to be turned off. As another example, if the image analysis engine 402 classifies a tissue type to be "rotator cuff, torn" in an arthroscopic shoulder procedure and conveys this to a user, one or more users can interact with this information to confirm, delete, edit, or otherwise modify this classification.

In addition to being used during an endoscopic procedure, endoscopic case data in the data capture engine 406 can also be used when the procedure is completed. User input 465 (e.g., confirmation) of information contained in the data capture engine can be conveyed to the user(s) using methods including one or more of visual, auditory and tactile representations. One or more users can respond to this information with user input 465 to confirm, delete, edit, add to, or otherwise interact with the information using one or more of visual, auditory and tactile methods. This could additionally be done using any physical device, including but not limited to one or more of: a main or a secondary display 412, a separate computer, a tablet, a phone, or other portable computing device. One example of user input 465 (e.g., confirmation) of information contained in the data capture engine 406 after a case includes displaying the results of classifications performed by the image analysis engine 402 associated with images the user saved during the procedure including, but not limited to, one of more of the following: anatomic sublocation, tissue classification, and procedure. This user confirmation example effectively automatically annotates saved images for a user and allows the user to confirm, edit, add to, or otherwise modify any information within endoscopic case data contained in the data capture engine 406. Another example of user input 465 to confirm information contained in the data capture engine 406 includes displaying or otherwise conveying potential diagnoses and procedures as determined by the image analysis engine 402 for confirmation, editing, or other modification by the user. Any interaction with the user can use one or more of visual, auditory and tactile methods. All interaction with a user via user input 465 can be recorded in the data capture engine 406.

Most training and/or development of algorithms used in an image analysis system 401 is performed centrally in one or more central training systems 483. Reasons for this include, but are not limited to, one or more of the following: data requirements, processing and/or computational requirements, and necessity for validation of algorithms in a medical environment. At the same time, there is some use for a local algorithm training engine 466 which can use data stored in a data capture engine 406 and which can adjust parameters in and/or modify one or more algorithms as per a local operating system 410.

One example of the use of a local algorithm training engine 466 includes learning preferences for a specific endoscopic system 400. These preferences can include, for example, one or more of: learning preferences for a particular user, making adjustments for a particular case type, and adapting to different components attached to the system. As one or more users make particular adjustments over a plurality of cases, the local algorithm training engine can automatically adjust settings of one or more aspects of the image analysis system 401 and/or one or more components 431-438 of an endoscopic system 400 with which an image analysis system 401 is used. Any changes made by a local algorithm training engine 466 and communicated to the operating system 410 can additionally be communicated between a local operating system 410 and a support center 485. This would enable, for example, the communication of a particular user's preferences to a different endoscopic system 400 if they were to use a different system.

Another example of the use of a local algorithm training engine 466 can include one or more functions described herein as a part of the central training system 483. For example, some preprocessing of information stored in the data capture engine 406 can potentially be done locally, if processing capability allows, to facilitate any training done in a central training system 483. Processing user input 465 as it relates to classifications performed in an image analysis engine 402 can be an example of this.

Another use of information in endoscopic case data contained in the data capture engine 406 after an endoscopic procedure is to automatically annotate one or more images and/or video captured during the procedure to generate annotated images/video 471. In traditional endoscopic systems, a user often captures specific images and/or video during a case, generally by pressing a button on the camera 434, and alternatively through any other method that signals the system to save an image. These images and/or video captures are generally stored in a content management system that is a part of the endoscopic system. These images and/or videos are saved or otherwise preserved in multiple methods including but not limited to one or more of the following: printing on an attached printer, exporting to an electronic medical record system, sending to a patient, sending to a user, and storing in a proprietary system associated with the endoscopic system. To increase the utility of the saved images and/or video, including for the patient, a user or other member of the procedure team often makes annotations describing, for example, location, tissue findings, and/or procedures performed. Information in the endoscopic case data contained in the data capture engine 406 can be used by an image annotation engine 462 to automatically annotate the saved images and/or video using the results of the image analysis engine 402 associated with each image and/or video that is saved. In order to make sure that all annotations correctly represent what the user wants to convey, all classifications and/or information upon which the annotations are created can be confirmed, edited, or otherwise modified by the user via user input 465.

Another use of information contained in the data capture engine 406 after an endoscopic procedure is completed is to automatically extract information from the procedure for case documentation 473. The case documentation 473 can include many types or forms of documentation, including but not limited to one or more of the following: procedure reports, operative reports, nursing reports, anesthesia reports, and codified data in a database. The case documentation 473 can be saved in multiple ways or forms including, but not limited to, one or more of the following: printed records, electronic medical record (EMR) systems, sent electronically in any format, or in a separate database. Endoscopic case data in the data capture engine 406 containing the results of the image analysis engine 402 can be used by a documentation engine 463 to populate appropriate parts of the case documentation 473. Examples of information from case data contained in the data capture engine 406 that can be extracted and sent to the documentation engine 463 can include one or more of the following: patient demographics, user information, facility information, equipment information, pre-procedure diagnosis/es, post-procedure diagnosis/es (e.g., from the tissue ML algorithm 446 and confirmed by user input 465), procedure(s) performed (e.g., from the procedure ML algorithm 447 and confirmed by user input 465), anatomic sublocation data (e.g., from the anatomic sublocation ML algorithm 445), timing data (e.g., case start and finish), supplies used (e.g., fluid), and implants used (e.g., where available from the procedure ML algorithm 447).

The documentation engine 463 can include any necessary interface to format the information from the endoscopic case data in a form appropriate to be sent as (or for) case documentation used in a particular case. In order to make sure that all information utilized for case documentation correctly represents what the user wants to convey, all classifications and/or information which are used for case documentation can be confirmed by the user input 465.

In some endoscopic systems, both the case documentation 473 and annotated images and/or video 471 are saved in the same location. For example, case documentation 473 and any annotated images and/or video 471 may be saved in a paper folder (ie. patient chart) or together in an EMR system 475. In this embodiment, the functionality of the documentation engine 463 and the image annotation engine 462 may be combined, with a common interface combining the otherwise separate interfaces for case documentation and image and/or video annotation.

In the embodiments described above, the use of information from endoscopic case data in the data capture engine 406 for one or more of case documentation 473 and generation of annotated of images and/or video 471 are done local to the endoscopic system 400 through one or more local connections to appropriate storage as described. These connections may be wired or wireless, and may use any protocol.

An alternate method of getting information from the data capture engine 406 for one or more of case documentation 473 and annotation of images and/or video 471 can be done through a central datastore 481. A connection 476 can be provided from the central datastore 481 containing endoscopic case data from one or more endoscopic procedures.

Information from the endoscopic case data of the central datastore 481 can be provided via the connection 476 in one or more formats and/or methods including, but not limited to: printed records, electronic medical record (EMR) system(s) 475, sent electronically in any format, or in a separate database. This configuration that includes the connection 476 from the central datastore 481 can provide or otherwise facilitate a single interface, connection point, or channel for a plurality of image analysis systems 401 to store and access endoscopic case data and communicate it to a repository such as the EMR system 475, rather than each of the plurality of image analysis systems 401 interacting with each other and/or the EMR system 475, etc. via distinct interfaces.

As an illustrative example of this embodiment: a healthcare system may have a unified electronic medical record (EMR) system 475 used by all providers in the healthcare system. At the conclusion of an endoscopic procedure done anywhere in the healthcare system, a user can make any appropriate changes to the endoscopic case data in the data capture engine 406 through user input 465 as described above. The endoscopic case data can be sent to the central datastore 481 and then sent directly via the connection 476 to the EMR system, such that the endoscopic case data is available to all users in the healthcare system. Similar examples can be given for any plurality of endoscopic systems, including but not limited to one or more of: facilities, groups of users, insurance companies, and patients.

The central datastore 481 may be a system that aggregates or otherwise collects endoscopic case data from one or more image analysis systems 401, as well as from additional sources (as described further below). The central datastore 481 can exist in any form, including but not limited to any combination of one or more of the following: a single database in one location, a cloud-based system, references to data in different databases, and references to images and/or videos stored in different systems. The central datastore 481 can aggregate, collect, and otherwise include endoscopic case data from one or more local data capture engines 406 of one or more image analysis systems 401. The central datastore 481 can utilize any combination of standard and/or proprietary protocols and/or formats.

In order to get information from a local data capture engine 406 to the central datastore 481, one or more central interfaces 464 and/or one or more communication channels 482 can be utilized. In one embodiment where connectivity and sufficient bandwidth exists between the local data capture engine 406 and the central datastore 481, the endoscopic case data associated with an endoscopic case can be securely transmitted in real-time and/or at the conclusion of a case. In embodiments where connectivity may present an issue (e.g., limited connectivity or bandwidth), the communication channel 482 of endoscopic case data might include one or more of the following: being stored in a different local site for batch uploading, utilizing a hardware storage device as an intermediary, and using another asynchronous method of communication. Additionally, in embodiments where connectivity is an issue, lower resolution and/or compressed data can be initially sent to enable more timely functionality, with a full dataset later added when transmission allows or via another communication channel 482.

One use of information in endoscopic case data in the central datastore 481 is for developing, testing, refining, validating and the like of central training algorithms by the central training system 483. Data from the central datastore 481 can be used to develop, modify and/or refine ML algorithms 442 of the image analysis engine 402. In this use, the data can be used for one or more of: training, testing and validation of machine learning algorithms. Information in the central datastore can also be used to develop, modify, and/or refine non-machine learning algorithms used in the image analysis system 402. Data in the central datastore can be used to develop, modify, and/or refine algorithms defining functionality for the control engine 404. All types of algorithm development and/or modification (e.g., by the central training system 483, the local algorithm training engine 466) can include user input as needed, including but not limited to one or more of the following: user input 465 where the user interacts with information presented by the image analysis system 401 and user input where the user interacts with a component of an endoscopic system 400 (e.g. manipulating a hand control attached to a pump). The central training system 483 can also include validation functionality to ensure that image analysis algorithms meet any regulatory and/or functional requirements before being used in actual cases.

The central datastore 481, according to some embodiments, can also be accessed by an endoscopic procedure analysis engine 491. The endoscopic procedure analysis engine 491 can be used to provide queries of data contained in the central datastore 481 using any combination of any type of data contained in the central datastore 481, on any set of information from a single data point up through and including the entire datastore. Analysis and calculations can be performed based on endoscopic case data in the central datastore 481 to generate additional data. Operation and functionality of an endoscopic procedure analysis engine 491 is more fully described below in the detailed descriptions of FIGS. 14 and 16.

A support center 485 can provide support to one or more individual image analysis systems 401. As an example, the support center 485 can provide system update data 486, such as to modify functionality of one or more individual image analysis systems 401. Stated otherwise, the system update data 486 can comprise updates to the image analysis system 401 to update any aspect of the image analysis system that is updatable via electronic data over a communication link or other electronic communication channel. Updates provided by the support center 485 to the image analysis system 401 via the system update data 486 can include, but are not limited to: updated and/or new algorithms for the image analysis engine 402, updated and/or new algorithms for the control engine 404, updated and/or new algorithms for the image normalization engine 415, updated and/or new algorithms for the display engine 408, updated data structure and/or functionality for the data capture engine 406, and any other functionality or configuration in the image analysis system 401 that can be modified via a software update, parameter update, settings, preferences, or the like. As a more specific example, when an image analysis system 401 identifies components of an endoscopic system 400 that are new and/or changed from a previous configuration, the operating system 410 can request or otherwise receive updated control algorithms from the support center 485. Modified versions of algorithms and/or preferences related to functionality of an image analysis system 401 can be stored in the support center 485 relating to a grouping, such as according to: user, facility, facility type, healthcare system, clinic, case type, patient population, geographical location, and endoscopic system 400 configuration. When a case is to be performed, any pertinent preferences and/or algorithms pertaining to that case can be received from the support center 485 to optimize functionality of the image analysis system 401 for that case. In addition to updating any function of an image analysis system 401 as needed before a particular case, intermittent updates from the support center 485 can be performed at any time, including under manual and/or automatic control.

System update data 486 can be transferred between the support center 485 and an individual image analysis system 401 using any appropriate method or communication channel. In one embodiment where a real-time connection is available, an image analysis system 401 can query a support center 485 to check for any updates. This can include general updates to any part of the operating system 410. This can also include any preferences and/or specific updates related to, but not limited to, one or more of the following: user, case-type, facility, healthcare system, clinic, geographical location, and endoscopic system 400 configuration. In other embodiments, system update data 486 can be transferred between a support center 485 and an individual image analysis system 401 where a real-time connection is not available, such as by transferring system update data 486 to an intermediary device that can provide the system update data to update the operating system 410 on an intermittent basis. This intermediary device can be any transfer device including, but not limited to: an intermediate computer located at the facility, a remote system not located at the facility, a hard drive which can be manually connected to the image analysis system 401, a USB drive which can be manually connected to the image analysis system 401, and any other device which is capable of storing and/or transferring electronic information. In any embodiment of transferring system update data 486 that utilizes an intermediary device, the intermediary device can also store information from the image analysis system 401 to transfer back to the support center 485 including, but not being limited to: software versions, installed algorithms, endoscopic system configurations, and preferences.

The operating system 410 can include an operating system in the traditional sense, comprising executable instructions, modules, software, and the like that supports basic functions of a computing device, such as managing hardware resources, managing memory, scheduling tasks or processes, executing applications, controlling peripheral interfaces, and the like. For example, the operating system 410 can include a standard operating system to perform standard operating system functions, such as, for example, Microsoft® Windows®, Apple® macOS® or iOS®, Disk Operating System (DOS), UNIX, IRJX, Solaris, SunOS, FreeBSD, Linux®, fliM® OS/2® operating systems, and so forth. The operating system 410 can also encompass the computing platform of the image analysis system 401, including one or more processors, memory, communication interfaces, peripheral interfaces, input/output interfaces, and other computing hardware, as well as the executable instructions, modules, software and the like that supports the computing platform. Further, in a broad sense, the operating system 410 can encompass the algorithms, preferences, software-based functionality, and/or hardware based functionality in the image analysis system 401. The operating system 410 includes any settings and/or preferences in an image analysis system 401 relating to, but not limited to: user, facility, facility type, health care system, clinic, case type, patient population, geographical location, and endoscopic system 400 configuration.

The operating system 410 can include and/or execute in conjunction with one or more processors. The one or more processors may include one or more general purpose devices, such as an Intel®, AMD®, or other standard microprocessor. The one or more processors may include a special purpose processing device, such as ASIC, SoC, SiP, FPGA, PAL, PLA, FPLA, PLD, or other customized or programmable device. The one or more processors may perform distributed (e.g., parallel) processing to execute or otherwise implement functionalities of the present embodiments.

The operating system 410 can include memory, which may include, but is not limited to, static RAM, dynamic RAM, flash memory, one or more flip-flops, ROM, CD-ROM, DVD, disk, tape, or magnetic, optical, or other computer storage medium. The memory may include a plurality of program modules and program data.

The program modules may include all or portions of other elements of the image analysis system. For example, the program modules may include all or portions of one or more of the engines described above, such as the image normalization engine 415, the image analysis engine 402, the control engine 404, the data capture engine 406, the display engine 408, the image annotation engine 462, the documentation engine 463, and/or the local algorithm training engine 466. The program modules may run multiple operations concurrently or in parallel by or on the one or more processors. In some embodiments, portions of the program modules, components, and/or facilities are embodied as executable instructions embodied in hardware or in firmware, or stored on a non-transitory, machine-readable storage medium such as a memory. The instructions may comprise computer program code that, when executed by a processor and/or computing device, causes such to implement certain processing steps, procedures, and/or operations, as disclosed herein. The program modules, components, and/or facilities disclosed herein may be implemented and/or embodied as a driver, a library, an interface, an API, FPGA configuration data, firmware (e.g., stored on an EEPROM), and/or the like. In some embodiments, portions of the modules, components, and/or facilities disclosed herein are embodied as machine components, such as general and/or application-specific devices, including, but not limited to: circuits, integrated circuits, processing components, interface components, hardware controller(s), storage controller(s), programmable hardware, FPGAs, ASICs, and/or the like. Accordingly, the modules disclosed herein may be referred to as controllers, layers, services, engines, facilities, drivers, circuits, and/or the like.

The operating system 410 may include or otherwise interact with input/output interfaces that may facilitate interfacing with one or more input devices and/or one or more output devices. The input device(s) may include a keyboard, mouse, touch screen, light pen, tablet, microphone, sensor, or other hardware with accompanying firmware and/or software. The output device(s) may include a monitor or the display 412, a printer, a speech or text synthesizer, or other hardware with accompanying firmware and/or software.

The operating system 410 may include or otherwise interact with a network/COM interface to facilitate communication with other computing devices (e.g., other image analysis systems, the EMR system 475, the central datastore 481, the central training system 483, the support center 485, and/or networks, such as the Internet and/or other computing and/or communications networks. The network/COM interface may be equipped with conventional network connectivity, such as, for example, Ethernet (IEEE 802.3), Token Ring (IEEE 802.5), Fiber Distributed Datalink Interface (FDDI), or Asynchronous Transfer Mode (ATM). Further, the network/COM interface may be configured to support a variety of network protocols such as, for example, Internet Protocol (IP), Transfer Control Protocol (TCP), Network File System over UDP/TCP, Server Message Block (SMB), Microsoft® Common Internet File System (CIFS), Hypertext Transfer Protocols (HTTP), Direct Access File System (DAFS), File Transfer Protocol (FTP), Real-Time Publish Subscribe (RTPS), Open Systems Interconnection (OSI) protocols, Simple Mail Transfer Protocol (SMTP), Secure Shell (SSH), Secure Socket Layer (SSL), and so forth.

The operating system 410 may include or otherwise interact with a system bus, which may facilitate communication and/or interaction between the other components of the system, including the one or more processors, the memory, the input/output interface, and the network/COM interface, the plurality of engines (the image normalization engine 415, the image analysis engine 402, the control engine 404, the data capture engine 406, the display engine 408, the image annotation engine 462, the documentation engine 463, and/or the local algorithm training engine 466), the plurality of interfaces 421-429, 464.

As can be appreciated, in some embodiments of the image analysis system 401, a subset of elements, features, and functionality may be included. For example, some embodiments may not include a control engine 404, such that image classification for a case may be performed without actually controlling an endoscopic system. Stated otherwise, the image analysis engine 402 may perform image analysis strictly for informational and documentation purposes. As another example, some embodiments may not include an image analysis engine 402. In this example, state and/or external data for a case may be captured and used for functions without utilizing any image data.

While the functionality of an image analysis system 401 as described is generally embodied as connected to and/or controlling an endoscopic system 400 during a case, it can also be embodied virtually with a reduced function set. For example, a user could capture one or more images and/or a video from an endoscopic case. These images and/or video could then be run through a software version of an image analysis system, whether locally (e.g., on a computer or connected to an endoscopic system) or remotely (e.g., uploaded to a website, remote computing system, remote database).

An image normalization engine 415 and an image analysis engine 402 could then analyze the images and/or video from a file as opposed to getting input from a physical video connection. The outputs from the image analysis engine 402 could be saved by a data capture engine 406. The remaining functionality of the entire system could then be used where applicable.

Examples of how this could be useful include, but are not limited to, one or more of the following: calculating case times from the video, extracting tissue information, determining diagnoses, determining procedures, automatically annotating images and/or video, training algorithms, and identifying implants.

Figure 5:
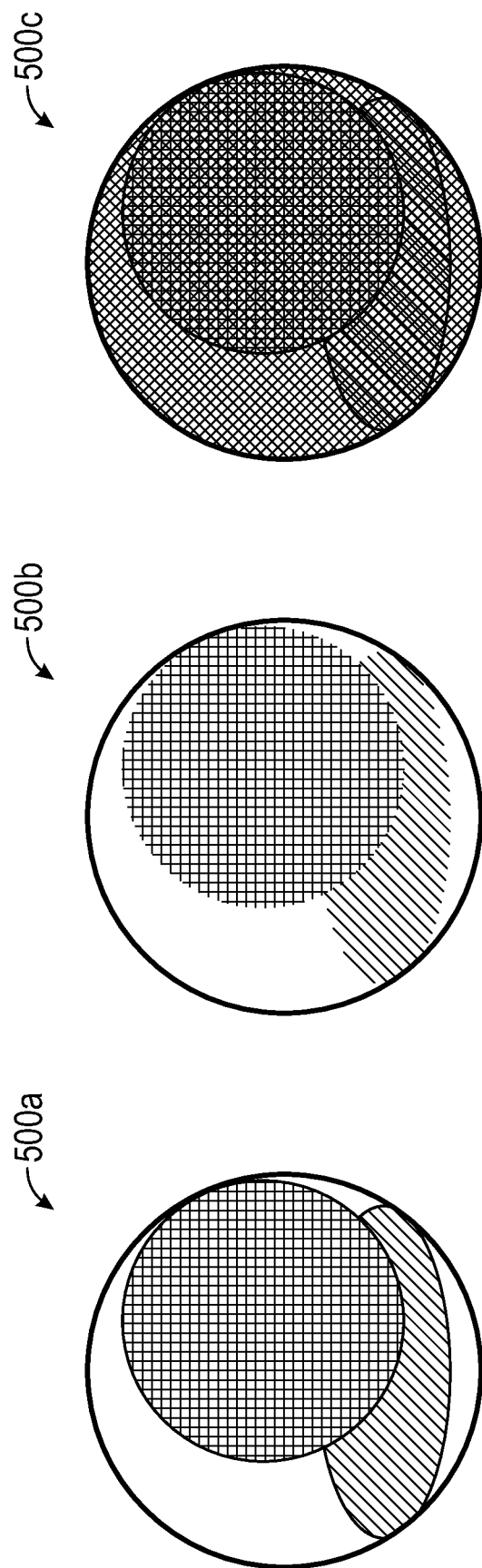
FIG. 5 illustrates examples of endoscopic images that can be analyzed by an image analysis system, according to an embodiment of the present disclosure, to identify characteristics of and/or classify the images, each of which having different characteristics that can be identified.

FIG. 5 illustrates examples of a few different endoscopic images 500a, 500b, 500c that have different characteristics that can be identified by an image analysis engine, according to embodiments of the present disclosure. All three endoscopic images 500a, 500b, 500c depict the same view or perspective of the same area and structural features within the body of a patient, namely a simplified representation of an arthroscopic view of a shoulder with a patient in lateral position, showing a round humeral head over an oval glenoid. Comparison of and discussion of these different endoscopic images 500a, 500b, 500c can illustrate how they have different characteristics. The following discussion of FIG. 5 and the endoscopic images 500a, 500b, 500c is focused on characteristics that may be grouped together in a "general image" category. However, the disclosure is not limited to this single example category. As will be appreciated, an image analysis engine can be configured to identify one or more of a variety of image characteristics. An image characteristic can be any feature, quality, attribute, or the like of the image that the image analysis engine may be able to identify (or otherwise be configured to ascertain).

Notably, as the image analysis engine can determine a characteristic of an image, by corollary the image analysis engine can in some instances be determining a characteristic of a view provided by an endoscope. Identifying and otherwise understanding characteristics of an image provides data from which action can be taken to maintain desirable characteristics and to change less desirable and changeable characteristics, so as to enhance a user experience during performance of an endoscopic procedure and create potential to positively influence outcomes.

An image may have a variety of characteristics, and the image analysis engine may classify the image based on the variety of characteristics, such as according to a dominant, primary, and/or most relevant one or more characteristics. In some embodiments, the image analysis engine may include one or more categories (i.e., categories of characteristics) each including or otherwise organizing multiple characteristics. The image analysis engine may determine a dominant characteristic within each of the one or more categories. In some embodiments, the image analysis engine may include one or more categories (i.e., categories of characteristics and/or classifications) each including or otherwise organizing multiple characteristics to make possible multiple potential classifications. The image analysis engine may classify an image (or otherwise assign an image to a classification) within each of the one or more categories by determining and/or evaluating one or more characteristics of the image. The one or more categories may be predefined, such that the image analysis engine can be configured in advance to determine the one or more characteristics in order to assign the image to a classification in each of the one or more categories. FIG. 5 provides examples of characteristics of images and classification based on those characteristics that pertain to a single category of "general image." As noted above, other potential categories include an "anatomic sub-location" category, a "tissue" category, and a "procedure" category. Other categories are possible and within the scope of this disclosure.

The first image 500a is a simplified representation of an image that is appropriately clear and focused and that may be substantially normal and similar to what the user (e.g., viewer) might see from the hypothetical vantage point of being positioned at the tip of the endoscope providing transmitting light to a camera (or other imager) that captured the first image 500a (or image data from which the first image 500a is generated). In some embodiments, the first image 500a may be analyzed by an image analysis engine to identify that the first image 500a has characteristics such as good, clear, in-focus, and the like. In some embodiments, the first image 500a may be classified as "good" in the general image category. In some embodiments, the classification "good" may be determined based on a plurality of characteristics (e.g., good, clear, in-focus). In some embodiments, the classification "good" may be based on a dominant characteristic (i.e., "good") of the image. In such embodiments, the classifications may correspond or closely map to the characteristics that the image analysis engine is seeking to identify within the general image category. Because the first image 500a is classified as a "good" image in the "general image" category by the image analysis engine, a control engine (e.g., control engine 404 of FIG. 4) may use this as input and make minimal or no changes to the current settings of an endoscopic system (e.g., the endoscopic system 400 of FIG. 4) to maintain the image quality.

The second image 500b is a simplified representation of an image that has a characteristic "out-of-focus." Based on this characteristic (and potentially other characteristics) the image analysis engine may classify the image as "out-of-focus," "focus issue," or the like within the general image category. Because the image analysis engine classifies this as "out-of-focus" in the general image category, a control engine may use this as input to make no changes to a medium management system (e.g., the medium management system 439 of FIG. 4), but instead send a command to a camera (e.g., the camera 434 of FIG. 4) to perform an auto-focus function. Additionally, this classification may also be used by a display engine (e.g., the display engine 408 of FIG. 4) to display a message to a user.

The third image 500c is a simplified representation of an image that has a characteristic "bloody." The third image 500c may appear red, cloudy, or otherwise include blood in the viewing medium or area being addressed that impacts the image and therefore the view of the user and the ability of the user to see the area being addressed and/or tools used for the procedure. Because the image analysis engine classifies this as "bloody" in the general image category, the control engine can use this as input to adjust the pressure and/or flow settings on a medium management system to optimize the image. As the image returns to what the image analysis engine classifies as a "good" image, similar to image 500a in the general image category, the control engine can adjust the pressure and/or flow settings on a medium management system back to nominal settings.

While these are three specific examples of image classifications in a "general image" category, these are exemplary only. Any image characteristics analyzed or otherwise identified by an image analysis engine (and resulting in any classification, potentially in any category) can be a basis for actionable outputs for use in an endoscopic system in a similar manner. Further, any characteristics and/or classifications of images, within any one or more categories, can be captured for later analysis, documentation, image tagging, or presentation on a display during a procedure (even without generating control commands or otherwise modifying the endoscopic system) to enhance utility of image data and thereby enhance user experience and/or patient outcomes.

Figure 6:
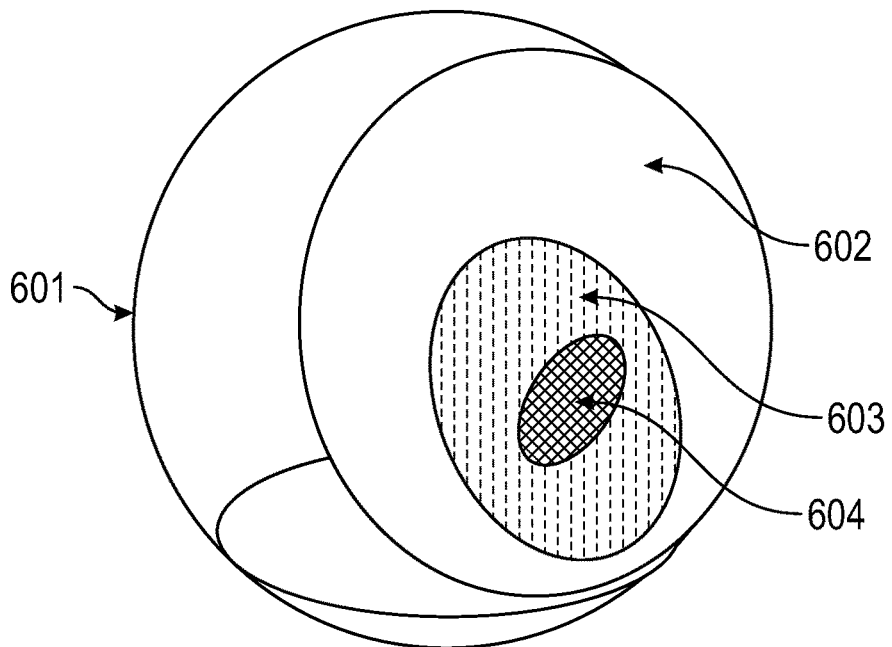
FIG. 6 is another endoscopic image that can be analyzed by an image analysis engine, according to an embodiment of the present disclosure, to identify characteristics of and/or classify the image.

FIG. 6 is another endoscopic image that can be analyzed by an image analysis engine, according to an embodiment of the present disclosure, to identify characteristics of and/or classify the image. FIG. 6 provides for discussion of an example of how an image analysis engine can use combinations of algorithms to analyze or extract information from an endoscopic image or otherwise identify different characteristics of an endoscopic image. In this example, an anatomic sub-location ML algorithm (e.g., anatomic sub-location ML algorithm 445 of FIG. 4) can analyze the image 601 to identify a characteristic "medial compartment of a knee." The structures and/or tissue appearing in the image can, by analysis of the image analysis engine, be recognized as the medial compartment of a knee. Stated otherwise, the anatomic sub-location ML algorithm can recognize the image data as providing a view of the medial compartment of a knee. Other characteristics of the image may also be analyzed or identified. This medial compartment of a knee characteristic can be used to classify the image as "medial compartment of a knee" in an "anatomic sub-location" category.

A classification in the anatomic sub-location category can be used as an input by another ML algorithm, such as a "tissue" ML algorithm (e.g., the tissue ML algorithm 446 of FIG. 4) to narrow characteristics to be analyzed or otherwise sought and/or possible classifications for the image to those applicable to the medial compartment of a knee. In this particular example of FIG. 6, a structure 602 can be analyzed and otherwise identified as having characteristics of a medial femoral condyle and/or classified as a medial femoral condyle in the tissue category. A particular portion 603 of the medial femoral condyle structure 602 can be classified in the tissue category as grade 3 chondromalacia and another portion 604 can be classified in the tissue category as grade 4 chondromalacia 604.

The identified characteristic(s), and classification(s) based on the characteristics may be provided to a control engine, a data capture engine, a display engine, and/or a central datastore for use in the various ways described above to enhance operation of an endoscopic system and/or enhance utility of image data captured during an endoscopic procedure. For example, a control engine can adjust the speed of a motorized device and/or settings on an energy device based on these characteristics and/or classifications. Other possible uses of characteristics and/or classifications determined by an image analysis engine include, but are not limited to one or more of the following: case documentation, image annotation, use and/or storage in an EMR system, data for use by a central training system to develop and refine image analysis algorithms, and use in a reporting system.

Figure 7:
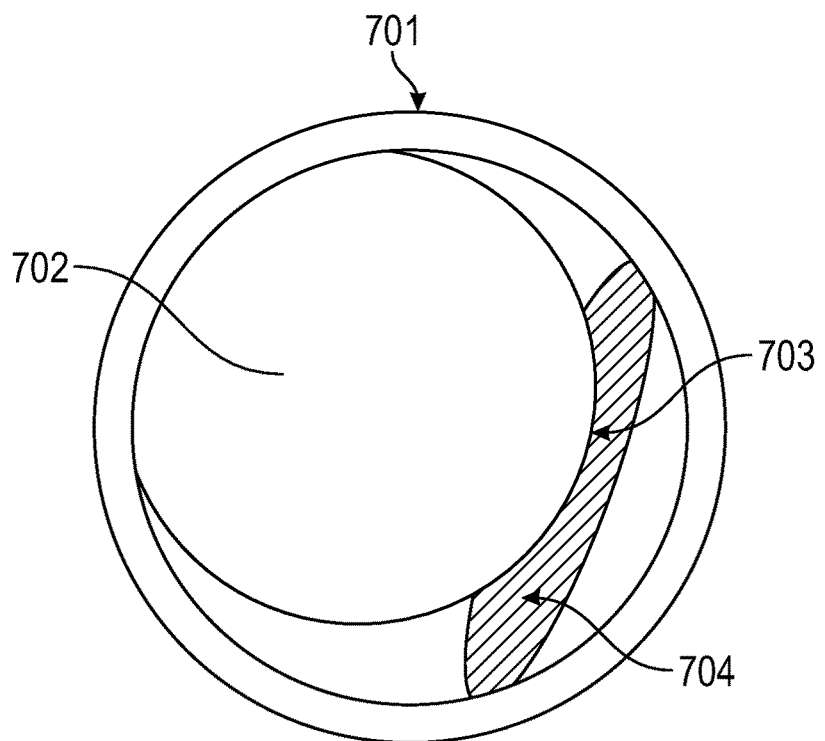
FIG. 7 is another endoscopic image that can be analyzed by an image analysis engine, according to an embodiment of the present disclosure, and demonstrates image characteristics.

FIG. 7 is another endoscopic image that can be analyzed by an image analysis engine, according to an embodiment of the present disclosure, and demonstrates image characteristics. FIG. 7 also provides an example of an endoscopic image 701 that has been differentially enhanced based on results from an image analysis engine. In the current system, image characteristic and/or classification information from one or more ML algorithms of an image analysis engine can be used to differentially apply different types of enhancement to one or more parts of an endoscopic image. In this example of an arthroscopic image of a shoulder, the interface 703 between a humeral head 702 and the glenoid 704 can sometimes be indistinct as they both have similar tissue types (ie. cartilage). If characteristics of the whole image were adjusted, for example by an auto-shutter function, the interface 703 characteristics would not change. In the example shown in FIG. 7, it can be classified as a "glenohumeral joint" sublocation in an anatomic sublocation category and as "cartilage" in a tissue category. This information can be used by a display engine, for example, to differentially highlight the interface 703 between the humeral head 702 and the glenoid 704.

Other examples of types of differential enhancement that are enabled with an image analysis system include, but are not limited to, one or more of the following: adjusting the brightness of a portion of an endoscopic image depending on which part of a body area is currently being viewed (e.g. the suprapatellar pouch of a knee when examining the patellofemoral joint with bright cartilage, as an auto-shutter function uses the brightness of the cartilage to decrease the overall brightness making the suprapatellar pouch dark), highlighting structures (e.g., an artery) with a pulsatile nature moving at the same frequency as a heart rate obtained from external data, increasing contrast and/or gamma in specific ranges for tissues where contrast is otherwise limited (e.g. emphasizing subtle differences in cartilage), and highlighting anatomical structures where additional caution should be used based on sub-anatomic location and/or tissue type (e.g. locations in sub-anatomic areas where nerves tend to run).

The image 701 of FIG. 7 is described above as being analyzed by ML algorithms of an image analysis engine, but alternatively or in addition the image 701 could be analyzed by non-ML image analysis algorithms (e.g., non-ML algorithms 441) of the image analysis system. Non-ML image analysis algorithms that may be used to analyze the image may include color detection, edge detection, color content, contrast, etc. An edge detection image analysis algorithm may be effective to identify the interface 703 between the humeral head 702 and the glenoid 704.

Figure 8:
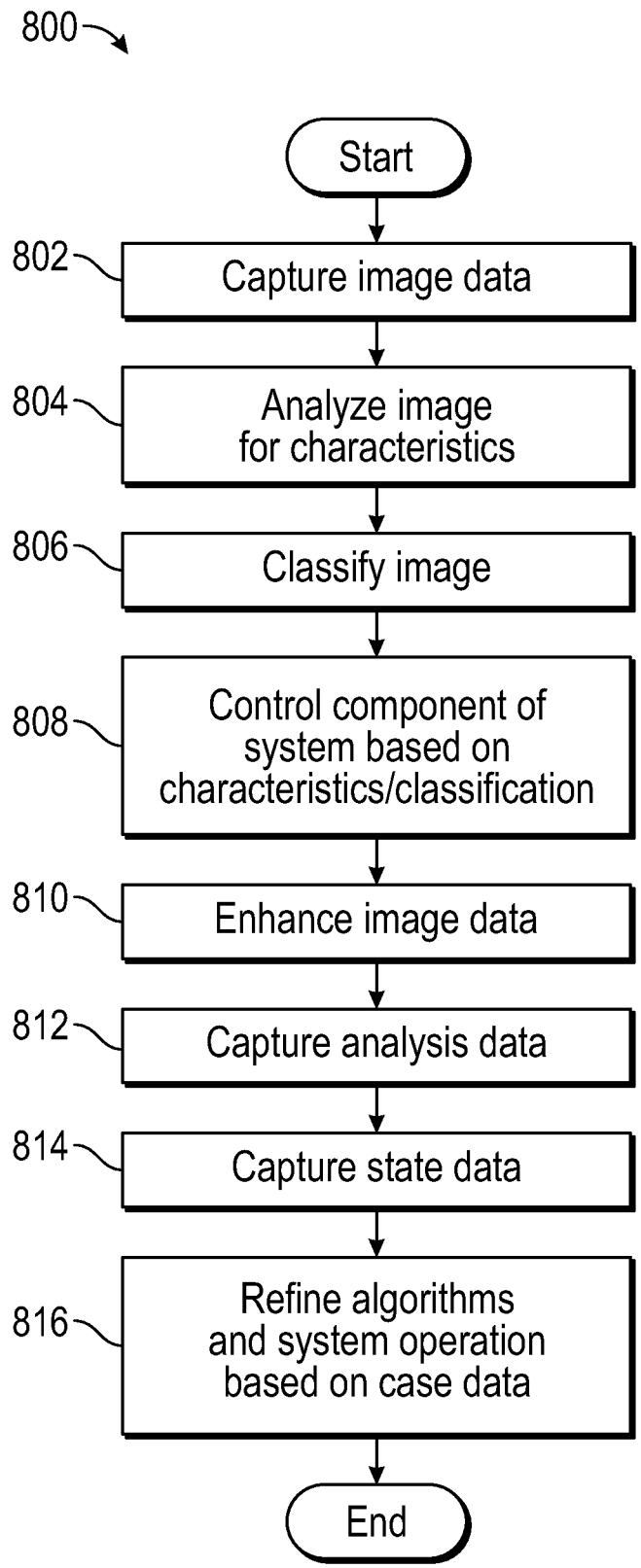
FIG. 8 is a flow diagram of a method of endoscopy, according to one embodiment of the present disclosure.

FIG. 8 is a flow diagram of a method 800 of an endoscopic system, according to one embodiment of the present disclosure. The method 800 can be a computer implemented method of an endoscopic system that may be executed or otherwise performed by one or more of an endoscopic system, an endoscopic image analysis system, and an image analysis engine, according to embodiments of the present disclosure. Image data is captured 802 or received. The image data may initially be video image data. One or more images may be generated from the image data to be analyzed.

The one or more images are analyzed 804 for characteristics, such as by an image analysis engine. The one or more images may be analyzed 804 for predetermined characteristics. The analysis may include identifying one or more characteristics in one or more categories. For example, an image may be analyzed for characteristics in a general image category, an anatomic sub-location category, a tissue category, a procedure category, and any other one or more suitable categories.

The characteristics may be used to classify 806 the one or more images. The classifying 806 of each image may be based on a dominant characteristic of the image. The classifying 806 of each image may be based on a plurality of dominant characteristics of the image. The classifying 806 of each image may be in one or more categories. For example, an image may be classified 806 in a general image category, an anatomic sub-location category, a tissue category, a procedure category, and any other one or more suitable categories. In some embodiments where classifying 806 in multiple categories is based on a dominant characteristic in each category, the classifying 806 may be identical, similar to, or analogous to determining the dominant characteristic as the classification. Stated otherwise, the potential classifications may correspond to the characteristics being analyzed, such that a determination of a dominant characteristic of an image may be tantamount to classifying 806 the image.

Based on one or more identified characteristics and/or classifications, a component of an endoscopic system may be controlled 808. A control engine may utilize the image analysis and/or classification information to provide commands, adjust settings, or otherwise modify operation of one or more components of an endoscopic system. For example, a pump or other medium management system of the endoscopic system may be adjusted to enhance the view captured in future image data through an endoscope, such as by increasing a target flow and/or a target pressure of the viewing medium to address a cloudy characteristic or bloody characteristic in the viewing medium. When the cloudiness or bloodiness is resolved by the adjustment, the pump or other medium management system may be adjusted to maintain the ameliorated view. As another example, a camera may be directed to autofocus to resolve an out-of-focus characteristic in the image data. Other components of the endoscopic system can be similarly controlled, as described elsewhere herein and/or according to adjustability or other manipulability of such other components.

Alternatively or in addition to controlling components of the endoscopic system, the results from the analysis and/or classification of an image can be utilized to enhance 810 image data by being provided to a display. Information pertaining to the characteristics and/or classification of an image can be captured 812 as endoscopic case data by a data capture engine that may collect endoscopic case data for a record of the case. The case data (including the characteristic(s) and/or classification(s) of an image) may alternatively or in addition be provided to a display engine, a documentation engine, an image annotation image, a local algorithm training engine, and to a central datastore. The case data can be provided to a display engine for enhancing 810 rendering of image data to the user and/or procedure team during an endoscopic procedure. The case data can be provided to a documentation engine for use in case documentation, such as in a medical record (e.g., EMR) of a patient and/or for discharge paperwork. The case data can be provided to an image annotation engine for automatic image annotation, again such as in a medical record (e.g. EMR) of a patient and/or for annotation of images and/or video provided to a patient. The case data can be provided to a local algorithm training engine for development, modification and/or refinement of image analysis algorithms. The case data can be provided to a central datastore where it can be used by a central training system to develop, modify, and/or refine image analysis algorithms centrally (e.g., using case data from a plurality of endoscopic systems) or provided for documentation and/or image annotation.

State data of the endoscopic system may also be captured 814. The endoscopic system (e.g., an image analysis system, image analysis engine and/or a control engine) may include interfaces to one or more components of the endoscopic system. These interfaces may provide control or other configuration data to the one or more components and may facilitate query or other receipt of configuration data or other state data of the one or more components. In addition, user input may be received that may affect a state of the endoscopic system. This state data may be captured in the endoscopic case data along with the image analysis 804 results (e.g., one or more characteristics of an image) and/or image classifying results (e.g., one or more classifications of an image). The state data may be similarly utilized to enhance utility of image data or to otherwise enhance utility of the endoscopic system.

The method 800 may also include refining 816 algorithms and/or system operation based on the case data. The case data, including state data, the image analysis 804 results (e.g., one or more characteristics of an image) and/or image classifying results (e.g., one or more classifications of an image), any case identifying data, any external data, and/or any user input, may be utilized to develop, modify, refine and otherwise enhance image analysis algorithms (both non-ML algorithms and ML algorithms) and improve operation of one or more components individually or collectively in the endoscopic system.

As can be appreciated, embodiments of the present disclosure may include a subset of the steps outlined in the method 800 of FIG. 8. Other embodiments of the present disclosure may include additional steps, details, and/or features beyond those articulated in FIG. 8. Any combination or ordering of actions, details, and features that are described herein with reference to other embodiments, including in other figures and not in other figures, may be included in the method 800 of FIG. 8.

Figure 9:
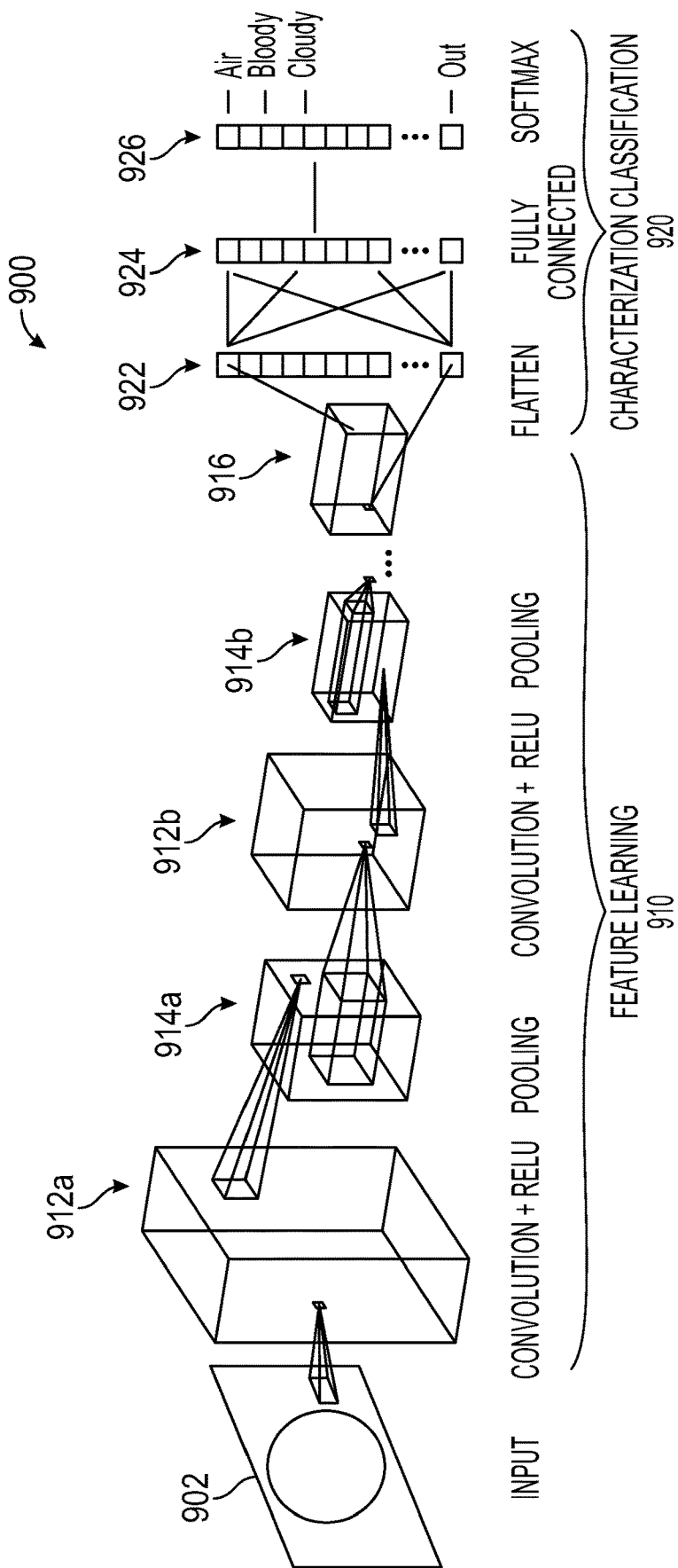
FIG. 9 is a schematic diagram of a convolutional neural network (CNN) that can be used in a machine learning (ML) image analysis algorithm of an image analysis system, according to one embodiment of the present disclosure, to identify characteristics of an image and/or classify an image.

FIG. 9 is a schematic diagram of a convolutional neural network (CNN) 900 that can be used in a machine learning (ML) image analysis algorithm of an image analysis system, according to one embodiment of the present disclosure, to identify characteristics of an image and/or to classify an image. FIG. 9 shows an example of how a convolutional neural network can be used to determine general image characteristics of an arthroscopic image and/or classify the arthroscopic image. An endoscopic image 902 is received at an image analysis engine (e.g., image analysis engine 402 of FIG. 4), for example, from an image normalization engine.

A first stage is a feature learning stage 910 to learn or extract features of the endoscopic image. There can be multiple layers in the feature learning stage 910, including one or more convolution layers 912a, 912b, which may include (e.g., be immediately followed by) an activation function such as a Rectified Linear Unit (ReLU) activation function (or simply ReLU function). Each of the convolution layers+ReLU function 912a, 912b can extract features from the endoscopic image by using a kernel which is passed over the image. The ReLU activation function is used as a rectifier to change all values that are negative after the convolution layer to a zero value.

The multiple layers in the feature learning stage 910 can also include one or more pooling layers 914a, 914b. In each pooling layer 914a, 914b, the resulting matrix from the convolution layer+ReLU function 912a, 912b is downscaled to reduce the pixel density. Images can contain a large amount of data which can be computationally very intensive. Pooling allows retention of pertinent features but also allows for decrease in the amount of data necessary to process. The combination of a convolution layer+ReLU function 912a, 912b and a pooling layer 914a, 914b forms a layer of the CNN, and one or more of these layers can be used as necessary in the feature learning stage 910.

Although the feature learning stage 910 of the CNN 900 of FIG. 9 includes a pair of convolution layers+ReLU functions 912a, 912b and a pair of pooling layers 914a, 914b, other combinations are possible as known in the art of ML, such as one convolution layer+ReLU function and one pooling layer, or three of each, or four of each, etc. The CNN 900 can include any number of convolution layers+ReLU functions and pooling layers to simplify or reduce the image data set and appropriately learn, extract, and otherwise retain features that can be used at the next stage to characterize and/or classify the image.

A second stage 920 is classifying the image 902. The first part of this involves flattening the output of the feature learning section into a vector 922. There is another fully connected layer 924 which contains weighted links to all of the variables in the flattened vector. In some embodiments, there can be multiple additional fully connected layers (also known as hidden layers), which give the neural network of the second stage a depth (i.e., deep learning). Finally, there is a softmax function 926, which is an activation function with an output corresponding to each possible classification to which the image can be assigned within a particular category.

The weights of various parameters in the CNN are determined by training, as will be described. Because the training part is computationally intensive and generally requires significant data to be most accurate, it is generally done centrally as described in other figures. Once the parameters are determined, the actual classification of images is computationally less intensive, and can be done in an individual image analysis system itself.

While this example of a CNN 900 is for a general image category of characteristics of air, bloody, cloudy, etc., with a resultant classification of one of air, bloody, cloudy, etc., similar training can be done for any category which can apply to an endoscopic image, where the resultant classification is useful for endoscopic procedures. Examples of other ML algorithms (which may involve a CNN) include, but are not limited to, one or more of the following: anatomic sublocation, tissue classification, and procedure. Other categories of classifications where a visual difference can be appreciated by a user can also be incorporated as part of an image analysis system.

Further, the CNN 900 is simply one example of a computing system or framework for a ML algorithm to identify characteristics of an image and/or classify an image. Other forms of neural networks may be used, for a general image category or any other category of characteristics and/or classifications, including but not limited to one or more of: a graph neural network, a capsule neural network, and a recurrent neural network.

Figure 10:
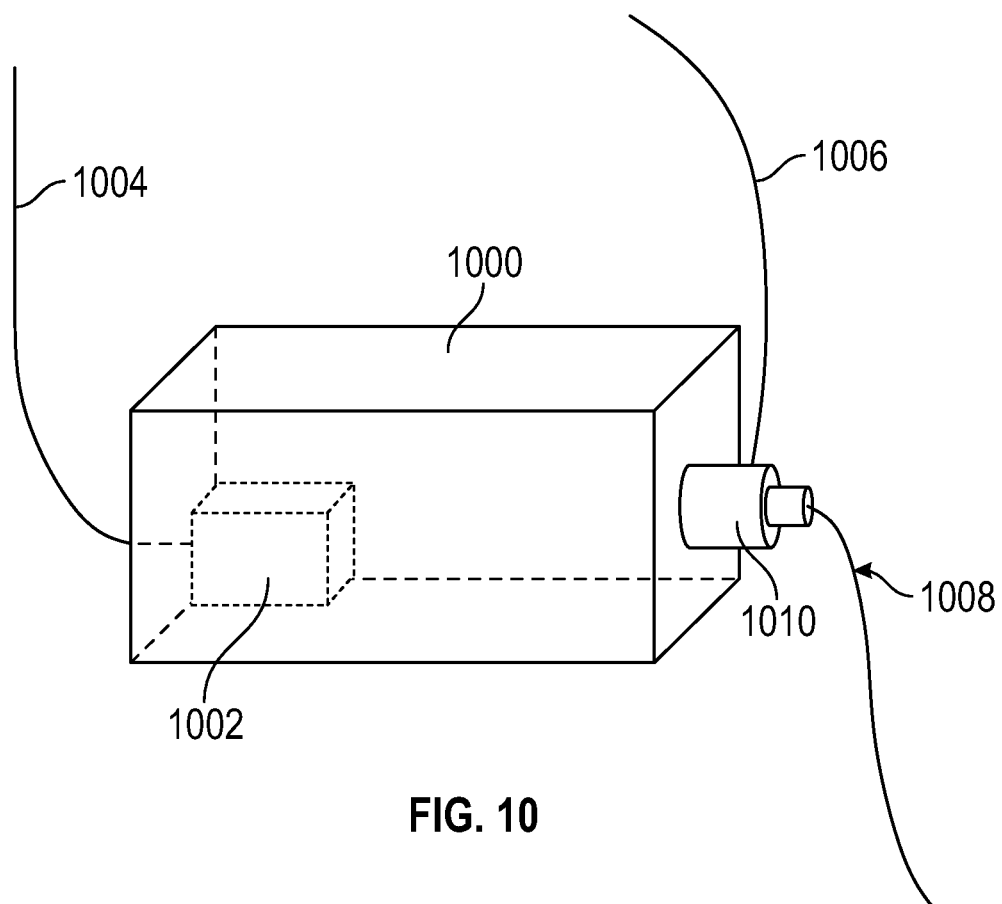
FIG. 10 is a diagram of a component of an endoscopic system, according to one embodiment of the present disclosure, illustrating interfaces for controlling the component.

FIG. 10 is a diagram illustrating a controllable component 1000 of an endoscopic system, according to one embodiment of the present disclosure. The controllable component 1000 can be controlled based on one or more outputs of an image analysis system. The controllable component 1000 can be any component of an endoscopic system that can be controlled or otherwise have a state change during an endoscopic procedure, including but not limited to one or more of: a medium management system (e.g., pump, insufflator, outflow control), electrocautery instrument component, motorized device component, light source, camera, and delivery device component. FIG. 10 provides examples of various ways to interface or otherwise interact with the component 1000 in an endoscopic system. In some components, there are one or more ports 1002 available, generally on the back of the component 1000. These ports can include any type of interface, examples of which include, but are not limited to, one or more of the following: RS-232, universal serial bus (USB), other configurations of serial port and/or parallel port, and proprietary ports. In the example shown in FIG. 10, a physical connection 1004 between an image analysis system and the component 1000 is shown, but any wireless protocol can also be used.

The wired and/or wireless connection 1004 can support any available protocol or interface, and can be used for any function including, but not limited to, one or more of the following: setting parameters in the component, querying parameters in the component, and collecting state information about the component. By performing serial queries of a component, the image analysis system can determine when a user makes any changes to any settings on the component, including, but not limited to, any changes made using one or more of the following: a button on the component 1000, a touch screen on the component 1000, a controller connected to the component 1000 that is manipulated from a sterile field (e.g. a hand controller for an arthroscopy pump), and a controller connected to the component that is manipulated from a non-sterile field (e.g. a foot controller for a motorized device).

In some components, there is not a specialized port 1002 available for connection to an image analysis system and/or there is not a defined data protocol that an image analysis system can utilize to communicate with the component

1000. An alternative or additional method of providing an interface with a component 1000 of an endoscopic system is to use a port that accepts a connection 1008 of an external controller. An example of this type of interface is a port on the front of a medium management system component to which a sterile hand controller and/or a foot controller is normally plugged in, and which can receive input from a user to make changes to settings in the component 1000. A jumper 1010 can be used into which the controller can be plugged 1008 and/or which can plug into the port on the component component 1000 into which the controller is normally plugged. The traditional use of the controller can be maintained by passing any command sent by one or more users from the controller connection 1008 to the component 1000.

The jumper 1010 can couple to a connection 1006 to an image analysis system. The connection 1006 allows the image analysis system to send commands to the component 1000. The jumper 1010 can receive a command from the image analysis system through a wired and/or wireless connection 1006, and the jumper 1010 can activate appropriate pins on the port on the component 1000 as if one or more users sent the command manually.

Another use of the jumper 1010 can be for capturing any commands sent by a user. Because the controller is coupled to the connection 1008 to the jumper 1010, in addition to passing any commands along to the component 1000, the commands can also be sent to the image analysis system via the connection 1006 of the jumper 1010 to the image analysis system. This connection 1006 allows for capture of any changes made to the state of the component 1000 by one or more users for use by other parts of the image analysis system. Examples of these uses include, but are not limited to, one or more of the following: updating information displayed by a display engine, feedback for further functionality of a control engine, incorporation into case documentation, and information used as inputs for training algorithms.

FIG. 11 is a display 1101 of an endoscopic system, according to one embodiment of the present disclosure, as may be used during an arthroscopic case. FIG. 11 illustrates the display 1101 presenting additional information as it pertains to the operation of the image analysis system. The display 1101 can either be a primary display monitor or a secondary display monitor. In embodiments where the display 1101 is a primary display monitor, the additional information may be presented to the sides of the endoscopic image 1104 as shown. In embodiments where the display 1101 is a secondary display monitor, the additional information can be displayed in any other appropriate way of presenting information. In FIG. 11, the display 1101 is shown as a primary display and presents an image 1104 showing a view of the area being addressed, including a tool interacting with tissue in the area being addressed. Because of the difference in aspect ratios between the viewable area of a rectangular screen 1102 and most endoscopic images 1104 (which are generally circular), there is space for a display engine to add additional information pertinent to the use of the image analysis system. The additional information may be derived from endoscopic case data captured by a data capture engine of an image analysis system, according to embodiments of the present disclosure.

One example of additional information is shown on the left of FIG. 11 in the two circular-type dial portions 1106, 1108. In this example, information relating to a medium management system as used in arthroscopy is shown. In the first circular-type dial portion 1106 an arc is shown. The numbers at the end of the arc show minimum and maximum values for pressures within which a control engine can make automatic adjustments to target pressures. These minimum and maximum values can be set by the user to keep operating parameters in a safe range. An actual setting of the medium management system for a target pressure within that range can be shown by a number in the middle of the arc, as well as by shading in the arc itself.

In the second circular-type dial portion 1108, an example of a target flow rate on a medium management system as used in arthroscopy is shown. In this example, the values for target flow range from a minimum of "OFF" to a maximum of "HIGH." The current value of the target flow in this example is shown as "LOW," with a shaded portion of the arc one-third shaded to graphically represent the current value, from possible values of "OFF-LOW-MEDIUM-HIGH".

Other examples of additional information that can be shown are results of image analysis by an image analysis engine of an image analysis system. In the bottom right corner are graphics 1110 (e.g., bars, graphs, or other dials) that represent a sample output of a general image ML image analysis algorithm (e.g., general image ML algorithm 444 of FIG. 4), where the image is analyzed for characteristics and/or classified as one or more of: Air, Bloody, Cloudy, Focus, Good, and Out-Of-Area.

These are just a few examples of information from endoscopic case data related to use of the image analysis system that can be displayed on a primary and/or secondary display 1101. Other examples of information that can be displayed include, but are not limited to, one or more of the following: any other output from one or more machine-learning algorithms; outputs of one or more non-machine learning algorithms; any external data collected and/or used for control of an endoscopic system; any state information concerning one more components of an endoscopic system gathered and/or modified by a control engine; any operating parameters utilized by an image analysis system; messages relating to the function of an image analysis system; information contained in and/or calculated from a data capture engine; and any information displayed for and/or obtained as a part of user input for an image analysis system.

Figure 12:
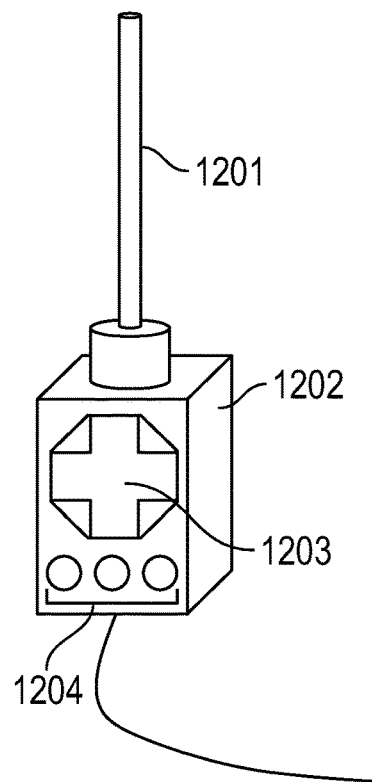
FIG. 12 is a perspective view of a camera incorporating enhanced user input components, allowing the user to select, modify, and interact with information on the display without having to move their hands from the camera to a secondary input device.

FIG. 12 is a perspective view of a camera 1202 coupled to an endoscope 1201 and incorporating enhanced user input components 1203, 1204 that allow the user to select, modify and interact with information on the display without having to move their hands from the camera to a secondary input device. The camera 1202 of FIG. 12 provides an example of how one or more buttons and/or other methods of capturing user input can be used as a part of an endoscopic system incorporating an image analysis system for functions relating to the image analysis system. FIG. 12 shows an endoscopic camera 1202 that is attached to an endoscope 1201 that is used to view an area to be addressed inside the body of a patient. User input components disposed on the camera 1202 can include one or more of the following: single function buttons 1204, multidirectional buttons 1203, touch sensitive pads, and any other way to capture tactile user input.

An example of how this user input can be incorporated in an image analysis system is based on the architecture, such as described above with reference to FIG. 4, in which a control engine (e.g., control engine 404 of FIG. 4) is connected to a plurality of components in an endoscopic system. User input from one or more buttons 1203, 1204 on the camera 1202 can be processed by the control engine and used, for example, to adjust settings on a medium management system (e.g., medium management system 439 of FIG. 4) which is also connected to the same control engine. Settings on a motorized device, such as a shaver and/or burr, can also be modified through buttons on the camera 1202 in a similar manner. In effect, any input to any single component of an endoscopic system 400 that is coupled to a control engine can be used to control any other component of the endoscopic system 400. The control engine and/or the data capture engine of an image analysis system facilitates communication of such user input at any coupled component to any other coupled component.

Another example of how capturing user input on one component of an endoscopic system can be used for other functions in an image analysis system includes interacting with, confirming and/or modifying information displayed by a display engine (e.g., display engine 408 of FIG. 4) on a primary and/or secondary display. This information can be anything related to functionality of the image analysis system as described previously in the detailed description of FIG. 11.

Figure 13D:
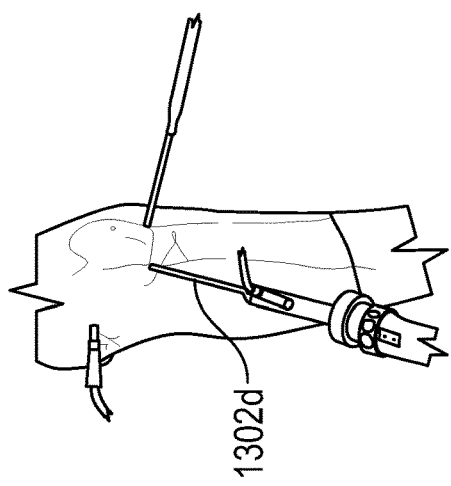
FIGS. 13A, 13B, 13C, 13D, and 13E depict various endoscopic procedures that may be performed utilizing embodiments of the present disclosure.
Figure 13E:
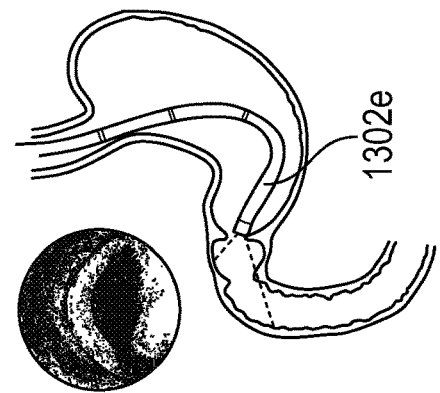
Figure 13C:
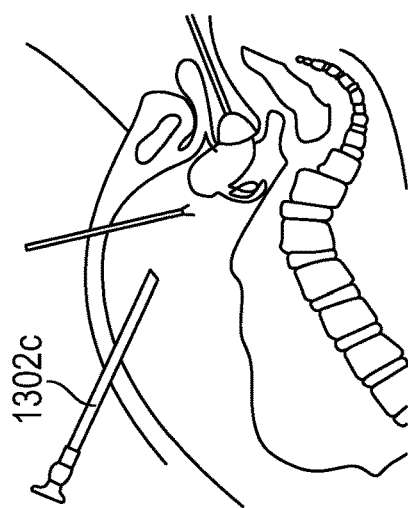
Figure 13A:
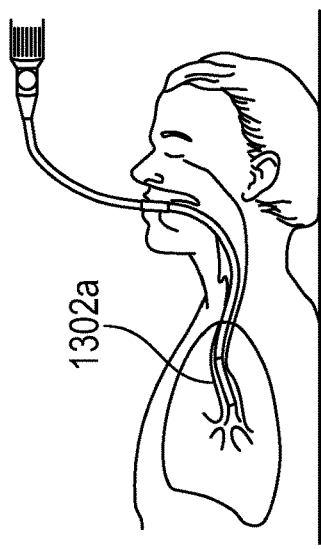
Figure 13B:
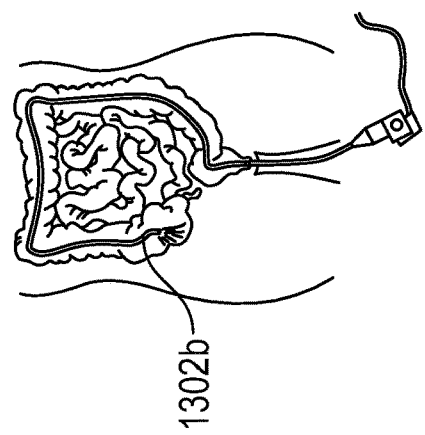

FIGS. 13A, 13B, 13C, 13D, and 13E depict various endoscopic procedures that may be performed utilizing embodiments of the present disclosure. FIG. 13A illustrates a bronchoscopy (or respiratory endoscopy) procedure, including a bronchoscope 1302*a* (or an endoscope 1302*a*) positioned into and through the trachea of a patient and into the lung at an area to be addressed. FIG. 13B illustrates a colonoscopy procedure, including a colonoscope inserted through the anus of a patient and extending the length of the colon of the patient. FIG. 13C illustrates a laparoscopy procedure, including a laparoscope 1302*c* inserted into the abdomen of a patient. FIG. 13D is an arthroscopy procedure, including an arthroscope 1302*d* positioned in the knee of a patient. FIG. 13E is a gastroscopy procedure, including a gastroscope positioned into the stomach of a patient. FIGS. 13A-13E are merely illustrative of some examples of endoscopy that may be performed with endoscopic systems according to embodiments of the present disclosure. Other forms of endoscopy may also be performed utilizing embodiments of the present disclosure, including but not limited to: anoscopy, colposcopy, cystoscopy, esophagoscopy, laryngoscopy, neuroendoscopy, and proctoscopy.

Figure 14:
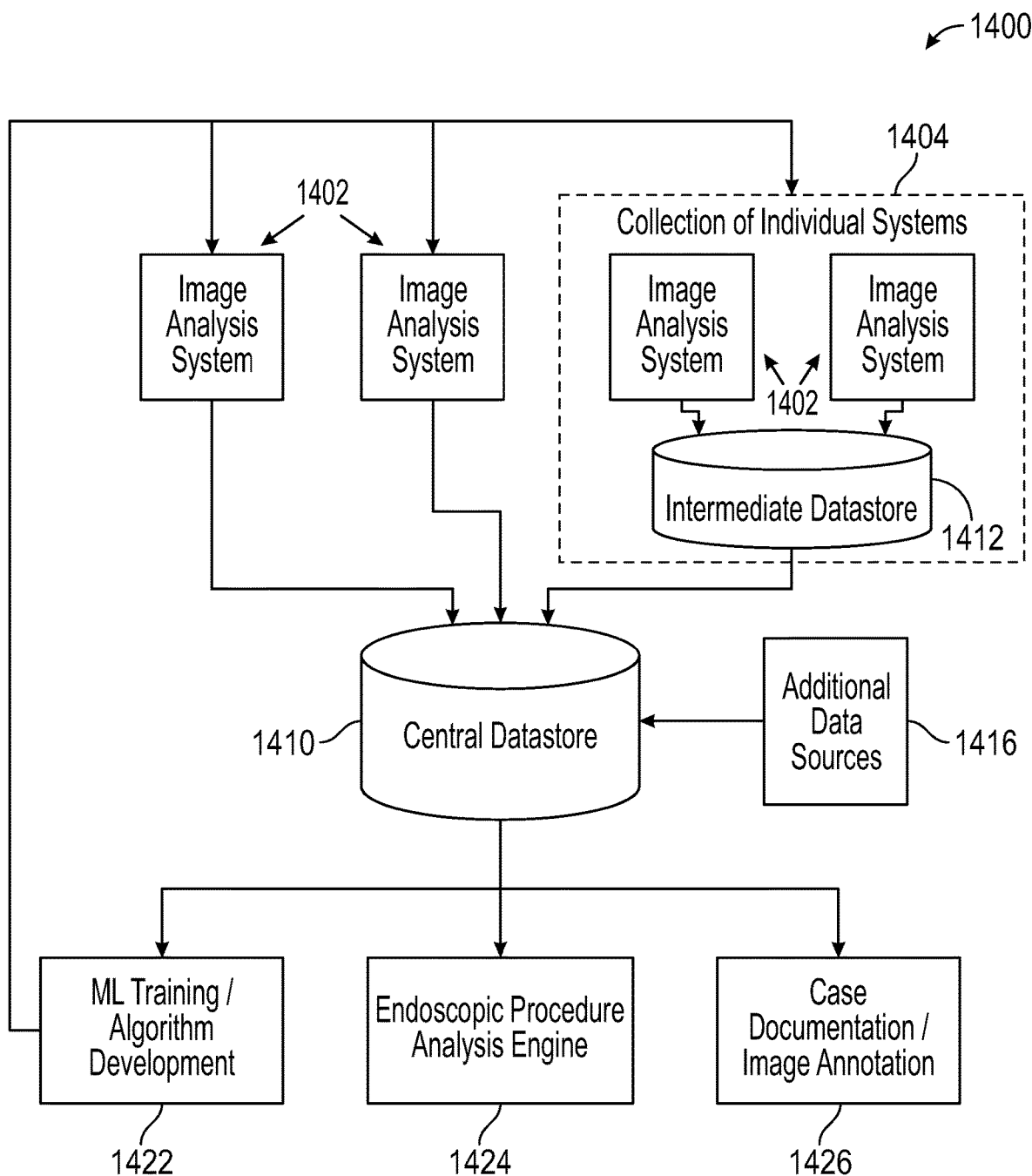
FIG. 14 is a schematic block diagram of an endoscopic image analysis network, according to another embodiment of the present disclosure.

FIG. 14 is a diagram of an image analysis network 1400, according to one embodiment of the present disclosure. The image analysis network 1400 includes a plurality of individual image analysis systems 1402 and/or collections 1404 (or groupings) of image analysis systems 1402, such as at a clinic or within a facility or healthcare system, that can be networked in communication (e.g., wired, wireless, Internet) together and/or to a central datastore 1410. The diagram of FIG. 14 illustrates relationships between image analysis systems 1402 and the central datastore 1410, which can be a system that captures and/or utilizes information from one or more individual image analysis systems 1402, 1404 (e.g., each of an endoscopic system that can be utilized by a procedure team during an endoscopic procedure).

The multiple image analysis systems 1402 may be identical, similar to, or analogous to the image analysis system 401 of FIG. 4. An image analysis system 1402 may be embodied in an image analysis component that is identical to, similar to, or analogous to the image analysis component 150 in FIG. 1 or the image analysis component 350 of FIG. 3. An image analysis system 1402 may be integrated with another component of an endoscopic system, such as a content management system. An image analysis system 1402 may be a virtual system implemented in a cloud computing environment (e.g., as a virtual server) that is in electronic communication with other components of an endoscopic system via a network. A virtual system may have reduced control features or entirely lack control features, but image data (e.g., videos, images) of procedures or cases may be uploaded to have the image analysis performed virtually and to contribute endoscopic case data.

Several individual image analysis systems 1402 are shown in FIG. 14, but these are only representative. The number of individual endoscopic systems 1402 can range from one to a number limited only by the number of installed systems. One or more individual image analysis systems 1402 are connected to one or more central datastores 1410, where endoscopic case data from each of the one or more individual image analysis systems 1402 can be aggregated or otherwise collected.

In some situations, there may be a collection 1404 of individual image analysis systems 1402. This collection 1404 may be one or more image analysis systems located in, but not limited to, one or more of the following: a hospital, a clinic, a surgical center, a healthcare system, a geographical region, and a user group. In a collection 1404 of individual systems 1402, there may be a common connection to a central datastore 1410, which can alternatively include an intermediate datastore 1412. An example of this embodiment might be a surgery center with poor connectivity from individual procedure rooms or operating rooms where data from one or more individual image analysis systems 1402 might be temporarily stored in an intermediate datastore 1412 before being communicated along to a central datastore 1410.

The central datastore 1410 can be a system that receives endoscopic case data for one or more cases performed using one or more image analysis systems 1402. While there is one central datastore 1410 shown in the figure, there can be a plurality of central datastores 1410 as may be desirable or as necessary. These may include, but not be limited to, one or more of the following: multiple central datastores divided for operational efficiencies, multiple central datastores for security and/or redundancy, cloud-based central datastores, and central datastores defined for any grouping of one or more image analysis systems 1402 based on, but not limited to, one of more of the following: a hospital, a clinic, a surgical center, a healthcare system, a geographical region, and a user group. While there may appear to be some similarity between an intermediate datastore 1412 and a central datastore 1410, an intermediate datastore 1412 may functionally store data only temporarily to pass further along, whereas information in a central datastore 1410 includes uses, functionality, and/or purposes described below.

In addition to storing information from one or more individual image analysis systems 1402, whether directly or from a collection 1404 of individual systems 1402, a central datastore 1410 can also receive information from additional data sources 1416. Examples of this include, but are not limited to, one or more of the following: references to images and/or videos stored outside the central datastore, outcomes data and/or other information collected after the end of an individual procedure and/or case, groupings based on any characteristic, demographic information not available at the time of a case and/or procedure, and information contained in an electronic medical record.

The data contained in a central datastore 1410 can include endoscopic case data that can be used for multiple purposes including, but not limited to, one or more of the following: development of machine learning and/or non-machine learning algorithms 1422, as a source of data for an endoscopic procedure analysis engine 1424, and for case documentation and/or image annotation 1426, including in an electronic medical record.

As described below in greater detail, data (including endoscopic case data from a plurality of image analysis systems 1402) stored in a central datastore 1410 can be used for ML training and/or other algorithm development 1422. For example, a central training system (e.g., central training system 483 of FIG. 4) may include a development engine for training, refining, modifying, etc. image analysis algorithms. This central training system may access, receive, or otherwise train ML algorithms utilizing data from the central datastore 1410. The ML algorithms of the image analysis engine(s) of the image analysis systems 1402 may be developed and/or refined by the central training system, which can process large quantities of data through a set of training algorithms. Since the plurality of image analysis systems 1402 can eventually generate millions of images with information about the characteristics of those images, the ongoing training can continue to refine and/or enhance ML algorithms, for example to become more accurate, to identify new characteristics, classify in new classifications, and organize characteristics and/or classifications in new categories, etc.

The training and development 1422 of ML algorithms and other image analysis algorithms may be done centrally, such as by a central training system, so that endoscopic case data from multiple endoscopic systems 1402 (which could number tens of thousands or millions of cases) and/or a subset can be used to train very accurate algorithms in a central location for the benefit of any or all of the individual image analysis systems 1402. These modified training algorithms can be tested, which can be done by using a percentage of training data (where an image's characteristics are "known") to train, and a smaller percentage as test data to make sure the updated algorithms are accurate. These algorithms can then be incorporated back into individual image analysis systems 1402.

An endoscopic procedure analysis engine 1424 can use one or more algorithms to analyze, extract, manipulate, and/or otherwise use data (e.g., endoscopic case data) stored in a central datastore 1410 to generate one or more types of additional data for reports, analyses, statistics, and/or information regarding endoscopic cases. Any data thereby generated by the one or more algorithms can be combined with any additional information generated from standard queries of the central datastore 1410. Any use of the central datastore 1410 can include any combination of data, including any set of information from a single data point up through and including the entire data contents from one or more central datastores 1410.

An example of how an endoscopic procedure analysis engine 1424 can be used to generate new data is determining endoscopic case times by analyzing information from an image analysis engine (e.g., image analysis engine 402 of FIG. 4) as stored in a central datastore 1410 as endoscopic case data. An endoscope may be introduced into a patient and removed one or more times throughout an endoscopic procedure. A general image ML algorithm (e.g., general image ML algorithm 444 of FIG. 4) can be used, for example, to determine a characteristic and/or classification of an image, including when an image is considered "out" of the patient. A series of one or more time-stamped outputs of the image analysis engine, including a general image classification, can be stored in the central datastore 1410. The time associated with the first transition from an image classified as "out" in a general image category to one considered in a patient can be considered a start time, while the last transition from an image considered one of in a patient to "out" can be considered an end time, with the difference between these times considered a case time.

Another example of how an endoscopic procedure analysis engine 1424 can be used to generate new data is determining average pump pressures in an arthroscopic case. During an arthroscopic case, pressures can vary depending, for example, on a need to clear a field of view and/or control bleeding. At other times, flow may be turned off entirely including, for example, when an arthroscope associated with an inflow cannula is removed from the joint. In this case, time-stamped information from a control engine (e.g., control engine 404 of FIG. 4) can be used in combination with information from an image analysis engine to determine an average pressure. A series of actual pressures as measured by a medium management system (e.g., medium management system 439 of FIG. 4), generally obtained by a control engine, and as stored in a central datastore 1410 can be analyzed to calculate an average pressure. Because the flow might be turned off at times when the arthroscope is outside the patient, information from the image analysis engine can be used to determine states when the image is classified as "out" such that pressure readings associated with these states are not included in the analysis.

While these are two specific examples, an endoscopic procedure analysis engine 1424 can be used to analyze any combination of and/or type of endoscopic case data stored in the central datastore 1410. This can include new data generated by one or more algorithms within the endoscopic procedure analysis engine 1424 and/or any query of data stored in the central datastore 1410. Analysis and/or queries can be based on any set of information in the central datastore 1410 including, but not limited to, one or more of: facility, surgeon, procedure, date range, healthcare system, and geographical area.

The data collected and stored at a central datastore 1410 can also be used for case documentation and/or image annotation 1426. An image analysis system 1402 may include local connections to provide documentation and/or annotations for images, such as in a medical record (e.g., EMR). Rather than communicating case data directly from the image analysis system 1402, an alternate method of communicating information for documentation and images and/or video annotation can be done through the central datastore 1410. Information from the endoscopic case data of the central datastore 1410 can be accessed or otherwise received by a documentation engine (e.g., documentation engine 463 of FIG. 4) that can provide case data and/or information therefrom in one or more formats and/or methods including, but not limited to: printed records, electronic medical record (EMR) system(s), sent electronically in any format, or in a separate database. The central datastore 1410 can provide or otherwise facilitate a single interface, connection point, or channel for a plurality of image analysis systems 1402 to store and access endoscopic case data and communicate it to documentation and/or image annotation.

Figure 15:
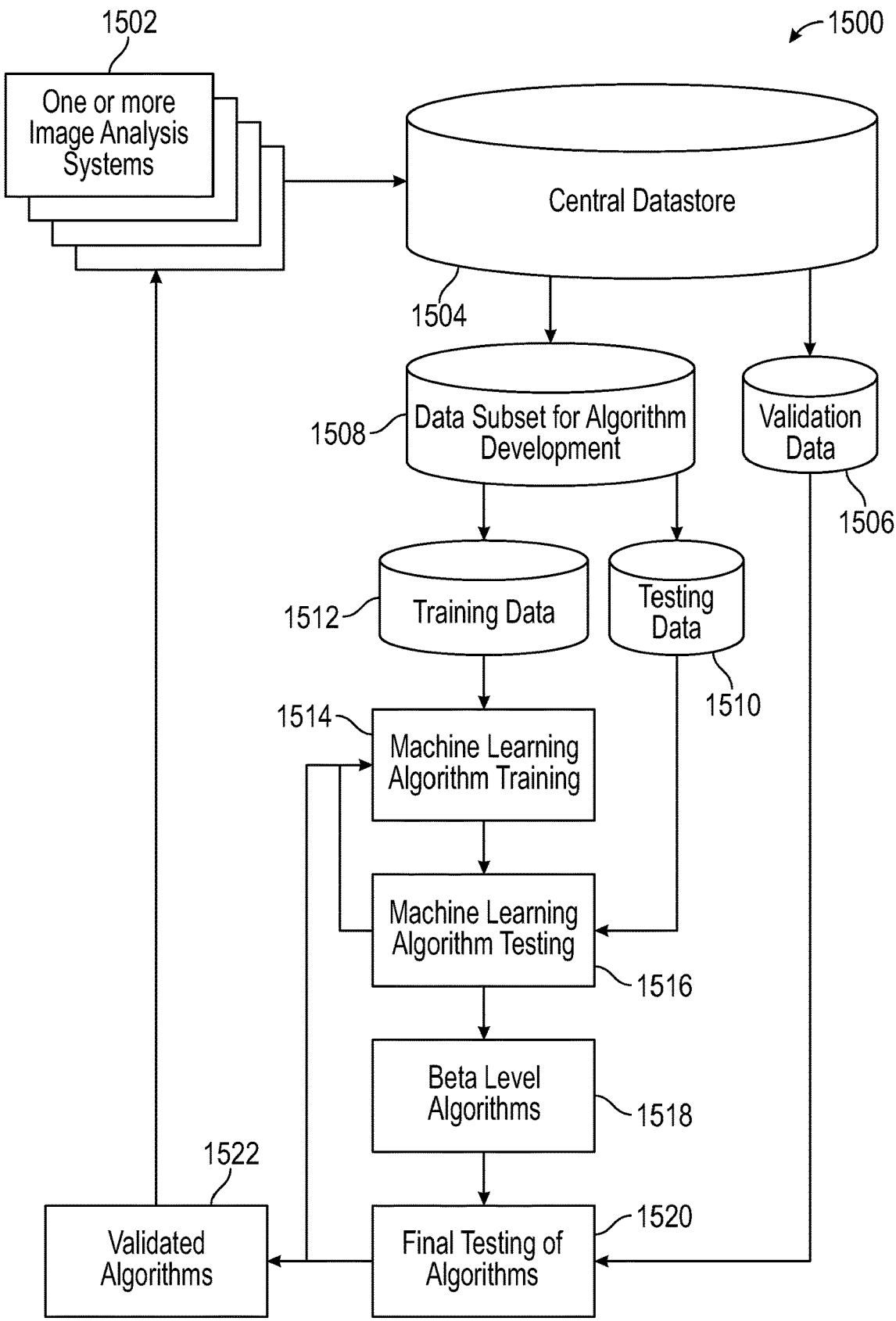
FIG. 15 is a flow diagram of an image analysis network showing how information contained in a central datastore can be used to train machine learning algorithms.

FIG. 15 is a flow diagram of an image analysis network 1500 showing how information contained in a central datastore 1504 can be used to train machine learning algorithms. Endoscopic case data of one or more cases from one or more image analysis systems 1502 is provided to a central datastore 1504. An appropriate data subset 1508 of endoscopic data from the central datastore is defined depending on the particular machine learning algorithm being trained. For example, a data subset for training a machine learning algorithm for tissue in a knee would be different from that used to train for tissue in a hip. It would also be different for different endoscopic domains. For example, data used to train an algorithm in arthroscopy would be different from data used to train an algorithm in laparoscopy.

Once an appropriate data subset 1508 is defined for training of a particular algorithm, it is divided into two groups: a set of training data 1512 and a set of testing data 1510. The training data 1512 is run through a machine learning algorithm training routine appropriate for the algorithm being trained. As an example, for training a machine learning algorithm to classify images within a general image characteristic category within arthroscopy, a series of images can be used that are already classified as one of: air, bloody, cloudy, out-of-focus, good and out-of-joint.

Once the training is done, the updated machine learning algorithm with appropriate parameters is tested 1516 using the reserved testing data 1510. The results of the testing are fed back to the algorithm training routine 1514 until an appropriate level of accuracy is achieved. At this point, the algorithms become beta level algorithms 1518.

Because any machine learning algorithms may ultimately be used in endoscopic systems for diagnosing and/or treating patients, any beta level algorithm may then go through another layer of final testing 1520 using reserved validation data 1506 to make sure the algorithms retain accuracy with data which was not associated with initial training and/or testing. At this point, the machine learning algorithm(s) become classified as validated algorithms 1522 and can be used to update one or more individual image analysis systems 1502.

While FIG. 15 illustrates the training process occurring with one central datastore 1504, as discussed above there can be more than one datastore with more than one location where algorithm development occurs. Additionally, local algorithm development can occur within an individual image analysis system using information contained in a local data capture engine of the image analysis system 1502. This can be useful, for example, as an individual image analysis system adapts to input from one or more users of that particular system. Any training done locally can be transferred to a central location containing information from a plurality of individual image analysis systems and stored there as well.

FIG. 16 shows a sample report 1600 that can be generated by an endoscopic procedure analysis system (e.g., endoscopic procedure analysis engine 491 in FIG. 4, endoscopic procedure analysis engine 1424 in FIG. 14) using aggregated endoscopic case data of a central datastore. As mentioned above, an endoscopic procedure analysis system can provide queries of data contained in a central datastore (e.g., central datastore 481 of FIG. 4) using any combination of any type of data contained in the central datastore, on any set of information from a single data point up through and including the entire central datastore. Calculated fields based on data in the central datastore can also be provided.

This sample report 1600 is for a specific procedure and is sorted by facility and surgeon 1602. In this example, a healthcare system 1604 is also chosen, which includes three facilities: two hospitals 1624 and one surgical center 1626. A specific procedure 1606 is chosen, in this case an ACL reconstruction, with or without a menisectomy, and with or without a chondroplasty. A date range 1608 for the report was also selected.

Headers show the information extracted from the central datastore for the report. The surgeon field 1610 lists the name(s) of the surgeon(s) for whom the data is applicable. The number of cases field 1612 lists the number of cases matching the procedure type 1606 for that particular surgeon 1610 during the time period 1608 selected.

The average time per case 1614 is calculated from information in the central datastore by an endoscopic procedure analysis system. This can be defined as the time from the first good image as defined by the image analysis engine until the last time the image showed the arthroscope was removed from the joint, also as defined by the image analysis system. These times can be more accurate than relying on a nurse or other member of the procedure team to press a button or otherwise record a time, as they are often busy or otherwise occupied during a case.

An average pressure per case 1616 can also be included in the sample report 1600. Because the control engine can continually monitor the actual pressures throughout a case, an average pressure can be determined by an endoscopic procedure analysis system as described above. This information is useful, for example, in outcome studies that correlate pain scores and/or recovery with pressures used during a case. Again, without a system utilizing a control engine that continually monitors the components of an endoscopic system throughout an entire case, this information is difficult to capture.

An example of a calculated field which could be used in a report is an extravasation score 1618. Extravasation occurs when fluid leaks out of an area being examined into surrounding tissues. This can be uncomfortable for a patient and, in worst cases, can lead to outcomes like increased pressure on the trachea in a shoulder case. The amount of extravasation is a function of pressure and time, both of which are quantities that can be tracked by an image analysis system. Information like this can be displayed during a case by a display engine and/or can be included in reports as shown in the sample report 1600. An extravasation score 1618 can be correlated with patient outcomes for studies looking for relationships between what happens during a procedure and what happens after a procedure.

An example of resource utilization that can be shown in a report is fluid used 1620. Different users can use quite different amounts of resources to do the same case. Because a control engine is continually monitoring the state of an endoscopic system throughout a case, information regarding resources used can be tracked. In this example, it is the average amount of fluid used throughout a case. Additional examples could include, but not be limited to: implants used, time spent in different parts of a case, instruments used, carbon dioxide used, and time spent using an argon beam coagulator.

The information can be presented in any format that may be useful or otherwise desired. In this case, there is a line for each surgeon 1628 showing information regarding that surgeon's cases that meet the selection criteria. There is also a line for the overall 1622 results, including for all facilities and all surgeons thereat.

As is readily apparent to those familiar with database management, a multitude of queries can be performed with various combinations of selection criteria and/or data extracted. Calculated fields can be a part of the query. Notably, an endoscopic procedure analysis system can be used to extract information from endoscopic case data created and/or stored by one or more individual image analysis systems. The results of the query can be presented or otherwise provided in any form including, but not limited to, one or more of: printed reports, electronic reports formatted for printing, images, delimited data, table data, and data formatted to meet a specific API for an EMR system.

Figure 17:
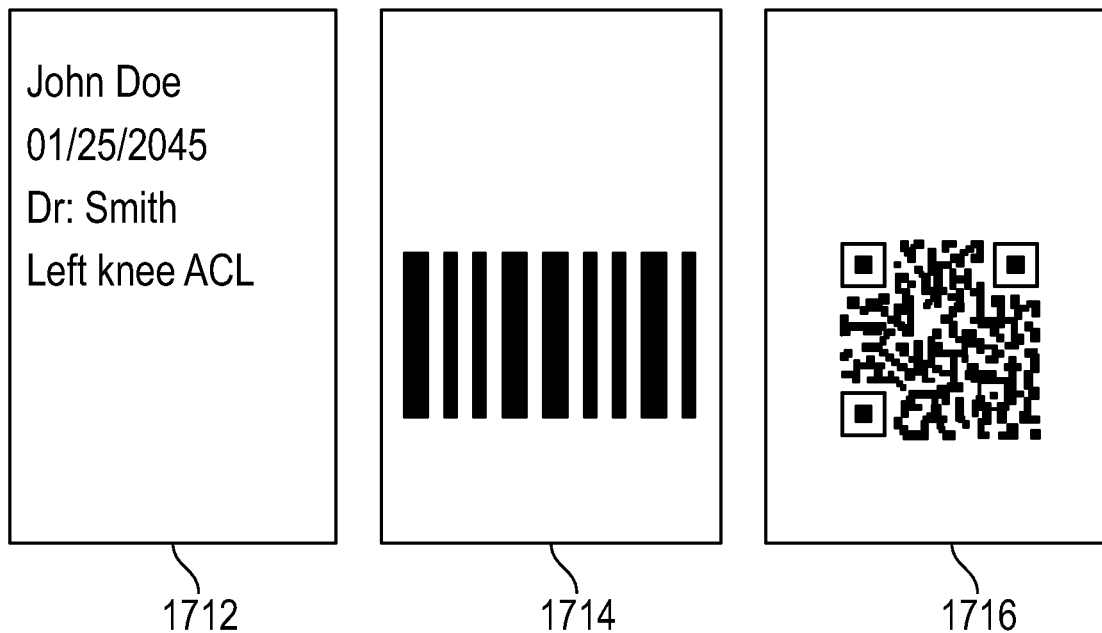
FIG. 17 illustrates an example of how a camera that is normally used to capture endoscopic images for display during a procedure can be used to input other types of data for use in an endoscopic system.
Figure 17:
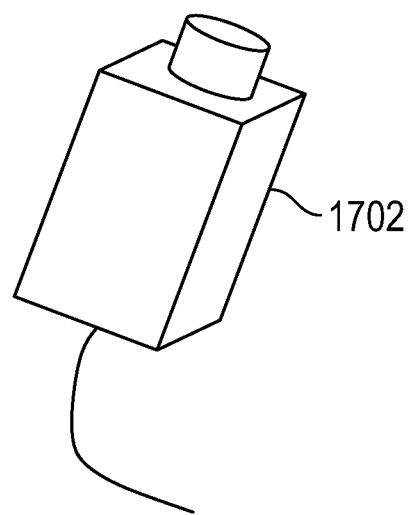

FIG. 17 shows an example of how a camera 1702 normally used to capture endoscopic images for display during a procedure can be used to input other types of data for use in an endoscopic system. A camera 1702 can be pointed at a location outside a patient to input data. This can be any type of visual representation of information including, but not limited to, one or more of the following: alphanumeric characters 1712, bar codes 1714, and quick response (QR) codes 1716. Appropriate routines can be used to extract information from images captured by the endoscopic camera 1702.

As an example, in a case the camera 1702 can be pointed at and capture an image of a printed sticker and/or sheet that contains, but is not limited to, one or more of the following: patient demographic information, user information, preoperative diagnoses, planned procedures, and consent information. This image could be processed by an image analysis engine (e.g., image analysis component 350 in FIG. 3) using optical character recognition (OCR) algorithms and extracted data passed to a content management system (e.g., content management system 324 in FIG. 3).

As another example, a printed sheet, a table, or other surface attached to an endoscopic tower and/or somewhere else easily accessible can contain barcodes, QR codes, and/or any other type of visual representation of information. When the camera 1702 is pointed at individual codes to capture images, case identifying data can be decoded from the image(s) and used to populate appropriate data fields of case identifying data for use in an image analysis system. For example, when doing an arthroscopy, a surgeon or other member of a procedure team could point the camera 1702 at a series of one or more codes to select right, shoulder and rotator cuff repair.

While these are specific examples, any use of an endoscopic camera 1702 to decode visual information captured by that camera for use in an endoscopic system can be considered an embodiment of the present disclosure.

While the functionality of an image analysis system as described is generally embodied as connected to and/or controlling an endoscopic system during a case, an image analysis system can also be embodied virtually with a reduced function set. For example, a user could capture one or more images and/or a video from an endoscopic case. These images and/or video could then be run through a version of an image analysis system, whether locally (e.g. on a computer or connected to an endoscopic system) or remotely (e.g. uploaded via a website to a virtual image analysis system). A virtual image analysis system may have reduced control features or entirely lack control features, but image data (e.g., videos, images) of procedures or cases may be uploaded to have the image analysis performed virtually. Case data can be extracted from such image data. For example, videos could be uploaded after each case, and a virtual image analysis system could get things like procedure times, diagnoses, procedures, etc. A virtual system may also provide demonstration functionality where video of a case can be uploaded and the system demonstrates what a local (rather than virtual) image analysis system would do. An image normalization engine and an image analysis engine 402 could then analyze the images and/or video from a file as opposed to receiving image data input from, for example, a physical video connection. The outputs from the image analysis engine could be saved by a data capture engine. The remaining functionality of the image analysis system as described herein could then be operable as applicable.

Some examples of how a virtual image analysis system can be useful include, but are not limited to, one or more of the following: calculating case times from the video, extracting tissue information, determining diagnoses, determining procedures, automatically annotating images and/or video, training algorithms, and identifying implants.

EXAMPLES

Some examples of an embodiment of the present disclosure is provided below.

Example 1. A system to facilitate performing an endoscopic procedure comprising: an endoscope to provide a user (e.g., surgeon) with access to a view of an area (e.g., one or more structures) to be visualized or otherwise made visual or visible that is inside a body of a patient and that is within a field of vision of the endoscope; a camera or imager to capture image data of the area to be visualized; a pump or other medium management system (e.g., insufflator) to manage a viewing medium, such as fluid (liquid/gas), through an inflow cannula, at the area to be visualized; an image analysis unit to: receive an image of the view of the area to be visualized, wherein the image is from the image data; and determine a characteristic (and/or classification) of the image; and a control unit to control or command the pump or other medium management system, such as by adjusting parameters of the pump, based on the characteristic of the image.

The foregoing specification has been described with reference to various embodiments, including the best mode. However, those skilled in the art appreciate that various modifications and changes can be made without departing from the scope of the present disclosure and the underlying principles of the invention. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection.

The phrase "coupled to" is broad enough to refer to any suitable coupling or other form of interaction between two or more entities, including mechanical interaction, electrical interaction, and wireless communication interaction. Thus, two components may be coupled to each other even though they are not in direct contact with each other. The phrase "attached to" refers to interaction between two or more entities that are in direct contact with each other or are separated from each other only by a fastener of any suitable variety (e.g., mounting hardware or an adhesive).

References to approximations are made throughout this specification, such as by use of the term "substantially." For each such reference, it is to be understood that, in some embodiments, the value, feature, or characteristic may exist without approximation. For example, where qualifiers such as "about" and "substantially" are used, these terms include within their scope the qualified words in the absence of their qualifiers. For example, where the term "substantially perpendicular" is recited with respect to a feature, it is understood that in some embodiments the feature may have a precisely perpendicular configuration.

Principles of the present disclosure may be reflected in a computer program product on a tangible computer-readable storage medium having computer-readable program code means embodied in the storage medium. Any suitable computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture including instruction means which implement the function specified. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified.

Principles of the present disclosure may be reflected in a computer program implemented as one or more software modules or components. As used herein, a software module or component (e.g., engine, system, subsystem) may include any type of computer instruction or computer-executable code located within a memory device and/or computer-readable storage medium. A software module may, for instance, comprise one or more physical or logical blocks of computer instructions, which may be organized as a routine, a program, an object, a component, a data structure, etc., that perform one or more tasks or implement particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Suitable software to assist in implementing the invention is readily provided by those of skill in the pertinent art(s) using the teachings presented here and programming languages and tools, such as Java, Pascal, C++, C, database languages, APIs, SDKs, assembly, firmware, microcode, and/or other languages and tools.

Embodiments as disclosed herein may be computer-implemented in whole or in part on a digital computer. The digital computer includes a processor performing the required computations. The computer further includes a memory in electronic communication with the processor to store a computer operating system. The computer operating systems may include, but are not limited to, MS-DOS, Windows, Linux, Unix, AIX, CLIX, QNX, OS/2, and Apple. Alternatively, it is expected that future embodiments will be adapted to execute on other future operating systems.

In some cases, well-known features, structures or operations are not shown or described in detail. Furthermore, the described features, structures, or operations may be combined in any suitable manner in one or more embodiments. It will also be readily understood that the components of the embodiments as generally described and illustrated in the figures herein could be arranged and designed in a wide variety of different configurations.

Various operational steps, as well as components for carrying out operational steps, may be implemented in alternate ways depending upon the particular application or in consideration of any number of cost functions associated with the operation of the system, e.g., one or more of the steps may be deleted, modified, or combined with other steps.

While the principles of this disclosure have been shown in various embodiments, many modifications of structure, arrangements, proportions, the elements, materials and components, used in practice, which are particularly adapted for a specific environment and operating requirements, may be used without departing from the principles and scope of this disclosure. These and other changes or modifications are intended to be included within the scope of the present disclosure.

The scope of the present invention should, therefore, be determined only by the following claims.

What is claimed is:

1. An endoscopic system for performing an endoscopic procedure comprising:
    an endoscope to provide a user access to view an area to be visualized that is inside a body of a patient;
    a camera to capture image data of the area to be visualized;
    a pump to provide a viewing medium through an inflow cannula at the area to be visualized;
    an image analysis engine to:
        receive an image of the view of the area to be visualized, wherein the image is from the image data, and wherein the image is captured by the endoscope while the endoscope is inserted in the inflow cannula; and
        determine, using a neural network which receives the image as input, a characteristic of the image, wherein the characteristic indicates whether the endoscope is in the body of the patient or out of the body of the patient, wherein if the characteristic indicates that the endoscope is in the body of the patient, the characteristic indicates an anatomic sublocation; and
    a control engine to provide control to the pump based on the characteristic of the image.

2. The system of claim 1, wherein the control engine controls the pump based on the characteristic to at least one of:
increase one or more of pressure in the area to be visualized and flow of viewing medium into the area to be visualized; and
decrease one or more of pressure in the area to be visualized and flow of viewing medium into the area to be visualized.

3. The system of claim 2, wherein the control engine controls the pump based on the characteristic until the characteristic changes.

4. The system of claim 1, wherein the image data comprises video.

5. The system of claim 4, wherein the image analysis engine processes individual frames of the video.

6. The system of claim 1, further comprising an image processing component to convert raw data of the camera into the image data.

7. The system of claim 1, wherein the area to be visualized is within a knee of the patient.

8. The system of claim 1, wherein the characteristic is determined to be one of:
air;
out of focus;
cloudy;
bloody;
out of body; and
good.

9. The system of claim 8, wherein, if the characteristic is determined to be one of cloudy and bloody, operation of the pump is adjusted to increase one or more of pressure at the area of visualization and flow of viewing medium into the area of visualization.

10. The system of claim 1, further comprising a light source to provide illumination of the area to be visualized, wherein the control engine is to control the light source based on the characteristic of the image.

11. The system of claim 1, further comprising a motorized device configured to manipulate tissue,
wherein the control engine is to control the motorized device based on the characteristic of the image.

12. The system of claim 1, further comprising an outflow control component to allow manipulation of a rate at which the viewing medium leaves the area to be visualized,
wherein the control engine is to control the outflow control component based on the characteristic of the image.

13. The system of claim 1, wherein the image analysis engine is to determine a plurality of characteristics of the image, and
wherein the control engine is to adjust one or more components of the endoscopic system based on the plurality of characteristics of the image.

14. The system of claim 13, wherein the image analysis engine is to determine each characteristic of the plurality of characteristics of the image from a different predefined category of characteristic.

15. The system of claim 14, wherein the category of characteristic of each of the plurality of characteristics is one of: general image, tissue, and procedure.

16. The system of claim 1, further comprising a display engine to convey the results of image classification to a user.

17. The system of claim 1, further comprising a data capture engine to store the results of one or more image classification categories as well as state data for any component controlled by the controller engine.

18. The system of claim 1, wherein the area to be visualized is within a shoulder of the patient.

19. The system of claim 1, wherein the area to be visualized is within a hip of the patient.

* * * * *